United States Patent
Lian et al.

(10) Patent No.: US 12,408,666 B2
(45) Date of Patent: *Sep. 9, 2025

(54) PYRIDYLOXY CARBOXYLATE DERIVATIVE, PREPARATION METHOD THEREFOR, HERBICIDAL COMPOSITION AND USE THEREOF

(71) Applicant: Qingdao Kingagroot Chemical Compound Co., Ltd., Qingdao (CN)

(72) Inventors: Lei Lian, Qingdao (CN); Xuegang Peng, Qingdao (CN); Rongbao Hua, Qingdao (CN); Jingyuan Zhang, Qingdao (CN); Qi Cui, Qingdao (CN)

(73) Assignee: Qingdao Kingagroot Chemical Compound Co., Ltd., Qingdao (CN)

( * ) Notice: Subject to any disclaimer, the term of this patent is extended or adjusted under 35 U.S.C. 154(b) by 868 days.

This patent is subject to a terminal disclaimer.

(21) Appl. No.: 17/414,478

(22) PCT Filed: Dec. 27, 2018

(86) PCT No.: PCT/CN2018/124459
§ 371 (c)(1),
(2) Date: Jun. 16, 2021

(87) PCT Pub. No.: WO2020/133091
PCT Pub. Date: Jul. 2, 2020

(65) Prior Publication Data
US 2022/0053763 A1    Feb. 24, 2022

(51) Int. Cl.
| | | |
|---|---|---|
| *A01N 43/40* | (2006.01) | |
| *A01N 43/54* | (2006.01) | |
| *C07D 213/24* | (2006.01) | |
| *C07D 213/73* | (2006.01) | |
| *C07D 401/12* | (2006.01) | |
| *C07D 405/12* | (2006.01) | |
| *C07D 409/12* | (2006.01) | |
| *C07D 417/12* | (2006.01) | |

(52) U.S. Cl.
CPC .............. *A01N 43/40* (2013.01); *A01N 43/54* (2013.01); *C07D 213/24* (2013.01); *C07D 213/73* (2013.01); *C07D 401/12* (2013.01); *C07D 405/12* (2013.01); *C07D 409/12* (2013.01); *C07D 417/12* (2013.01)

(58) Field of Classification Search
CPC ...... A01N 43/40; A01N 43/54; C07D 213/24; C07D 213/73; C07D 401/12; C07D 405/12; C07D 409/12; C07D 417/12
See application file for complete search history.

(56) References Cited

U.S. PATENT DOCUMENTS

| | | | |
|---|---|---|---|
| 3,755,339 A | 8/1973 | McKendry | |
| 3,761,486 A | 9/1973 | McGregor | |
| 4,014,888 A | 3/1977 | McKendry | |
| 4,108,629 A | 8/1978 | McKendry | |
| 4,110,104 A | 8/1978 | McGregor | |
| 5,013,659 A | 5/1991 | Bedbrook et al. | |

FOREIGN PATENT DOCUMENTS

| | | |
|---|---|---|
| CN | 104592103 A | 5/2015 |
| DE | 2335349 A1 | 1/1975 |
| EP | 0131624 B1 | 1/1985 |
| EP | 0142924 A2 | 5/1985 |
| EP | 0193259 A1 | 9/1986 |
| EP | 0221044 A1 | 5/1987 |
| EP | 0242236 A1 | 10/1987 |
| EP | 0242246 A1 | 10/1987 |
| EP | 0257993 A2 | 3/1988 |
| GB | 1418979 | 12/1975 |
| GB | 2182562 A | 5/1987 |
| WO | WO91/13972 A1 | 9/1991 |
| WO | WO91/19806 A1 | 12/1991 |
| WO | WO92/00377 A1 | 1/1992 |
| WO | WO92/11376 A1 | 7/1992 |
| WO | WO92/14827 A1 | 9/1992 |

OTHER PUBLICATIONS

Li, W.Z.; Liu, H.Q.; Qi, X.; Sun, H.B. "Application of phase transfer catalyst in the synthesis of cyhalofop butyl" J. Chem. Pharm. Res., 2013, 5(12):275-278. (Year: 2013).*

Panda, R.; Ariyarathna, P.; Amnuaycheewa, A.T.; et al. "Challenges in testing genetically modified crops for potential increases in endogenous allergen expression for safety" Allergy 68 (2013) 142-151. (Year: 2013).*

Christou P, Transformation Technology, Trends in Plant Science, 1:423-431 (1996).

Braun et al., The General Mitochondrial Processing Peptidase from Potato Is an Integral Part of Cytochrome C Reductase of The Respiratory Chain, Embo J. 11:3219-3227 (1992).

(Continued)

*Primary Examiner* — Andrew D Kosar
*Assistant Examiner* — John D Mcanany
(74) *Attorney, Agent, or Firm* — FINNEGAN, HENDERSON, FARABOW, GARRETT & DUNNER LLP

(57) ABSTRACT

The present disclosure relates to the field of pesticide technology, and in particular pyridyloxy carboxylate derivatives of Formula I, preparation methods, herbicidal compositions and applications thereof.

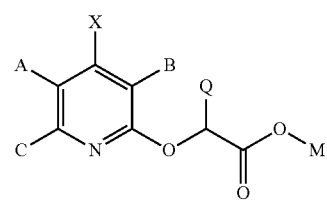

19 Claims, No Drawings

(56) References Cited

OTHER PUBLICATIONS

Wolter et al., Rbcs Genes in Solanum Tuberosum: Conservation of Transit Peptide and Exon Shuffling During Evolution, Proc. Natl. Acad. Sci. USA, 85:846-850 (1988).
Sonnewald et al., Transgenic Tobacco Plants Expressing Yeast-Derived Invertase in Either the Cytosol, Vacuole or Apoplast: A Powerful Tool for Studying Sucrose Metabolism and Sink/Source Interactions, Plant J. 1:95-106 (1991).
International Search Report of International Application No. PCT/CN2018/124459, dated Sep. 27, 2019.
Written Opinion of International Application No. PCT/CN2018/124459, dated Sep. 23, 2019.
Baoguo Guo et al. *Important Unit Reactions in Organic Synthesis*, The Yellow River Water Conservancy Press, CN, cover and pp. 135-137, Jun. 2009.

* cited by examiner

PYRIDYLOXY CARBOXYLATE DERIVATIVE, PREPARATION METHOD THEREFOR, HERBICIDAL COMPOSITION AND USE THEREOF

CROSS REFERENCE TO RELATED APPLICATION

This application is a national stage filing under 35 U.S.C. § 371 of International Application No. PCT/CN2018/124459, filed Dec. 27, 2018, which is incorporated herein by reference in its entirety.

TECHNICAL FIELD

The invention relates to the field of pesticide technology, and in particular a type of pyridyloxy carboxylate derivative, preparation method, herbicidal composition and application thereof.

TECHNICAL BACKGROUND

Weed control is one of the most important links in the course of achieving high-efficiency agriculture. Various herbicides are available in the market, for example, DE2335349A1, GB1418979A, U.S. Pat. Nos. 3,755,339, 4,110,104 and the like disclose a series of compounds represented by the general formula

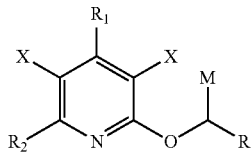

and application thereof as herbicides. However, due to the continuous expansion of the market, the resistance of weeds, the service life of chemicals and the economical efficiency of chemicals, as well as the increasing emphasis on the environment, especially the serious occurrence of resistance to mainstream paddy field grass weed herbicides (e.g., herbicides with the inhibition mechanism of ALS such as Penoxsulam, Bispyribac-sodium, and Pyribenzoxim, herbicides with ACCe-based inhibition mechanism such as Cyhalofop-butyl, as well as metamifop and the like) in the market, the prevention and control of *Echinochloa crusgalli, Digitaria sanguinalis, Setaria viridis, Leptochloa chinensis* and other gramineous grasses in rice fields encounters a serious challenge and lack effective chemicals to control weeds with resistance. This requires scientists to continuously research and develop new high-efficiency, safe, economic herbicides with different action modes.

Invention Contents

The present invention provides a type of pyridyloxy carboxylate derivative, preparation method, herbicidal composition and application thereof. The compound has excellent herbicidal activity and higher crop safety, especially good selectivity for key crops such as rice and soybean.

The technical solution adopted by the invention is as follows:

A pyridyloxy carboxylate derivative represented by formula I,

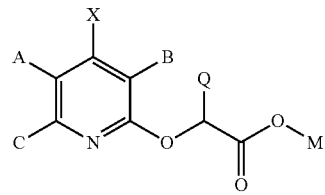

wherein, A, B each independently represent halogen; or alkyl or cycloalkyl with or without halogen;

C represents hydrogen, halogen, alkyl or haloalkyl;

Q represents halogen, cyano, cyanoalkyl, hydroxyalkyl, amino, nitro, formyl; alkyl, alkenyl, alkynyl, cycloalkyl, alkoxy, alkylthio, alkylcarbonyl, alkoxycarbonyl, alkylaminoalkyl or alkoxyalkyl with or without halogen; or unsubstituted or substituted aryl, heteroaryl, arylalkyl or heteroarylalkyl;

M represents -alkyl-R, -haloalkyl-R or

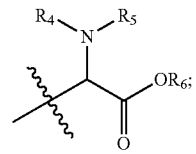

R represent

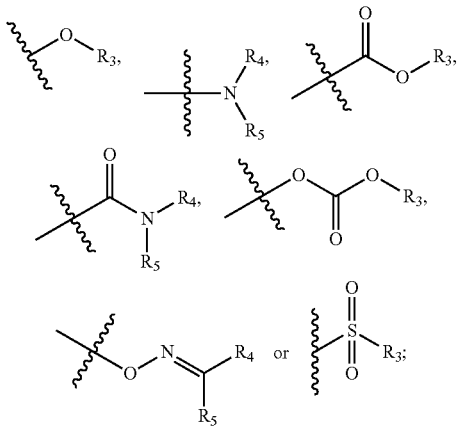

$R_3$ each independently represents hydrogen, alkyl, alkenyl, alkynyl, cycloalkyl, cycloalkylalkyl; or unsubstituted or substituted heterocyclyl, aryl, heteroaryl, heterocyclylalkyl, arylalkyl or heteroarylalkyl;

$R_4$, $R_5$, and $R_6$ each independently represent hydrogen, alkyl, alkenyl, alkynyl, cycloalkyl, cycloalkylalkyl, alkoxy, alkoxycarbonyl; or unsubstituted or substituted heterocyclyl, aryl, heteroaryl, heterocyclylalkyl, arylalkyl or heteroarylalkyl;

X represents nitro or $NR_1R_2$, wherein $R_1$ represents H; alkyl, alkenyl or alkynyl optionally substituted by 1-2 $R_{11}$; —$COR_{12}$, nitro, $OR_{13}$, $SO_2R_{14}$, $NR_{15}R_{16}$, N=CR₁₇R₁₈, alkylcarbamoyl, dialkylcarbamoyl, trialkylsilyl or dialkylphosphono; R₂ represents H; alkyl optionally substituted by 1-2 R₁₁; or —COR₁₂; or NR₁R₂ represents N=CR₂₁NR₂₂R₂₃, N=CR₂₄OR₂₅; or a 5- or 6-membered saturated or unsaturated ring with or without oxygen atom, sulfur atom, or other nitrogen atom, which is unsubstituted or substituted by 1-2 groups independently selected from the group consisting of halogen, alkyl, alkoxy, haloalkoxy, alkylthio, haloalkylthio, amino, alkylamino, dialkylamino and alkoxycarbonyl;

wherein R₁₁ independently represents halogen, hydroxy, alkoxy, haloalkoxy, alkylthio, haloalkylthio, amino, alkylamino, dialkylamino, alkoxycarbonyl; or unsubstituted or substituted aryl or heteroaryl;

R₁₂ represents H, alkyl, haloalkyl, alkoxy, phenyl, phenoxy or benzyloxy;

R₁₃ represents H, alkyl, haloalkyl, phenyl, benzyl or CHR₃₁C(O)OR₃₂; R₃₁ represents H, alkyl or alkoxy; R₃₂ represents H, alkyl or benzyl;

R₁₄ represents alkyl or haloalkyl;

R₁₅ represents H, alkyl, formyl, alkylacyl, haloalkylacyl, alkoxycarbonyl, phenylcarbonyl, phenoxycarbonyl or benzyloxycarbonyl; R₁₆ represents H or alkyl;

R₁₇ represents H, alkyl; or phenyl that is unsubstituted or substituted by 1-3 groups selected from the group consisting of halogen, alkyl and alkoxy; R₁₈ represents H or alkyl; or N=CR₁₇R₁₈ represents

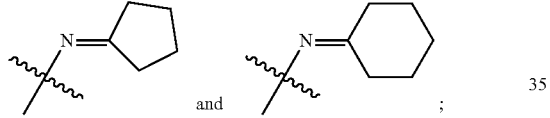

R₂₁, R₂₄ each independently represent H or alkyl;

R₂₂, R₂₃ each independently represent H or alkyl; or NR₂₂R₂₃ represents a 5- or 6-membered saturated or unsaturated ring with or without oxygen atom, sulfur atom, or other nitrogen atom;

R₂₅ represents alkyl.

Preferably, A, B each independently represent halogen; or C1-C8 alkyl or C3-C8 cycloalkyl with or without halogen;

C represents hydrogen, halogen, C1-C8 alkyl or halo C1-C8 alkyl;

Q represents halogen, cyano, cyano C1-C8 alkyl, hydroxy C1-C8 alkyl, amino, nitro, formyl; C1-C8 alkyl, C2-C8 alkenyl, C2-C8 alkynyl, C3-C8 cycloalkyl, C1-C8 alkoxy, C1-C8 alkylthio, C1-C8 alkylcarbonyl, C1-C8 alkoxycarbonyl, C1-C8 alkylamino C1-C8 alkyl or C1-C8 alkoxy C1-C8 alkyl with or without halogen; or unsubstituted or substituted aryl, heteroaryl, aryl C1-C8 alkyl or heteroaryl C1-C8 alkyl;

M represents —(C1-C8)alkyl-R, -halo(C1-C8)alkyl-R or

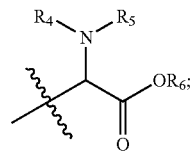

R represents

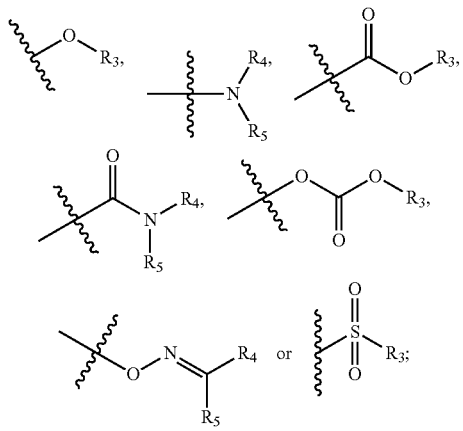

R₃ each independently represents hydrogen, C1-C8 alkyl, C2-C8 alkenyl, C2-C8 alkynyl, C3-C8 cycloalkyl, C3-C8 cycloalkyl C1-C8 alkyl; or unsubstituted or substituted heterocyclyl, aryl, heteroaryl, heterocyclyl C1-C8 alkyl, aryl C1-C8 alkyl or heteroaryl C1-C8 alkyl;

R₄, R₅, and R₆ each independently represent hydrogen, C1-C8 alkyl, C2-C8 alkenyl, C2-C8 alkynyl, C3-C8 cycloalkyl, C3-C8 cycloalkyl C1-C8 alkyl, C1-C8 alkoxy, C1-C8 alkoxycarbonyl; or unsubstituted or substituted heterocyclyl, aryl, heteroaryl, heterocyclyl C1-C8 alkyl, aryl C1-C8 alkyl or heteroaryl C1-C8 alkyl;

X represents nitro or NR₁R₂, wherein R₁ represents H; C1-C8 alkyl, C2-C8 alkenyl or C2-C8 alkynyl optionally substituted by 1-2 R₁₁; —COR₁₂, nitro, OR₁₃, SO₂R₁₄, NR₁₅R₁₆, N=CR₁₇R₁₈, C1-C8 alkylcarbamoyl, di-C1-C8 alkylcarbamoyl, tri-C1-C8 alkylsilyl or di-C1-C8 alkylphosphono; R₂ represents H; C1-C8 alkyl optionally substituted by 1-2 R₁₁; or —COR₁₂; or NR₁R₂ represents N=CR₂₁NR₂₂R₂₃, N=CR₂₄OR₂₅; or

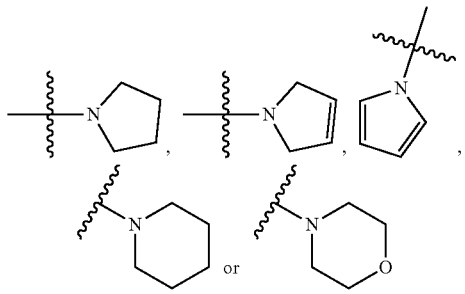

that is unsubstituted or substituted by 1-2 groups independently selected from the group consisting of halogen, C1-C8 alkyl, C1-C8 alkoxy, halo C1-C8 alkoxy, C1-C8 alkylthio, halo C1-C8 alkylthio, amino, C1-C8 alkylamino, di-C1-C8 alkylamino and C1-C8 alkoxycarbonyl;

wherein R₁₁ independently represents halogen, hydroxy, C1-C8 alkoxy, halo C1-C8 alkoxy, C1-C8 alkylthio, halo C1-C8 alkylthio, amino, C1-C8 alkylamino, di-C1-C8 alkylamino, C1-C8 alkoxycarbonyl; or phenyl, naphthyl,

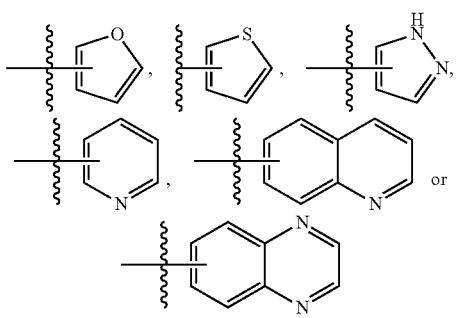

that is unsubstituted or substituted by 1-3 groups selected from the group consisting of halogen, C1-C8 alkyl, halo C1-C8 alkyl, C1-C8 alkoxy and nitro;

$R_{12}$ represents H, C1-C18 alkyl, halo C1-C8 alkyl, C1-C8 alkoxy, phenyl, phenoxy or benzyloxy;

$R_{13}$ represents H, C1-C8 alkyl, halo C1-C8 alkyl, phenyl, benzyl or $CHR_{31}C(O)OR_{32}$; $R_{31}$ represents H, C1-C8 alkyl or C1-C8 alkoxy; $R_{32}$ represents H, C1-C8 alkyl or benzyl;

$R_{14}$ represents C1-C8 alkyl or halo C1-C8 alkyl;

$R_{15}$ represents H, C1-C8 alkyl, formyl, C1-C8 alkylacyl, halo C1-C8 alkylacyl, C1-C8 alkoxycarbonyl, phenyl-carbonyl, phenoxycarbonyl or benzyloxycarbonyl; $R_{16}$ represents H or C1-C8 alkyl;

$R_{17}$ represents H, C1-C8 alkyl; or phenyl that is unsubstituted or substituted by 1-3 groups selected from the group consisting of halogen and C1-C8 alkyl, C1-C8 alkoxy; $R_{18}$ represents H or C1-C8 alkyl; or $N{=}CR_{17}R_{18}$ represents

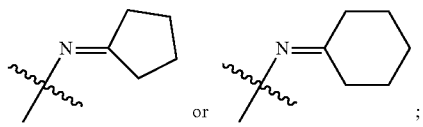 [SMILES: *N=C1CCCC1 ; *N=C1CCCCC1]

$R_{21}$, $R_{24}$ each independently represent H or C1-C8 alkyl; $R_{22}$, $R_{23}$ each independently represent H or C1-C8 alkyl; or $NR_{22}R_{23}$ represents

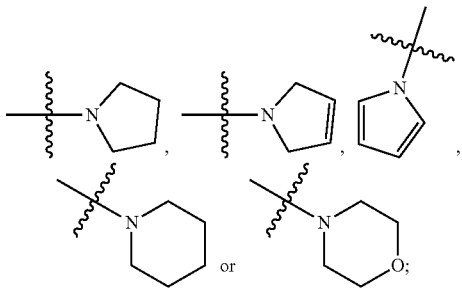

$R_{25}$ represents C1-C8 alkyl;
the term "heterocyclyl" refers to

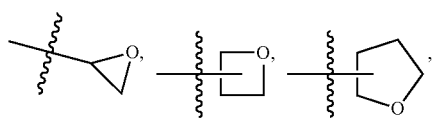

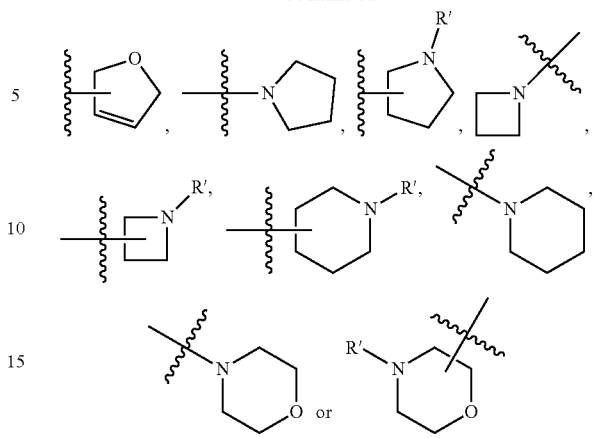

with 0, 1 or 2 oxo groups; the term "aryl" refers to phenyl or naphthyl; the term "heteroaryl" refers to an aromatic ring group containing 3 to 6 ring atoms and is optionally fused via benzo ring, 1 to 4 heteroatoms in the ring atoms being selected from oxygen, nitrogen and sulfur, for example,

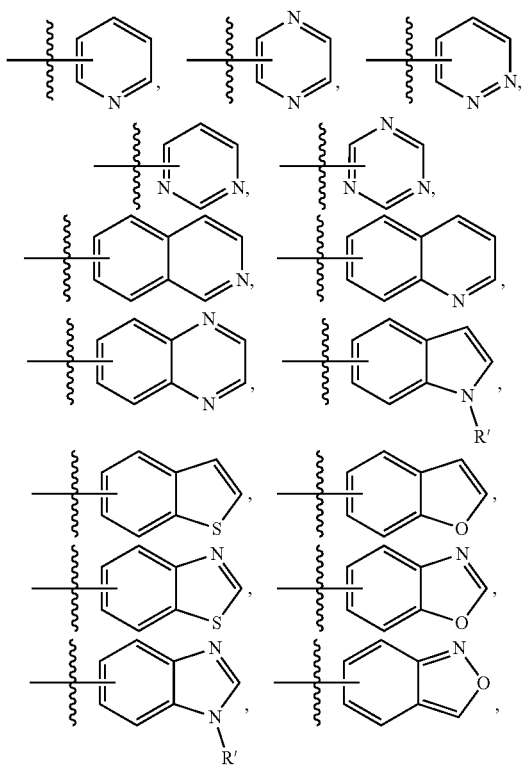

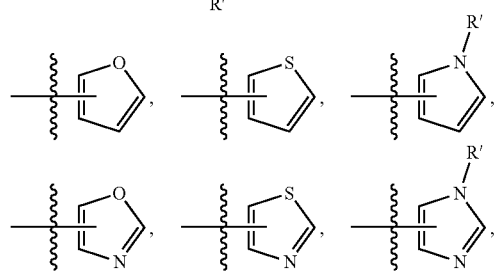

-continued

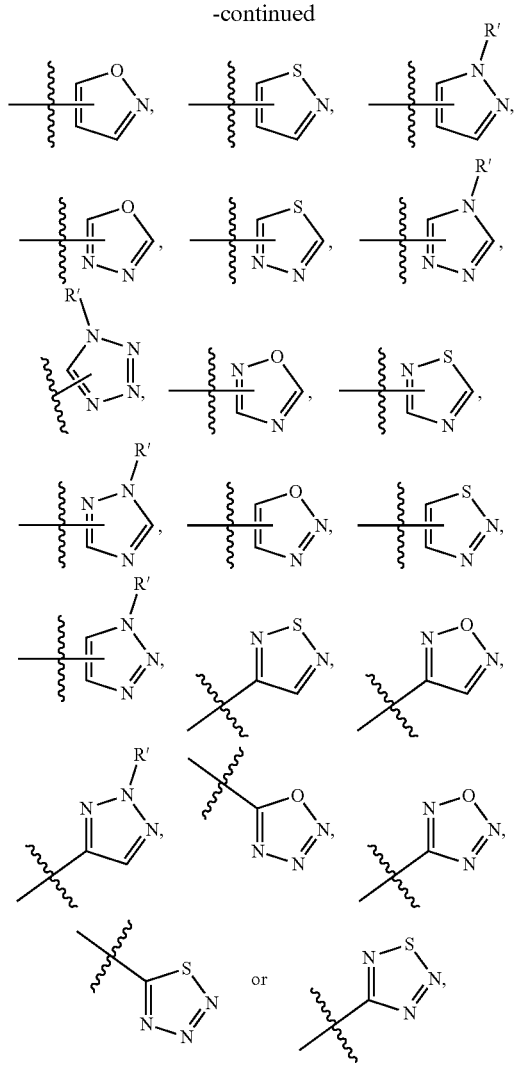

which is optionally substituted by at least one group selected from the group consisting of halogen, nitro, cyano, thiocyano, hydroxy, carboxy, mercapto, formyl; phenyl, benzyl, benzyloxy, phenoxy that is unsubstituted or substituted by at least one group from the group consisting of halogen, alkyl and alkoxy; alkyl, alkenyl, alkynyl, cycloalkyl, cycloalkylalkyl, OR", SR", -alkyl-OR", -alkyl-SR", COR", COOR", COSR", SOR", SO$_2$R", OCOR" or SCOR" with or without halogen; and amino or aminocarbonyl substituted by one or two groups selected from the group consisting of hydrogen, alkyl, alkenyl, alkynyl, cycloalkyl, cycloalkylalkyl, phenyl, benzyl, benzyloxy, phenoxy, COR", COOR", SO$_2$R" and OR";

R' each independently represents hydrogen, nitro, hydroxy, amino; or alkyl, alkenyl, alkynyl, cycloalkyl, cycloalkenyl, cycloalkylalkyl, alkoxy, alkenyloxy, alkynyloxy, cycloalkyloxy, alkoxyalkyl, alkoxycarbonyl, alkylthiocarbonyl, alkylsulfonyl, alkylsulfonylalkyl, alkylcarbonyl, alkylcarbonylalkyl, alkylacyloxy, alkylamino, alkylaminocarbonyl, alkoxyaminocarbonyl, alkoxycarbonylalkyl, alkylaminocarbonylalkyl, trialkylsilyl or dialkylphosphono with or without halogen;

R" each independently represents hydrogen, alkyl, alkenyl, alkynyl, cycloalkyl or cycloalkylalkyl.

More preferably, A, B each independently represent halogen; or C1-C6 alkyl or C3-C6 cycloalkyl with or without halogen;

C represents hydrogen, halogen, C1-C6 alkyl or halo C1-C6 alkyl;

Q represents halogen, cyano, cyano C1-C6 alkyl, hydroxy C1-C6 alkyl, amino, nitro, formyl; C1-C6 alkyl, C2-C6 alkenyl, C2-C6 alkynyl, C3-C6 cycloalkyl, C1-C6 alkoxy, C1-C6 alkylthio, C1-C6 alkylcarbonyl, C1-C6 alkoxycarbonyl, C1-C6 alkylamino C1-C6 alkyl or C1-C6 alkoxy C1-C6 alkyl with or without halogen; or unsubstituted or substituted aryl, heteroaryl, aryl C1-C6 alkyl or heteroaryl C1-C6 alkyl;

M represents —(C1-C6)alkyl-R, -halo(C1-C6)alkyl-R or

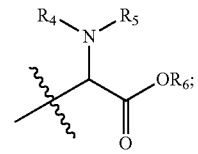

R represents

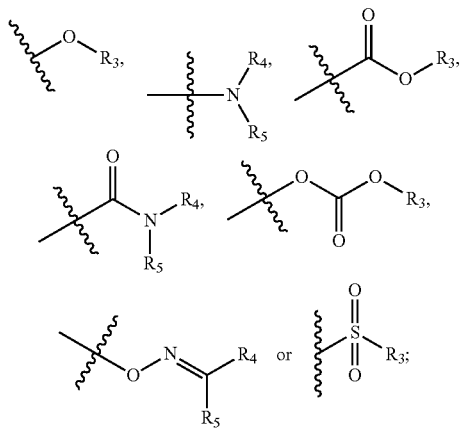

R$_3$ each independently represents hydrogen, C1-C6 alkyl, C2-C6 alkenyl, C2-C6 alkynyl, C3-C6 cycloalkyl, C3-C6 cycloalkyl C1-C6 alkyl; or unsubstituted or substituted heterocyclyl, aryl, heteroaryl, heterocyclyl C1-C6 alkyl, aryl C1-C6 alkyl or heteroaryl C1-C6 alkyl;

R$_4$, R$_5$, and R$_6$ each independently represent hydrogen, C1-C6 alkyl, C2-C6 alkenyl, C2-C6 alkynyl, C3-C6 cycloalkyl, C3-C6 cycloalkyl C1-C6 alkyl, C1-C6 alkoxy, C1-C6 alkoxycarbonyl; or unsubstituted or substituted heterocyclyl, aryl, heteroaryl, heterocyclyl C1-C6 alkyl, aryl C1-C6 alkyl or heteroaryl C1-C6 alkyl;

X represents nitro or NR$_1$R$_2$, wherein R$_1$ represents H; C1-C6 alkyl, C2-C6 alkenyl or C2-C6 alkynyl optionally substituted by 1-2 R$_{11}$; —COR$_{12}$, nitro, OR$_{13}$, SO$_2$R$_{14}$, NR$_{15}$R$_{16}$, N=CR$_{17}$R$_{18}$, C1-C6 alkylcarbamoyl, di-C1-C6 alkylcarbamoyl, tri-C1-C6 alkylsilyl or di-C1-C6 alkylphosphono; R$_2$ represents H; C1-C6 alkyl optionally substituted by 1-2 R$_{11}$; or —COR$_{12}$; or NR$_1$R$_2$ represents N=CR$_{21}$NR$_{22}$R$_{23}$, N=CR$_{24}$OR$_{25}$; or

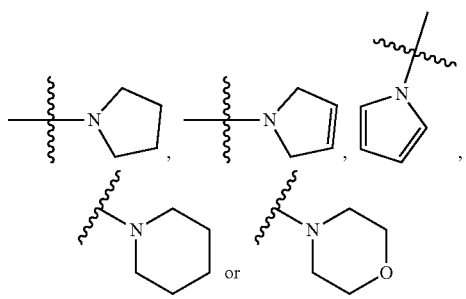

that is unsubstituted or substituted by 1-2 groups independently selected from the group consisting of halogen, C1-C6 alkyl, C1-C6 alkoxy, halo C1-C6 alkoxy, C1-C6 alkylthio, halo C1-C6 alkylthio, amino, C1-C6 alkylamino, di-C1-C6 alkylamino and C1-C6 alkoxycarbonyl;

wherein $R_{11}$ independently represents halogen, hydroxy, C1-C6 alkoxy, halo C1-C6 alkoxy, C1-C6 alkylthio, halo C1-C6 alkylthio, amino, C1-C6 alkylamino, di-C1-C6 alkylamino, C1-C6 alkoxycarbonyl; or phenyl, naphthyl,

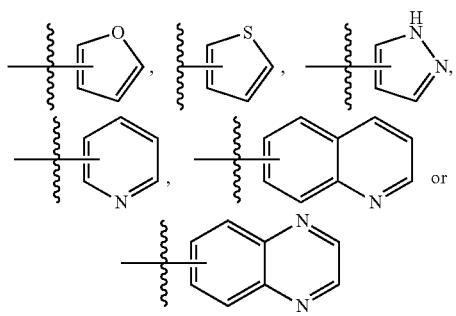

is unsubstituted or substituted by 1-3 groups selected from the group consisting of halogen, C1-C6 alkyl, halo C1-C6 alkyl, C1-C6 alkoxy and nitro;

$R_{12}$ represents H, C1-C14 alkyl, halo C1-C6 alkyl, C1-C6 alkoxy, phenyl, phenoxy or benzyloxy;

$R_{13}$ represents H, C1-C6 alkyl, halo C1-C6 alkyl, phenyl, benzyl or $CHR_{31}C(O)OR_{32}$; $R_{31}$ represents H, C1-C6 alkyl or C1-C6 alkoxy; $R_{32}$ represents H, C1-C6 alkyl or benzyl;

$R_{14}$ represents C1-C6 alkyl or halo C1-C6 alkyl;

$R_{15}$ represents H, C1-C6 alkyl, formyl, C1-C6 alkylacyl, halo C1-C6 alkylacyl, C1-C6 alkoxycarbonyl, phenylcarbonyl, phenoxycarbonyl or benzyloxycarbonyl; $R_{16}$ represents H or C1-C6 alkyl;

$R_{17}$ represents H, C1-C6 alkyl; or phenyl that is unsubstituted or substituted by 1-3 groups selected from the group consisting of halogen, C1-C6 alkyl and C1-C6 alkoxy; $R_{18}$ represents H or C1-C6 alkyl; or $N=CR_{17}R_{18}$ represents

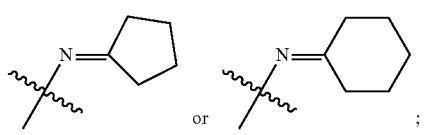

$R_{21}$, $R_{24}$ each independently represent H or C1-C6 alkyl;

$R_{22}$, $R_{23}$ each independently represent H or C1-C6 alkyl; or $NR_{22}R_{23}$ represents

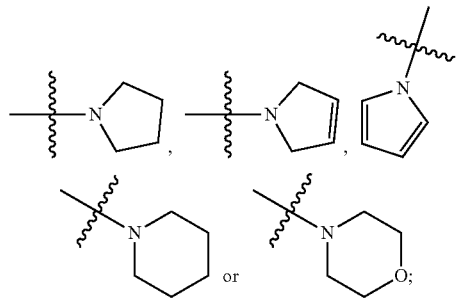

$R_{25}$ represents C1-C6 alkyl;

the term "heterocyclyl" refers to

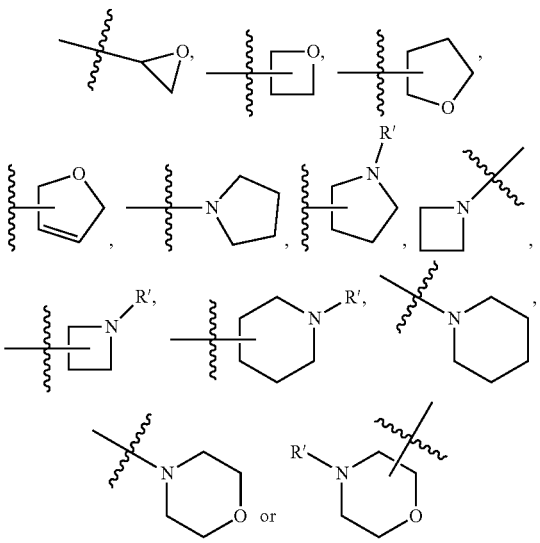

with 0, 1 or 2 oxo groups; the term "aryl" refers to phenyl or naphthyl; the term "heteroaryl" refers to

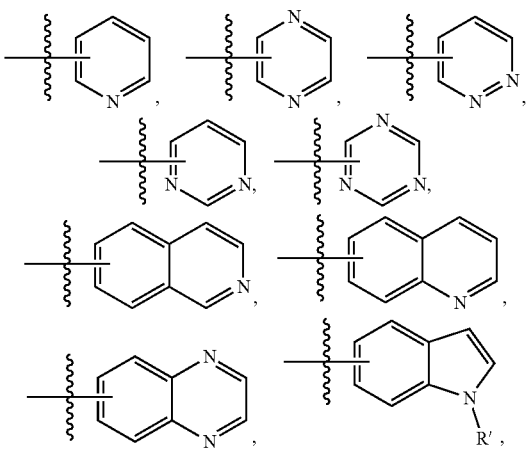

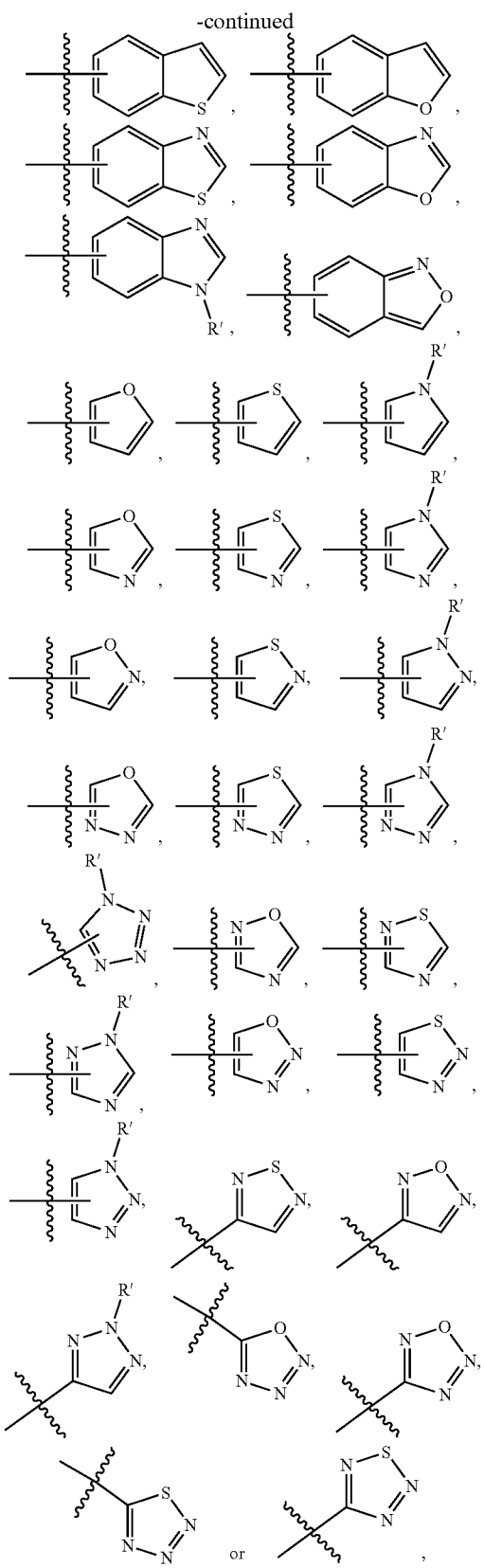

which is substituted by 0, 1, 2 or 3 groups selected from the group consisting of halogen, nitro, cyano, thiocyano, hydroxy, carboxy, mercapto, formyl; phenyl, benzyl, benzyloxy, phenoxy that is unsubstituted or substituted by at least one group from the group consisting of halogen, C1-C6 alkyl and C1-C6 alkoxy; C1-C6 alkyl, C2-C6 alkenyl, C2-C6 alkynyl, C3-C6 cycloalkyl, C3-C6 cycloalkyl C1-C6 alkyl, OR", SR", —(C1-C6)alkyl-OR", —(C1-C6)alkyl-SR", COR", COOR", COSR", SOR", SO₂R", OCOR" or SCOR" with or without halogen; and amino or aminocarbonyl substituted by one or two groups selected from the group consisting of hydrogen, C1-C6 alkyl, C2-C6 alkenyl, C2-C6 alkynyl, C3-C6 cycloalkyl, C3-C6 cycloalkyl C1-C6 alkyl, phenyl, benzyl, benzyloxy, phenoxy, COR", COOR", SO₂R" and OR";

R' each independently represents hydrogen, nitro, hydroxy, amino; or C1-C6 alkyl, C2-C6 alkenyl, C2-C6 alkynyl, C3-C6 cycloalkyl, C3-C6 cyclo alkenyl, C3-C6 cycloalkyl C1-C6 alkyl, C1-C6 alkoxy, C2-C6 alkenyloxy, C2-C6 alkynyloxy, C3-C6 cycloalkyloxy, C1-C6 alkoxy C1-C6 alkyl, C1-C6 alkoxycarbonyl, C1-C6 alkylthiocarbonyl, C1-C6 alkylsulfonyl, C1-C6 alkylsulfonyl C1-C6 alkyl, C1-C6 alkylcarbonyl, C1-C6 alkylcarbonyl C1-C6 alkyl, C1-C6 alkylacyloxy, C1-C6 alkylamino, C1-C6 alkylaminocarbonyl, C1-C6 alkoxyaminocarbonyl, C1-C6 alkoxycarbonyl C1-C6 alkyl, C1-C6 alkylaminocarbonyl C1-C6 alkyl, tri-C1-C6 alkylsilyl or di-C1-C6 alkylphosphono with or without fluoro, chloro or bromo;

R" each independently represents hydrogen, C1-C6 alkyl, C2-C6 alkenyl, C2-C6 alkynyl, C3-C6 cycloalkyl or C3-C6 cycloalkyl C1-C6 alkyl.

Further preferably, A, B each independently represent halogen, C1-C6 alkyl, halo C1-C6 alkyl or C3-C6 cycloalkyl;

C represents hydrogen, halogen, C1-C6 alkyl or halo C1-C6 alkyl;

Q represents C1-C6 alkyl, halo C1-C6 alkyl, C3-C6 cycloalkyl, C2-C6 alkenyl, C2-C6 alkynyl, halogen, cyano, amino, nitro, formyl, C1-C6 alkoxy, C1-C6 alkylthio, C1-C6 alkoxycarbonyl, hydroxy C1-C6 alkyl, C1-C6 alkoxy C1-C2 alkyl, cyano C1-C2 alkyl, C1-C6 alkylamino C1-C2 alkyl, benzyl, naphthyl, furyl, thienyl, thiazolyl, pyridyl, pyrimidinyl;

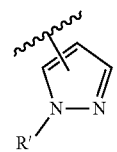

that is unsubstituted or substituted by C1-C6 alkyl; or phenyl that is unsubstituted or substituted by at least one group selected from the group consisting of C1-C6 alkyl, halo C1-C6 alkyl, halogen and C1-C6 alkoxy;

M represents —(C1-C6)alkyl-R, -halo(C1-C6)alkyl-R or

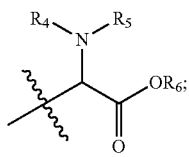

R represents

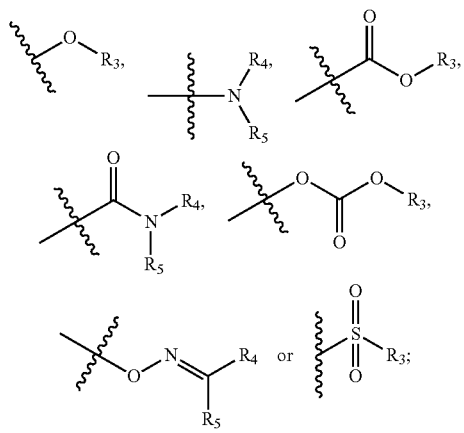

$R_3$ each independently represents hydrogen, C1-C6 alkyl, C2-C6 alkenyl, C2-C6 alkynyl, C3-C6 cycloalkyl, C3-C6 cycloalkyl C1-C6 alkyl; or phenyl, naphthyl, benzyl,

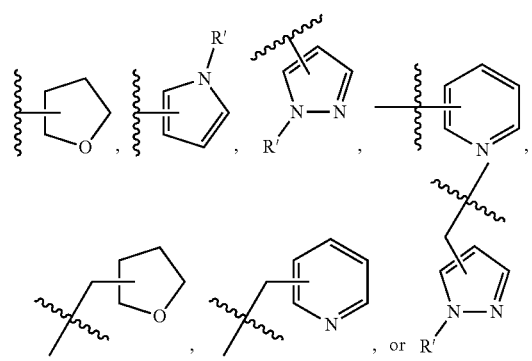

that is unsubstituted or substituted by at least one group selected from the group consisting of C1-C6 alkyl, C1-C6 alkoxy, halogen and halo C1-C6 alkyl;

$R_4$, $R_5$, and $R_6$ each independently represent hydrogen, C1-C6 alkyl, C2-C6 alkenyl, C2-C6 alkynyl, C3-C6 cycloalkyl, C3-C6 cycloalkyl C1-C6 alkyl, C1-C6 alkoxy, C1-C6 alkoxycarbonyl; or phenyl, naphthyl, benzyl,

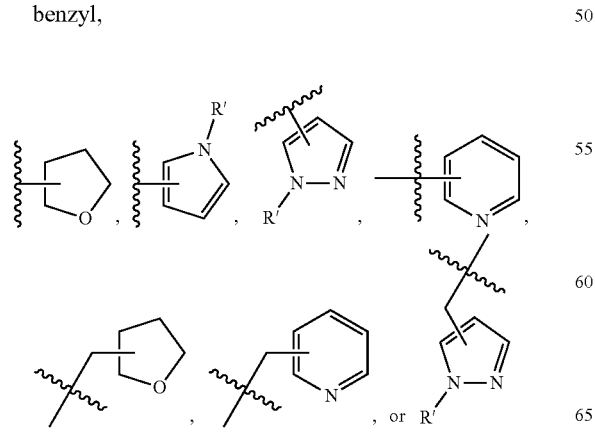

that is unsubstituted or substituted by at least one group selected from the group consisting of C1-C6 alkyl, C1-C6 alkoxy, halogen and halo C1-C6 alkyl;

R' represents C1-C6 alkyl or halo C1-C6 alkyl;

X represents amino, C1-C6 alkylamino, C1-C6 alkylcarbonylamino, phenylcarbonylamino, benzylamino; or furylmethyleneamino that is unsubstituted or substituted by halo C1-C6 alkyl.

More further preferably, A, B each independently represent fluoro, chloro, bromo, iodo, methyl, ethyl, propyl, isopropyl, trifluoromethyl or cyclopropyl;

C represents hydrogen, fluoro, chloro, bromo, iodo, methyl or trifluoromethyl;

Q represents methyl, ethyl, propyl, isopropyl, cyclopropyl, vinyl, ethynyl, fluoro, chloro, bromo, cyano, amino, nitro, formyl, methoxy, methylthio, methoxycarbonyl, monochloromethyl, monofluoromethyl, difluoromethyl, trifluoromethyl, 2-chloroethyl, 2,2,2-trifluoroethyl, hydroxymethyl,

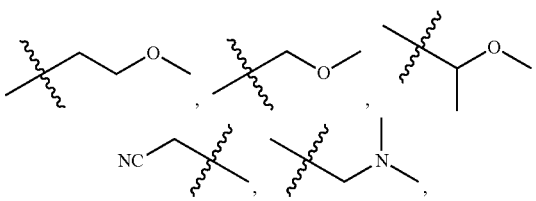

benzyl, naphthyl, furyl, thienyl, thiazolyl, pyridyl, pyrimidinyl;

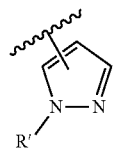

that is unsubstituted or substituted by methyl; or phenyl that is unsubstituted or substituted by at least one group selected from the group consisting of methyl, trifluoromethyl, chloro and methoxy;

R' represents methyl, ethyl or difluoromethyl;

M represents

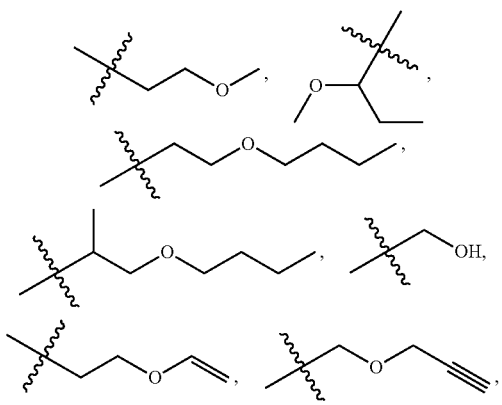

-continued
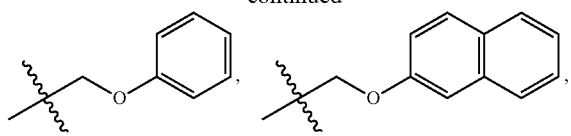
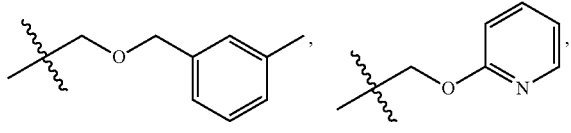
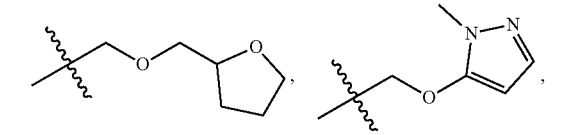
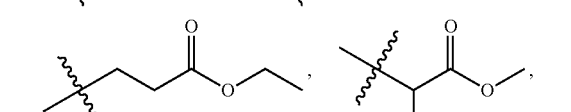
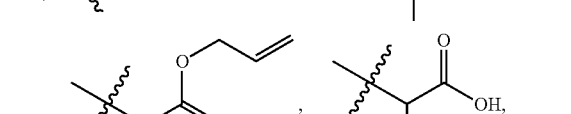
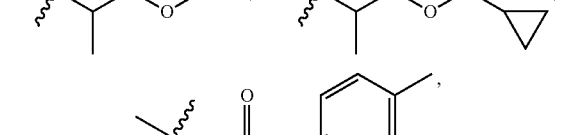
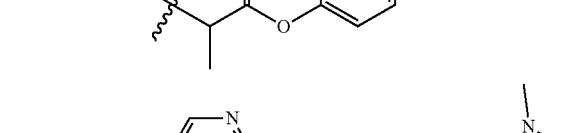
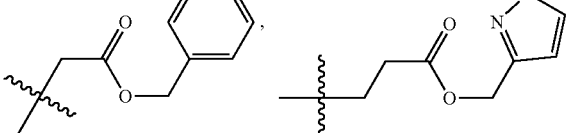
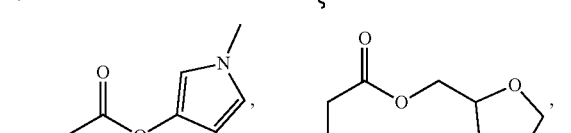
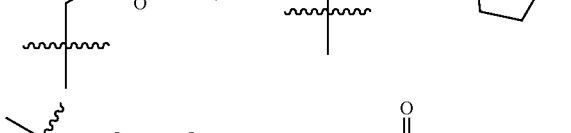
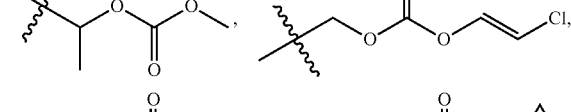
-continued
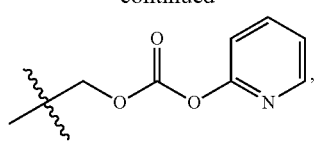
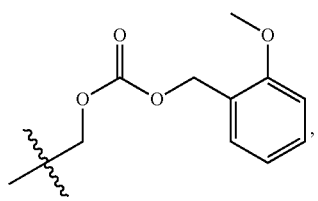
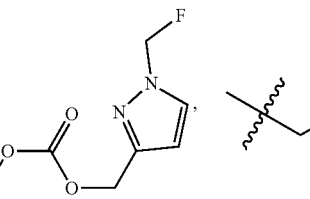
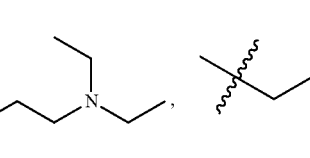
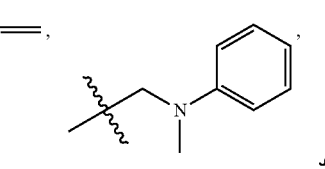
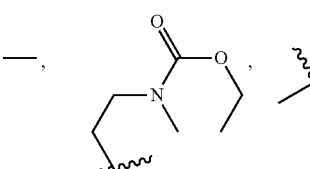
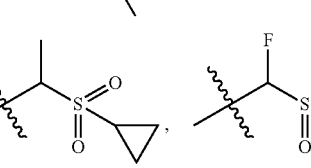
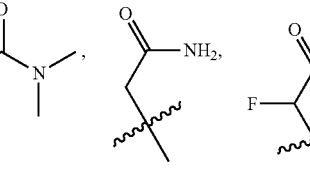
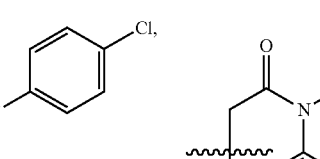

-continued

X represents NH$_2$,

In the definition of the compound represented by the above general formula I and in all the structural formula below, the term, whether used alone or in a compound name, refers to the following substituent: an alkyl group having more than two carbon atoms may be straight or branched. For example, in the compound name "-alkyl-OR"", alkyl may be —CH$_2$—, —CH$_2$CH$_2$—, —CH(CH$_3$)—, —C(CH$_3$)$_2$— and the like. The alkyl group is, for example, methyl; ethyl; n-propyl or isopropyl; n-butyl, isobutyl, tert-butyl or 2-butyl; pentyl; hexyl such as n-hexyl, isohexyl or 1,3-dimethylbutyl. Halogen is fluorine, chlorine, bromine or iodine.

If a group is substituted by a group, it is understood to mean that the group is substituted by one or more identical or different groups selected from those mentioned above.

Further, the same or different substitution characters contained in the same or different substituents are independently selected, and may be the same or different.

Depending on the property of substituents and the linkage manner thereof, the compound of Formula I may exist as a stereoisomer. For example, if a compound has one or more asymmetric carbon atoms, it may has enantiomers and diastereomers. The stereoisomer can be obtained from the mixtures obtained in the preparation by conventional separation methods, for example by chromatographic separation. The stereoisomer may also be prepared selectively by using stereoselective reactions and using optically active starting materials and/or auxiliaries. The present invention also relates to all stereoisomers and mixtures thereof which are included in the general Formula I but are not specifically defined.

The preparation method of the pyridyloxy carboxylate derivative comprises the following steps:

A compound of formula III is reacted with a compound of formula II to obtain a compound of formula I; the reaction scheme is as follows:

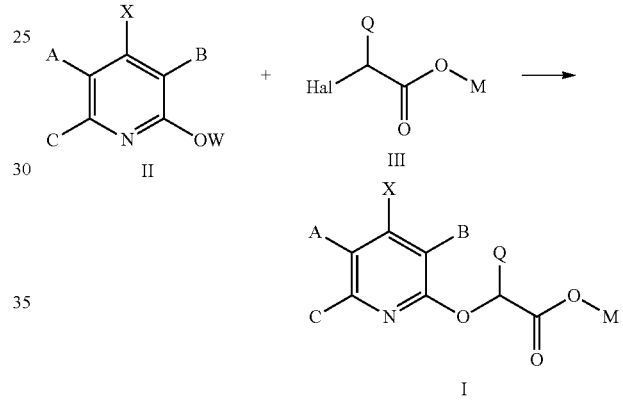

wherein, W represents an alkali metal, preferably K, Na; Hal represents halogen, preferably Br, Cl; the reaction is carried out in the presence of a catalyst and a solvent. Preferably, the catalyst is TBAB, and the solvent is one or more selected from the group consisting of DCM, DCE, ACN, THF and DMF.

or, when X represents NR$_1$R$_2$(R$_1$, R$_2$ are not hydrogen at the same time), it is obtained by reacting a compound of formula I-1

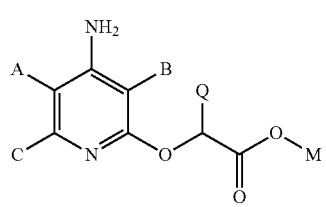

with a corresponding halide;

wherein, the halide is preferably chloride or bromide; the reaction is carried out in the presence of a base and a solvent, wherein the base is one or more selected from the group consisting of sodium hydroxide, potassium hydroxide, sodium carbonate, potassium carbonate, sodium bicarbonate and cesium carbonate; the solvent is one or more selected from the group consisting of THF, 1,4-dioxane, toluene, 1,2-dichloroethane, ethyl acetate, acetonitrile, DMF, acetone, dichloromethane and chloroform; a catalyst, preferably DMAP, is optionally added during the reaction.

A herbicidal composition comprising (i) at least one of pyridyloxy carboxylate derivatives of the formula I; preferably, further comprising (ii) one or more further herbicides and/or safeners; more preferably, further comprising (iii) agrochemically acceptable formulation auxiliaries.

A method for controlling a weed comprising applying a herbicidally effective amount of at least one of the pyridyloxy carboxylate derivatives or the herbicidal composition on a plant or in a weed area. Preferably, the plant is rice (such as japonica rice, indica rice), soybean; or the weed is a gramineous weed (such as *Echinochloa crusgalli*, *Digitaria sanguinalis*), a broad-leaved weed (such as *Monochoria Vaginalis*, *Abutilon theophrasti*, *Galium spurium*) or a cyperaceae weed (such as *Cyperus iria*).

Use of at least one of the pyridyloxy carboxylate derivatives or the herbicidal composition for controlling a weed, preferably, the pyridyloxy carboxylate derivative being used to control a weed in a useful crop, wherein the useful crop is a genetically modified crop or a crop treated by gene editing technology. Preferably, the plant is rice (such as japonica rice, indica rice), soybean, or the weed is a gramineous weed (such as *Echinochloa crusgalli*, *Digitaria sanguinalis*), a broad-leaved weed (such as *Monochoria Vaginalis*, *Abutilon theophrasti*, *Galium spurium*) or a cyperaceae weed (such as *Cyperus iria*).

The compounds of the formula I according to the invention have an outstanding herbicidal activity against a broad spectrum of economically important monocotyledonous and dicotyledonous harmful plants. The active compounds also act efficiently on perennial weeds which produce shoots from rhizomes, root stocks or other perennial organs and which are difficult to control. In this context, it is generally immaterial whether the substances are applied pre-sowing, pre-emergence or post-emergence. Specifically, examples may be mentioned of some representatives of the monocotyledonous and dicotyledonous weed flora which can be controlled by the compounds according to the invention, without these being a restriction to certain species. Examples of weed species on which the active compounds act efficiently are, from amongst the monocotyledons, *Avena, Lolium, Alopecurus, Phalaris, Echinochloa, Digitaria, Setaria* and also *Cyperus* species from the annual sector and from amongst the perennial species *Agropyron, Cynodon, Imperata* and *Sorghum*, and also perennial *Cyperus* species.

In the case of the dicotyledonous weed species, the spectrum of action extends to species such as, for example, *Galium, Viola, Veronica, Lamium, Stellaria, Amaranthus, Sinapis, Ipomoea, Sida, Matricaria* and *Abutilon* from amongst the annuals, and *Convolvulus, Cirsium, Rumex* and *Artemisia* in the case of the perennial weeds. The active compounds according to the invention also effect outstanding control of harmful plants which occur under the specific conditions of rice growing such as, for example, *Echinochloa, Sagittaria, Alisma, Eleocharis, Scirpus* and *Cyperus*. If the compounds according to the invention are applied to the soil surface prior to germination, then the weed seedlings are either prevented completely from emerging, or the weeds grow until they have reached the cotyledon stage but then their growth stops, and, eventually, after three to four weeks have elapsed, they die completely. In particular, the compounds according to the invention exhibit excellent activity against *Apera spica venti, Chenopodium album, Lamium purpureum, Polygonum convulvulus, Stellaria media, Veronica* hederifolia, *Veronica persica, Viola* tricolor and against *Amaranthus, Galium* and *Kochia* species.

Although the compounds according to the invention have an excellent herbicidal activity against monocotyledonous and dicotyledonous weeds, crop plants of economically important crops such as, for example, wheat, barley, rye, rice, corn, sugarbeet, cotton and soya, are not damaged at all, or only to a negligible extent. In particular, they have excellent compatibility in cereals, such as wheat, barley and corn, in particular wheat. For these reasons, the present compounds are highly suitable for selectively controlling undesired plant growth in plantings for agricultural use or in plantings of ornamentals.

Owing to their herbicidal properties, these active compounds can also be employed for controlling harmful plants in crops of known or still to be developed genetically engineered plants. The transgenic plants generally have particularly advantageous properties, for example resistance to certain pesticides, in particular certain herbicides, resistance to plant diseases or causative organisms of plant diseases, such as certain insects or microorganisms such as fungi, bacteria or viruses. Other particular properties relate, for example, to the quantity, quality, storage-stability, composition and to specific ingredients of the harvested product. Thus, transgenic plants having an increased starch content or a modified quality of the starch or those having a different fatty acid composition of the harvested produce are known.

The use of the compounds of the formula I according to the invention in economically important transgenic crops of useful and ornamental plants, for example of cereal, such as wheat, barley, rye, oats, millet, rice, maniok and corn, or else in crops of sugarbeet, cotton, soya, rapeseed, potato, tomato, pea and other vegetable species is preferred. The compounds of the formula I can preferably be used as herbicides in crops of useful plants which are resistant or which have been made resistant by genetic engineering toward the phytotoxic effects of the herbicides.

Conventional ways for preparing novel plants which have modified properties compared to known plants comprise, for example, traditional breeding methods and the generation of mutants. Alternatively, novel plants having modified properties can be generated with the aid of genetic engineering methods (see, for example, EP-A 0 221 044, EP-A 0 131 624). For example, there have been described several cases of genetically engineered changes in crop plants in order to modify the starch synthesized in the plants (for example WO 92/11376, WO 92/14827, WO 91/19806), transgenic crop plants which are resistant to certain herbicides of the glufosinate (Glufosinate ammonium)—(cf., for example, EP-A 0 242 236, EP-A 0 242 246) or glyphosate-type (WO 92/00377), or of the sulfonylurea-type (EP-A 0 257 993, U.S. Pat. No. 5,013,659 A), transgenic crop plants, for example cotton, having the ability to produce *Bacillus thuringiensis* toxins (Bt toxins) which impart resistance to certain pests to the plants (EP-A 0 142 924, EP-A 0 193 259), transgenic crop plants having a modified fatty acid composition (WO 91/13972).

Numerous molecular biological techniques which allow the preparation of novel transgenic plants having modified properties are known in principle; see, for example, Sambrook et al., 1989, Molecular Cloning, A Laboratory Manual, 2nd ed. Cold Spring Harbor Laboratory Press, Cold Spring Harbor, N. Y.; or Winnacker "Gene und Klone"

[Genes and Clones], VCH Weinheim, 2nd edition 1996, or Christou, "Trends in Plant Science" 1 (1996) 423-431). In order to carry out such genetic engineering manipulations, it is possible to introduce nucleic acid molecules into plasmids which allow a mutagenesis or a change in the sequence to occur by recombination of DNA sequences. Using the abovementioned standard processes it is possible, for example, to exchange bases, to remove partial sequences or to add natural or synthetic sequences. To link the DNA fragments with each other, it is possible to attach adaptors or linkers to the fragments.

Plant cells having a reduced activity of a gene product can be prepared, for example, by expressing at least one appropriate antisense-RNA, a sense-RNA to achieve a cosuppression effect, or by expressing at least one appropriately constructed ribozyme which specifically cleaves transcripts of the abovementioned gene product.

To this end it is possible to employ both DNA molecules which comprise the entire coding sequence of a gene product including any flanking sequences that may be present, and DNA molecules which comprise only parts of the coding sequence, it being necessary for these parts to be long enough to cause an antisense effect in the cells. It is also possible to use DNA sequences which have a high degree of homology to the coding sequences of a gene product but which are not entirely identical.

When expressing nucleic acid molecules in plants, the synthesized protein can be localized in any desired compartment of the plant cells. However, to achieve localization in a certain compartment, it is, for example, possible to link the coding region with DNA sequences which ensure localization in a certain compartment. Such sequences are known to the person skilled in the art (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106).

The transgenic plant cells can be regenerated to whole plants using known techniques. The transgenic plants can in principle be plants of any desired plant species, i. e. both monocotyledonous and dicotyledonous plants. In this manner, it is possible to obtain transgenic plants which have modified properties by overexpression, suppression or inhibition of homologous (=natural) genes or gene sequences or by expression of heterologous (=foreign) genes or gene sequences.

When using the active compounds according to the invention in transgenic crops, in addition to the effects against harmful plants which can be observed in other crops, there are frequently effects which are specific for the application in the respective transgenic crop, for example a modified or specifically broadened spectrum of weeds which can be controlled, modified application rates which can be used for the application, preferably good combinability with the herbicides to which the transgenic crops are resistant, and an effect on the growth and the yield of the transgenic crop plants. The invention therefore also provides for the use of the compounds according to the invention as herbicides for controlling harmful plants in transgenic crop plants.

In addition, the substances according to the invention have outstanding growth-regulating properties in crop plants. They engage in the plant metabolism in a regulating manner and can this be employed for the targeted control of plant constituents and for facilitating harvesting, for example by provoking desiccation and stunted growth. Furthermore, they are also suitable for generally regulating and inhibiting undesirable vegetative growth, without destroying the plants in the process. Inhibition of vegetative growth plays an important role in many monocotyledon and dicotyledon crops because lodging can be reduced hereby, or prevented completely.

The compounds according to the invention can be applied in the customary formulations in the form of wettable powders, emulsifiable concentrates, sprayable solutions, dusts or granules. The invention therefore also provides herbicidal compositions comprising compounds of the formula I. The compounds of the formula I can be formulated in various ways depending on the prevailing biological and/or chemico-physical parameters. Examples of suitable formulation options are: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), oil dispersions (OD), oil- or water-based dispersions, oil-miscible solutions, dusts (DP), capsule suspensions (CS), seed-dressing compositions, granules for broadcasting and soil application, granules (GR) in the form of microgranules, spray granules, coating granules and adsorption granules, water-dispersible granules (WG), water-soluble granules (SG), ULV formulations, microcapsules and waxes. These individual formulation types are known in principle and are described, for example, in Winnacker-Küchler, "Chemische Technologie" [Chemical Technology], Volume 7, C. Hauser Verlag Munich, 4th. Edition 1986; Wade van Valkenburg, "Pesticide Formulations", Marcel Dekker, N. Y., 1973; K. Martens, "Spray Drying" Handbook, 3rd Ed. 1979, G. Goodwin Ltd. London.

The necessary formulation auxiliaries, such as inert materials, surfactants, solvents and other additives, are likewise known and are described, for example, in Watkins, "Handbook of Insecticide Dust Diluents and Carriers", 2nd Ed., Darland Books, Caldwell N. J., H. v. Olphen, "Introduction to Clay Colloid Chemistry"; 2nd Ed., J. Wiley & Sons, N. Y.; C. Marsden, "Solvents Guide"; 2nd Ed., Interscience, N. Y. 1963; McCutcheon's "Detergents and Emulsifiers Annual", MC Publ. Corp., Ridgewood N. J.; Sisley and Wood, "Encyclopedia of Surface Active Agents", Chem. Publ. Co. Inc., N. Y. 1964; Schönfeldt, "Grenzflüchenaktive Äthylenoxidaddkte" [Surface-active ethylene oxide adducts], Wiss. Verlagagesell. Stuttgart 1976; Winnacker-Küchler, "Chemische Technologie" [Chemical Technology], Volume 7, C. Hauser Verlag Munich, 4th Edition 1986.

Wettable powders are preparations which are uniformly dispersible in water and which contain, in addition to the active compound and as well as a diluent or inert substance, surfactants of ionic and/or nonionic type (wetting agents, dispersants), for example polyethoxylated alkyl phenols, polyethoxylated fatty alcohols, polyethoxylated fatty amines, fatty alcohol polyglycol ethersulfates, alkanesulfonates, alkylbenzenesulfonates, sodium ligninsulfonate, sodium 2,2'-dinaphthylmethane-6,6'-disulfonate, sodium dibutyinaphthalenesulfona-te or else sodium oleoylmethyltaurinate. To prepare the wettable powders, the herbicidally active compounds are finely ground, for example in customary apparatus such as hammer mills, fan mills and air-jet mills, and are mixed simultaneously or subsequently with the formulation auxiliaries.

Emulsifiable concentrates are prepared by dissolving the active compound in an organic solvent, for example butanol, cyclohexanone, dimethylformamide, xylene or else relatively high-boiling aromatic compounds or hydrocarbons or mixtures of the solvents, with the addition of one or more surfactants of ionic and/or nonionic type (emulsifiers). Examples of emulsifiers which can be used are calcium alkylarylsulfonates, such as Ca dodecylbenzenesulfonate, or nonionic emulsifiers, such as fatty acid polyglycol esters, alkylaryl polyglycol ethers, fatty alcohol polyglycol ethers, propylene oxide-ethylene oxide condensation products, alkyl polyethers, sorbitan esters, for example sorbitan fatty acid esters or polyoxyethylene sorbitan esters, for example polyoxyethylene sorbitan fatty acid esters.

Dusts are obtained by grinding the active compound with finely divided solid substances, for example talc, natural clays, such as kaolin, bentonite and pyrophyllite, or diatomaceous earth. Suspension concentrates can be water- or oil-based. They can be prepared, for example, by wet milling using commercially customary bead mills, with or without the addition of surfactants as already mentioned above, for example, in the case of the other formulation types.

Emulsions, for example oil-in-water emulsions (EW), can be prepared for example by means of stirrers, colloid mills and/or static mixers using aqueous organic solvents and, if desired, surfactants as already mentioned above, for example, in the case of the other formulation types.

Granules can be prepared either by spraying the active compound onto adsorptive, granulated inert material or by applying active-compound concentrates to the surface of carriers such as sand, kaolinites or granulated inert material, by means of adhesive binders, for example polyvinyl alcohol, sodium polyacrylate or else mineral oils. Suitable active compounds can also be granulated in the manner which is customary for the preparation of fertilizer granules, if desired as a mixture with fertilizers. Water-dispersible granules are generally prepared by the customary processes, such as spray-drying, fluidized-bed granulation, disk granulation, mixing using high-speed mixers, and extrusion without solid inert material.

For the preparation of disk, fluidized-bed, extruder and spray granules, see for example processes in "Spray-Drying Handbook" 3rd ed. 1979, G. Goodwin Ltd., London; J. E. Browning, "Agglomeration", Chemical and Engineering 1967, pages 147 ff.; "Perry's Chemical Engineer's Handbook", 5th Ed., McGraw-Hill, New York 1973, pp. 8-57. For further details on the formulation of crop protection products, see for example G. C. Klingman, "Weed Control as a Science", John Wiley and Sons Inc., New York, 1961, pages 81-96 and J. D. Freyer, S. A. Evans, "Weed Control Handbook", 5th Ed., Blackwell Scientific Publications, Oxford, 1968, pages 101-103.

The agrochemical formulations generally contain from 0.1 to 99% by weight, in particular from 0.1 to 95% by weight, of active compound of the formula I. In wettable powders the concentration of active compound is, for example, from about 10 to 99% by weight, the remainder to 100% by weight consisting of customary formulation constituents. In emulsifiable concentrates the concentration of active compound can be from about 1 to 90%, preferably from 5 to 80%, by weight. Formulations in the form of dusts contain from 1 to 30% by weight of active compound, preferably most commonly from 5 to 20% by weight of active compound, while sprayable solutions contain from about 0.05 to 80%, preferably from 2 to 50%, by weight of active compound. In the case of water-dispersible granules the content of active compound depends partly on whether the active compound is in liquid or solid form and on the granulation auxiliaries, fillers, etc. that are used. In water-dispersible granules the content of active compound, for example, is between 1 and 95% by weight, preferably between 10 and 80% by weight.

In addition, said formulations of active compound may comprise the tackifiers, wetting agents, dispersants, emulsifiers, penetrants, preservatives, antifreeze agents, solvents, fillers, carriers, colorants, antifoams, evaporation inhibitors and pH and viscosity regulators which are customary in each case.

Based on these formulations it is also possible to produce combinations with other pesticidally active substances, for example insecticides, acaricides, herbicides and fungicides, and also with safeners, fertilizers and/or growth regulators, for example in the form of a ready-mix or tank mix.

Suitable active compounds which can be combined with the active compounds according to the invention in mixed formulations or in a tank mix are, for example, known active compounds as described in for example *World Herbicide New Product Technology Handbook*, China Agricultural Science and Farming Techniques Press, 2010. 9 and in the literature cited therein. For example the following active compounds may be mentioned as herbicides which can be combined with the compounds of the formula I (note: the compounds are either named by the "common name" in accordance with the International Organization for Standardization (ISO) or by the chemical names, if appropriate together with a customary code number): acetochlor, butachlor, alachlor, propisochlor, metolachlor, s-metolachlor, pretilachlor, propachlor, ethachlor, napropamide, R-left handed napropamide, propanil, mefenacet, diphenamid, diflufenican, ethaprochlor, beflubutamid, bromobutide, dimethenamid, dimethenamid-P, etobenzanid, flufenacet, thenylchlor, metazachlor, isoxaben, flamprop-M-methyl, flamprop-M-propyl, allidochlor, pethoxamid, chloranocryl, cyprazine, mefluidide, monalide, delachlor, prynachlor, terbuchlor, xylachlor, dimethachlor, cisanilide, trimexachlor, clomeprop, propyzamide, pentanochlor, carbetamide, benzoylprop-ethyl, cyprazole, butenachlor, tebutam, benzipram, mogrton, dichlofluanid, naproanilide, diethatyl-ethyl, naptalam, flufenacet, benzadox, chlorthiamid, chlorophthalimide, isocarbamide, picolinafen, atrazine, simazine, prometryn, cyanatryn, simetryn, ametryn, propazine, dipropetryn, SSH-108, terbutryn, terbuthylazine, triaziflam, cyprazine, proglinazine, trietazine, prometon, simetone, aziprotryne, desmetryn, dimethametryn, procyazine, mesoprazine, sebuthylazine, secbumeton, terbumeton, methoprotryne, cyanatryn, ipazine, chlorazine, atraton, pendimethalin, eglinazine, cyanuric acid, indaziflam, chlorsulfuron, metsulfuron-methyl, bensulfuron methyl, chlorimuron-ethyl, tribenuron-methyl, thifensulfuron-methyl, pyrazosulfuron-ethyl, mesosulfuron, iodosulfuron-methyl sodium, foramsulfuron, cinosulfuron, triasulfuron, sulfometuron methyl, nicosulfuron, ethametsulfuron-methyl, amidosulfuron, ethoxysulfuron, cyclosulfamuron, rimsulfuron, azimsulfuron, flazasulfuron, monosulfuron, monosulfuron-ester, flucarbazone-sodium, flupyrsulfuron-methyl, halosulfuron-methyl, oxasulfuron, imazosulfuron, primisulfuron, propoxycarbazone, prosulfuron, sulfosulfuron, trifloxysulfuron, triflusulfuron-methyl, tritosulfuron, sodium metsulfuron methyl, flucetosulfuron, HNPC-C, orthosulfamuron, propyrisulfuron, metazosulfuron, acifluorfen, fomesafen, lactofen, fluoroglycofen, oxyfluorfen, chlornitrofen, aclonifen, ethoxyfen-ethyl, bifenox, nitrofluorfen, chlomethoxyfen, fluorodifen, fluoronitrofen, furyloxyfen, nitrofen, TOPE, DMNP, PPG1013, AKH-7088, halosafen, chlortoluron, isoproturon, linuron, diuron, dymron, fluometuron, benzthiazuron, methabenzthiazuron, cumyluron, ethidimuron, isouron, tebuthiuron, buturon, chlorbromuron, methyldymron, phenobenzuron, SK-85, metobromuron, metoxuron, afesin, monuron, siduron, fenuron, fluothiuron, neburon, chloroxuron, noruron, isonoruron, 3-cyclooctyl-1, thiazfluron, tebuthiuron, difenoxuron, parafluron, methylamine tribunil, karbutilate, trimeturon, dimefuron, monisouron, anisuron, methiuron, chloreturon, tetrafluron, phenmedipham, phenmedipham-ethyl, desmedipham, asulam, terbucarb, barban, propham, chlorpropham, rowmate, swep, chlorbufam, carboxazole, chlorprocarb, fenasulam, BCPC, CPPC, carbasulam, butylate, benthiocarb, vernolate, molinate, triallate, dimepiperate, esprocarb, pyributicarb, cycloate, avadex, EPTC, ethiolate, orbencarb, pebulate, prosulfocarb, tiocarbazil, CDEC, dimexano, isopolinate, methiobencarb, 2,4-D butyl ester, MCPA-Na, 2,4-D isooctyl ester, MCPA isooctyl ester, 2,4-D sodium salt, 2,4-D dimethyla mine salt, MCPA-thioethyl, MCPA, 2,4-D propionic acid, high 2,4-D propionic acid salt, 2,4-D butyric acid, MCPA propionic acid, MCPA propionic acid salt, MCPA butyric acid, 2,4,5-D, 2,4,5-D propionic acid, 2,4,5-D butyric acid, MCPA amine salt, dicamba, erbon, chlorfenac, saison, TBA, chloramben, methoxy-TBA, diclofop-methyl, fluazifop-butyl, fluazifop-p-butyl, haloxyfop-methyl, haloxyfop-P, quizalofop-ethyl, quizalofop-p-ethyl, fenoxaprop-ethy, fenoxaprop-p-ethyl, propaquizafop, cyhalofop-butyl, metamifop, clodinafop-propargyl, fenthiaprop-ethyl, chloroazifop-propynyl, poppenate-methyl, trifopsime, isoxapyrifop, paraquat, diquat, oryzalin, ethalfluralin, isopropalin, nitralin, profluralin, prodinamine, benfluralin, fluchloraline, dinitramina, dipropalin, chlornidine, methalpropalin, dinoprop, glyphosate, anilofos, glufosinate ammonium, amiprophos-methyl, sulphosate, piperophos, bialaphos-sodium, bensulide, butamifos, phocarb, 2,4-DEP, H-9201, zytron, imazapyr, imazethapyr, imazaquin, imazamox, imazamox ammonium salt, imazapic, imazamethabenz-methyl, fluroxypyr, fluroxypyr isooctyl ester, clopyralid, picloram, trichlopyr, dithiopyr, haloxydine, 3,5,6-trichloro-2-pyridinol, thiazopyr, fluridone, aminopyralid, diflufenzopyr, triclopyr-butotyl, Cliodinate, sethoxydim, clethodim, cycloxydim, alloxydim, clefoxydim, butroxydim, tralkoxydim, tepraloxydim, buthidazole, metribuzin, hexazinone, metamitron, ethiozin, ametridione, amibuzin, bromoxynil, bromoxynil octanoate, ioxynil octanoate, ioxynil, dichlobenil, diphenatrile, pyraclonil, chloroxynil, iodobonil, flumetsulam, florasulam, penoxsulam, metosulam, cloransulam-methyl, diclosulam, pyroxsulam, benfuresate, bispyribac-sodium, pyribenzoxim, pyriftalid, pyriminobac-methyl, pyrithiobac-sodium, benzobicylon, mesotrione, sulcotrione, tembotrione, tefuryltrione, bicyclopyrone, ketodpiradox, isoxaflutole, clomazone, fenoxasulfone, methiozolin, fluazolate, pyraflufen-ethyl, pyrazolynate, difenzoquat, pyrazoxyfen, benzofenap, nipyraclofen, pyrasulfotole, topramezone, pyroxasulfone, cafenstrole, flupoxam, aminotriazole, amicarbazone, azafenidin, carfentrazone-ethyl, sulfentrazone, bencarbazone, benzfendizone, butafenacil, bromacil, isocil, lenacil, terbacil, flupropacil, cinidon-ethyl, flumiclorac-pentyl, flumioxazin, propyzamide, MK-129, flumezin, pentachlorophenol, dinoseb, dinoterb, dinoterb acetate, dinosam, DNOC, chloronitrophene, medinoterb acetate, dinofenate, oxadiargyl, oxadiazon, pentoxazone, Flufenacet, fluthiacet-methyl, fentrazamide, flufenpyr-ethyl, pyrazon, brompyrazon, metflurazon, kusakira, dimidazon, oxapyrazon, norflurazon, pyridafol, quinclorac, quinmerac, bentazone, pyridate, oxaziclomefone, benazolin, clomazone, cinmethylin, ZJ0702, pyribambenz-propyl, indanofan, sodium chlorate, dalapon, trichloroacetic acid, monochloroacetic acid, hexachloroacetone, flupropanate, cyperquat, bromofenoxim, epronaz, methazole, flurtamone, benfuresate, ethofumesate, tioclorim, chlorthal, fluorochlridone, tavron, acrolein, bentranil, tridiphane, chlorfenpropmethyl, thidiarizonaimin, phenisopham, busoxinone, methoxyphenone, saflufenacil, clacyfos, chloropon, alorac, diethamquat, etnipromid, iprymidam, ipfencarbazone, thiencarbazone-methyl, pyrimisulfan, chlorflurazole, tripropindan, sulglycapin, prosulfalin, cambendichlor, aminocyclopyrachlor, rodethanil, benoxacor, fenclorim, flurazole, fenchlorazole-ethyl, cloquintocet-mexyl, oxabetrinil, MG/91, cyometrinil, DKA-24, mefenpyr-diethyl, furilazole, fluxofenim, isoxadifen-ethyl, dichlormid, halauxifen-methyl, DOW florpyrauxifen, UBH-509, D489, LS 82-556, KPP-300, NC-324, NC-330, KH-218, DPX-N8189, SC-0744, DOWCO535, DK-8910, V-53482, PP-600, MBH-001, KIH-9201, ET-751, KIH-6127 and KIH-2023.

In the context of the present specification, if an abbreviation of a generic name of an active compound is used, it includes in each case all customary derivatives, such as esters and salts, as well as isomers, in particular optical isomers, especially one or more commercially available forms. If the generic name denotes an ester or a salt, it also includes in each case all other conventional derivatives, such as other esters and salts, free acids and neutral compounds, as well as isomers, in particular optical isomers, especially one or more commercially available forms. The chemical name given to a compound means at least one compound encompassed by the generic name, and generally the preferred compound.

For use, the formulations which are present in commercially available form are, if appropriate, diluted in the customary manner, for example using water in the case of wettable powders, emulsifiable concentrates, dispersions and water-dispersible granules. Products in the form of dusts, granules for soil application or broadcasting and sprayable solutions are usually not further diluted with other inert substances prior to use. The application rate of the compounds of the formula I required varies with the external conditions, such as temperature, humidity, the nature of the herbicide used and the like. It can vary within wide limits, for example between 0.001 and 1.0 kg/ha or more of active substance, but it is preferably between 0.005 and 750 g/ha, in particular between 0.005 and 500 g/ha.

SPECIFIC MODE FOR CARRYING OUT THE INVENTION

The following examples are intended to illustrate the present invention and should not be construed as limiting the present invention in any way. The scope for which protection is sought in the present invention is intended to be defined by the claims.

In view of economics and variety of a compound, we preferably synthesized several compounds, part of which are listed in the following Table 1. The structure and information of a certain compound are shown in Tables 1-2. The compounds in Table 1 are listed for further explication of the present invention, other than any limit therefor. The subject of the present invention should not be interpreted by those skilled in the art as being limited to the following compounds.

TABLE 1

The structure of compounds

| No. | A | B | C | Q | M | X |
|---|---|---|---|---|---|---|
| 1 | F | F | F | CH₃ | methyl ester CH₂C(O)OCH₃ | NH₂ |
| 2 | Cl | Cl | Cl | CH₃ | methyl ester CH₂C(O)OCH₃ | NH₂ |
| 3 | Cl | Cl | H | CH₃ | CH₂CH₂OCH₃ | NH₂ |
| 4 | Cl | Cl | F | CH₃ | methyl ester CH₂C(O)OCH₃ | NH₂ |
| 5 | Cl | Cl | CH₃ | CH₃ | CH₂CH₂ON=C(CH₃)₂ | NH₂ |
| 6 | Cl | Cl | CF₃ | CH₃ | methyl ester CH₂C(O)OCH₃ | NH₂ |
| 7 | CH₃ | CH₃ | F | CH₃ | CH₂CH₂N(Et)₂ | NH₂ |
| 8 | Et | Et | CF₃ | CH₃ | ethyl ester CH₂CH₂C(O)OEt | NH₂ |
| 9 | iPr | Cl | H | CH₃ | ethyl ester CH₂CH₂C(O)OEt | NH₂ |
| 10 | cyclopropyl | Cl | Cl | CH₃ | methyl ester CH₂C(O)OCH₃ | NH₂ |
| 11 | F | iPr | CF₃ | CH₃ | CH₂CH₂OCH₃ | NH₂ |

TABLE 1-continued

The structure of compounds

| No. | A | B | C | Q | M | X |
|-----|---|---|---|---|---|---|
| 12 | Br | Br | F | CH₃ | -CH₂-O-N=C(CH₃)- | NH₂ |
| 13 | I | I | H | CH₃ | -CH₂CH₂-C(=O)-O-CH₂CH₃ | NH₂ |
| 14 | -CH₂CH₂CH₃ | -cyclopropyl | F | CH₃ | -CH₂-C(=O)-O-CH₃ | NH₂ |
| 15 | CF₃ | Cl | F | CH₃ | -CH₂CH₂-N(CH₂CH₃)₂ | NH₂ |
| 16 | Cl | CF₃ | H | CH₃ | -CH₂-C(=O)-O-CH₃ | NH₂ |
| 17 | Cl | Cl | I | CH₃ | -CH₂CH₂-O-CH₃ | NH₂ |
| 18 | Cl | -CH₂CH₂CH₃ | Br | CH₃ | -CH₂CH₂-C(=O)-O-CH₂CH₃ | NH₂ |
| 19 | CH₃ | CH₃ | CH₃ | CH₃ | -CH₂CH₂-C(=O)-O-CH₂CH₃ | NH₂ |
| 20 | Cl | CH₃ | F | CH₃ | -CH₂CH₂-O-N=C(CH₃)- | NH₂ |
| 21 | Cl | CH₃ | H | CH₃ | -CH₂-C(=O)-O-CH₃ | NH₂ |
| 22 | Cl | -cyclopropyl | F | CH₃ | -CH₂CH₂-O-CH₃ | NH₂ |

TABLE 1-continued

The structure of compounds

| No. | A | B | C | Q | M | X |
|---|---|---|---|---|---|---|
| 23 | Cl | Cl | H | CH₃ | (allyl pivalate group) | NH₂ |
| 24 | Cl | Cl | Cl | CH₃ | (ethyl propanoate group) | NH₂ |
| 25 | Cl | Cl | F | Et | (ethyl propanoate group) | NH₂ |
| 26 | Cl | Cl | F | (n-propyl) | (methoxyethyl group) | NH₂ |
| 27 | Cl | Cl | F | (isopropyl) | (methyl acetate group) | NH₂ |
| 28 | Cl | Cl | F | (cyclopropyl) | (methoxyethyl group) | NH₂ |
| 29 | Cl | Cl | F | (methoxyethyl) | (O-N=C(CH₃) oxime group) | NH₂ |
| 30 | Cl | Cl | F | (methoxymethyl) | (methyl acetate group) | NH₂ |
| 31 | Cl | Cl | F | (1-methoxyethyl) | (methyl 2-methylpropanoate group) | NH₂ |
| 32 | Cl | Cl | F | (allyl) | (methyl 2,2-dimethylpropanoate group) | NH₂ |
| 33 | Cl | Cl | F | (ethynyl) | (N,N-dimethylpropanamide group) | NH₂ |

TABLE 1-continued
The structure of compounds
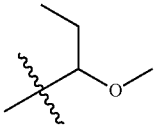 [SMILES: *C(CC)OC]
| No. | A | B | C | Q | M | X |
|---|---|---|---|---|---|---|
| 34 | Cl | Cl | F | F | 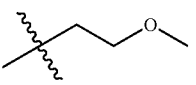 [SMILES: *CCOC] | NH$_2$ |
| 35 | Cl | Cl | F | Cl | 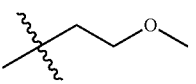 [SMILES: *CCOC] | NH$_2$ |
| 36 | Cl | Cl | F | Br | 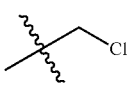 | NH$_2$ |
| 37 | Cl | Cl | F | 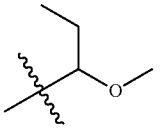 | 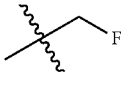 | NH$_2$ |
| 38 | Cl | Cl | F | 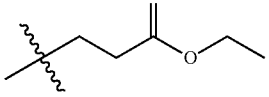 | 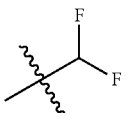 | NH$_2$ |
| 39 | Cl | Cl | F | 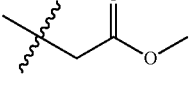 | 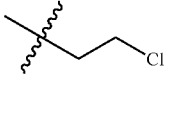 [SMILES: *CCCl] | NH$_2$ |
| 40 | Cl | Cl | F | 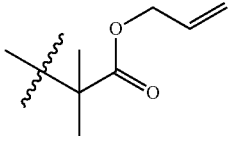 [SMILES: *C(C)(C)C(=O)OCC=C] | 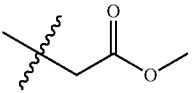 [SMILES: *CC(=O)OC] | NH$_2$ |
| 41 | Cl | Cl | F | CF$_3$ | 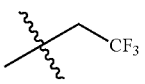 | NH$_2$ |
| 42 | Cl | Cl | F | 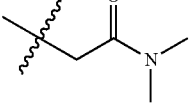 | 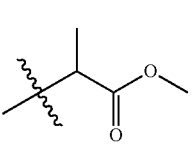 [SMILES: *C(C)C(=O)OC] | NH$_2$ |
| 43 | Cl | Cl | F | CN |  | NH$_2$ |

TABLE 1-continued

The structure of compounds

| No. | A | B | C | Q | M | X |
|-----|---|---|---|---|---|---|
| 44 | Cl | Cl | F | NC-CH₂-C(CH₃)< (cyanomethyl with methyl) | -CH(CH₃)CH₂C(=O)OCH₃ | NH₂ |
| 45 | Cl | Cl | F | NH₂ | -CH(CH₃)CH₂C(=O)OCH₃ | NH₂ |
| 46 | Cl | Cl | F | -C(CH₃)(CH₂N(CH₃)₂)- | -CH(CH₃)CH₂N(CH₃)₂ | NH |
| 47 | Cl | Cl | F | -C(CH₃)(SCH₃)- | -CH(CH₃)CH₂OCH₃ | NH₂ |
| 48 | Cl | Cl | F | -C(CH₃)(CH₂OH)- | -CH(CH₃)CH₂C(=O)OCH₃ | NH₂ |
| 49 | Cl | Cl | F | NO₂ | -CH(CH₃)CH₂OCH₃ | NH₂ |
| 50 | Cl | Cl | F | -C(CH₃)(OCH₃)- | -C(CH₃)₂C(=O)OCH₂CH=CH₂ | NH₂ |
| 51 | Cl | Cl | F | -C(CH₃)(CHO)- | -CH(CH₃)CH₂C(=O)OCH₂CH₃ | NH₂ |
| 52 | Cl | Cl | F | -C(CH₃)(C(=O)OCH₃)- | -CH(CH₃)CH₂N(CH₃)₂ | NH₂ |
| 53 | Cl | Cl | F | -CH₂C₆H₅ | -CH(CH₃)CH₂C(=O)OCH₃ | NH₂ |
| 54 | Cl | Cl | F | -CH(2-thienyl)- | -CH(CH₃)OC(=O)OCH₃ | NH₂ |

TABLE 1-continued
The structure of compounds
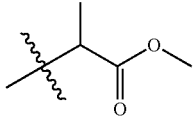
| No. | A | B | C | Q | M | X |
|---|---|---|---|---|---|---|
| 55 | Cl | Cl | F | 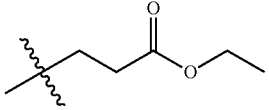 [SMILES: *CCC(=O)OCC] | 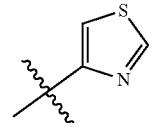 [SMILES: *c1cscn1] | $NH_2$ |
| 56 | Cl | Cl | F | 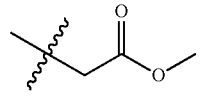 [SMILES: *CC(=O)OC] | 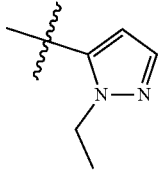 [SMILES: *c1ccnn1CC] | $NH_2$ |
| 57 | Cl | Cl | F | 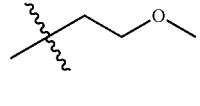 [SMILES: *CCOC] | 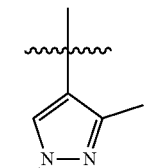 | $NH_2$ |
| 58 | Cl | Cl | F | 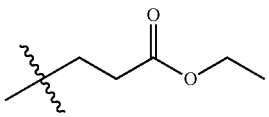 [SMILES: *CCC(=O)OCC] | 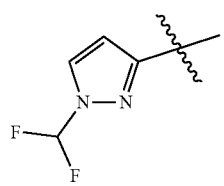 [SMILES: *c1ccn(C(F)F)n1] | $NH_2$ |
| 59 | Cl | Cl | F | 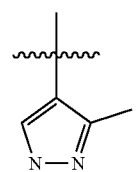 | 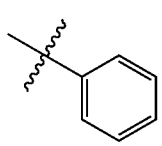 [SMILES: *c1ccccc1] | $NH_2$ |
| 60 | Cl | Cl | F | 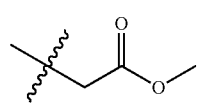 [SMILES: *CC(=O)OC] | 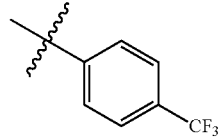 | $NH_2$ |
| 61 | Cl | Cl | F | 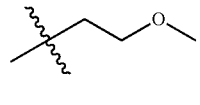 [SMILES: *CCOC] | 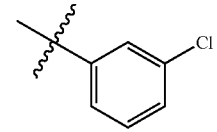 [SMILES: *c1cccc(Cl)c1] | $NH_2$ |
| 62 | Cl | Cl | F | 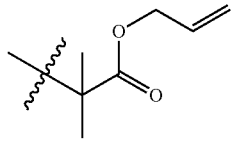 [SMILES: *C(C)(C)C(=O)OCC=C] | | $NH_2$ |

TABLE 1-continued

The structure of compounds

| No. | A | B | C | Q | M | X |
|---|---|---|---|---|---|---|
| 63 | Cl | Cl | F | 2-methyl-4-methoxyphenyl | methyl acetate | NH$_2$ |
| 64 | Cl | Cl | F | pyridin-3-yl | methoxyethyl | NH$_2$ |
| 65 | Cl | Cl | F | pyrimidin-5-yl | methyl acetate | NH$_2$ |
| 66 | Cl | Cl | F | naphthalen-2-yl | methyl carbonate (CH(CH$_3$)OC(O)OCH$_3$) | NH$_2$ |
| 67 | Cl | Cl | F | CH$_3$ | CH(Et)OCH$_3$ | NH$_2$ |
| 68 | Cl | Cl | F | CH$_3$ | CH(CH$_3$)CH$_2$OCH$_3$ | NH$_2$ |
| 69 | Cl | Cl | F | CH$_3$ | CH$_2$CH$_2$CH$_2$OCH$_2$CH$_2$CH$_3$ | NH$_2$ |
| 70 | Cl | Cl | F | CH$_3$ | CH(CH$_3$)CH$_2$N(Et)$_2$ | NH$_2$ |
| 71 | Cl | Cl | F | CH$_3$ | CH(CH$_3$)CH$_2$C(O)OEt | NH$_2$ |
| 72 | Cl | Cl | F | CH$_3$ | CH(CH$_3$)CH(CH$_3$)C(O)OCH$_3$ | NH$_2$ |

TABLE 1-continued

The structure of compounds

![structure]

| No. | A | B | C | Q | M | X |
|---|---|---|---|---|---|---|
| 73 | Cl | Cl | F | CH$_3$ | ethyl ester group | NH$_2$ |
| 74 | Cl | Cl | F | CH$_3$ | allyl dimethyl ester group | NH$_2$ |
| 75 | Cl | Cl | F | CH$_3$ | N,N-dimethyl amide group | NH$_2$ |
| 76 | Cl | Cl | F | CH$_3$ | methyl carbonate group | NH$_2$ |
| 77 | Cl | Cl | F | CH$_3$ | α-amino acid group | NH$_2$ |
| 78 | Cl | Cl | F | CH$_3$ | Boc-NH methyl ester group | NH$_2$ |
| 79 | Cl | Cl | F | CH$_3$ | O-N=C(CH$_3$) group | NH$_2$ |
| 80 | Cl | Cl | F | CH$_3$ | methylsulfonyl group | NH$_2$ |
| 81 | Cl | Cl | F | CH$_3$ | hydroxymethyl group | NH$_2$ |
| 82 | Cl | Cl | F | CH$_3$ | vinyl ether group | NH$_2$ |

TABLE 1-continued
The structure of compounds
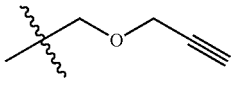 [SMILES: *COCC#C]
| No. | A | B | C | Q | M | X |
|---|---|---|---|---|---|---|
| 83 | Cl | Cl | F | CH₃ | 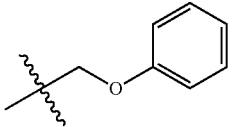 [SMILES: *COc1ccccc1] | NH₂ |
| 84 | Cl | Cl | F | CH₃ | 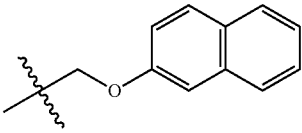 [SMILES: *COc1ccc2ccccc2c1] | NH₂ |
| 85 | Cl | Cl | F | CH₃ | 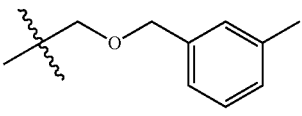 [SMILES: *COCc1cccc(C)c1] | NH₂ |
| 86 | Cl | Cl | F | CH₃ | 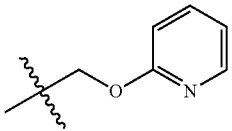 [SMILES: *COc1ccccn1] | NH₂ |
| 87 | Cl | Cl | F | CH₃ | 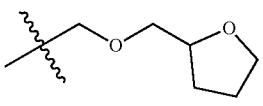 [SMILES: *COCC1CCCO1] | NH₂ |
| 88 | Cl | Cl | F | CH₃ | 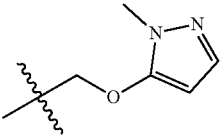 [SMILES: *COc1ccnn1C] | NH₂ |
| 89 | Cl | Cl | F | CH₃ | 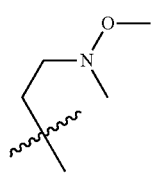 [SMILES: *CCN(C)OC] | NH₂ |
| 90 | Cl | Cl | F | CH₃ | 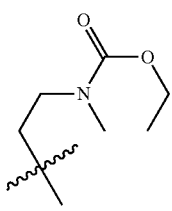 | NH₂ |
| 91 | Cl | Cl | F | CH₃ |  | NH₂ |

TABLE 1-continued

The structure of compounds

| No. | A | B | C | Q | M | X |
|---|---|---|---|---|---|---|
| 92 | Cl | Cl | F | CH₃ | (N-vinyl-N-methylaminoethyl with methyl branch) | NH₂ |
| 93 | Cl | Cl | F | CH₃ | (N-phenyl-N-methylaminoethyl with methyl branch) | NH₂ |
| 94 | Cl | Cl | F | CH₃ | (N-ethynylaminoethyl with methyl branch) | NH₂ |
| 95 | Cl | Cl | F | CH₃ | (cyclopropylsulfonyl ethyl with methyl branch) | NH₂ |
| 96 | Cl | Cl | F | CH₃ | (fluoro(methylsulfonyl)methyl ethyl with methyl branch) | NH₂ |
| 97 | Cl | Cl | F | CH₃ | (O-N=C(CH₃)(OCH₃) oxime ether with methyl branch) | NH₂ |
| 98 | Cl | Cl | F | CH₃ | (O-N=C(CH₃)(CH₂Cl) oxime ether with methyl branch) | NH₂ |
| 99 | Cl | Cl | F | CH₃ | (O-N=C(CH₃)(phenyl) oxime ether with methyl branch) | NH₂ |

TABLE 1-continued

The structure of compounds

| No. | A | B | C | Q | M | X |
|-----|---|---|---|---|---|---|
| 100 | Cl | Cl | F | CH₃ | (O-N=C(CH₂CF₃)-CH=CH₂ group) | NH₂ |
| 101 | Cl | Cl | F | CH₃ | (N(Et)C(O)OMe-CH-C(O)OMe group) | NH₂ |
| 102 | Cl | Cl | F | CH₃ | (NHMe-CH-C(O)O-CH(Cl)-CH=CH₂ group) | NH₂ |
| 103 | Cl | Cl | F | CH₃ | (NH₂-CH-C(O)O-iPr group) | NH₂ |
| 104 | Cl | Cl | F | CH₃ | (NH₂-CH-C(O)O-CH₂-(3-CF₃-C₆H₄) group) | NH₂ |
| 105 | Cl | Cl | F | CH₃ | (CH₂-C(O)OH group) | NH₂ |
| 106 | Cl | Cl | F | CH₃ | (CH(CH₃)-C(O)O-C≡CH group) | NH₂ |
| 107 | Cl | Cl | F | CH₃ | (CH₂-C(O)O-CH₂-cyclopropyl group) | NH₂ |

TABLE 1-continued

The structure of compounds

| No. | A | B | C | Q | M | X |
|-----|---|---|---|---|---|---|
| 108 | Cl | Cl | F | CH₃ | (4-methylphenyl acetate group) | NH₂ |
| 109 | Cl | Cl | F | CH₃ | (pyridin-4-ylmethyl acetate group) | NH₂ |
| 110 | Cl | Cl | F | CH₃ | ((1-methyl-1H-pyrazol-3-yl)methyl acetate group) | NH₂ |
| 111 | Cl | Cl | F | CH₃ | (1-methyl-1H-pyrrol-3-yl propanoate group) | NH₂ |
| 112 | Cl | Cl | F | CH₃ | ((tetrahydrofuran-2-yl)methyl propanoate group) | NH₂ |
| 113 | Cl | Cl | F | CH₃ | (3-methylbutanamide group) | NH₂ |
| 114 | Cl | Cl | F | CH₃ | (N-(4-chlorophenyl)-N-methyl pentanamide group) | NH₂ |

TABLE 1-continued

The structure of compounds

| No. | A | B | C | Q | M | X |
|---|---|---|---|---|---|---|
| 115 | Cl | Cl | F | CH₃ | (N-vinyl-N-methyl-2-fluoro-2-methylpropanamide group) | NH₂ |
| 116 | Cl | Cl | F | CH₃ | (N,N-diphenylacetamide with methyl branch) | NH₂ |
| 117 | Cl | Cl | F | CH₃ | (2-chlorovinyl carbonate group) | NH₂ |
| 118 | Cl | Cl | F | CH₃ | (ethynyl carbonate group) | NH₂ |
| 119 | Cl | Cl | F | CH₃ | (cyclopropyl carbonate group) | NH₂ |
| 120 | Cl | Cl | F | CH₃ | (pyridin-2-yl carbonate group) | NH₂ |
| 121 | Cl | Cl | F | CH₃ | (2-methoxybenzyl carbonate group) | NH₂ |

TABLE 1-continued

The structure of compounds

| No. | A | B | C | Q | M | X |
|-----|---|---|---|---|---|---|
| 122 | Cl | Cl | F | CH₃ | (CH₂F-pyrazolyl-CH₂-O-C(=O)-CH₂-C(CH₃)₂-) | NH₂ |
| 123 | Cl | Cl | F | CH₃ | -C(CH₃)₂-CH₂-O-CH₂CH₂CH₂CH₃ | -NH-CH₃ |
| 124 | Cl | Cl | F | CH₃ | -C(CH₃)₂-CH₂-N(CH₃)₂ | -NH-CH₂CH₃ |
| 125 | Cl | Cl | F | CH₃ | -C(CH₃)₂-CH₂-C(=O)-O-CH₂CH₃ | -CH(CH₃)-NH-C(=O)-CH₃ |
| 126 | Cl | Cl | F | CH₃ | -C(CH₃)₂-CH₂-C(=O)-O-CH₃ | -NH-CH₂-(2-furyl) |
| 127 | Cl | Cl | F | CH₃ | -C(CH₃)₂-CH₂-C(=O)-N(CH₃)₂ | -NH-C(=O)-Ph |
| 128 | Cl | Cl | F | CH₃ | -C(CH₃)₂-C(=O)-O-CH₂-CH=CH₂ | -NH-CH₂-Ph |
| 129 | Cl | Cl | F | CH₃ | -C(CH₃)₂-CH₂-NH₂ | NH₂ |
| 130 | Cl | Cl | F | CH₃ | -C(CH₃)₂-CH₂-N(CH₃)₂ | NH₂ |

TABLE 1-continued

The structure of compounds

| No. | A | B | C | Q | M | X |
|---|---|---|---|---|---|---|
| 131 | Cl | Cl | F | CH₃ | (branched CH with CH₂-O-butyl) | NH₂ |
| 132 | Cl | Cl | F | CH₃ | (CH₂CH₂-O-N=C(CH₃)₂) | HN-CH₂-(furan-CF₃) |

TABLE 2

¹HNMR data of compounds

| No. | ¹HNMR |
|---|---|
| 1 | ¹H NMR (500 MHz, Chloroform-d) δ 4.57 (q, J = 8.0 Hz, 1H), 4.40 (s, 2H), 3.69 (s, 3H), 3.50 (s, 2H), 1.72 (d, J = 8.0 Hz, 3H). |
| 2 | ¹H NMR (500 MHz, Chloroform-d) δ 4.59 (q, J = 8.0 Hz, 1H), 4.33 (s, 2H), 3.68 (s, 3H), 3.48 (s, 2H), 1.71 (d, J = 8.0 Hz, 3H). |
| 3 | ¹H NMR (500 MHz, Chloroform-d) δ 7.56 (s, 1H), 4.65 (q, J = 6.5 Hz, 1H), 4.45 (s, 2H), 4.17-4.04 (m, 2H), 3.60-3.50 (m, 1H), 3.37-3.25 (m, 4H), 1.61 (d, J = 6.5 Hz, 3H). |
| 4 | ¹H NMR (500 MHz, Chloroform-d) δ 5.32 (d, J = 12.0 Hz, 1H), 4.57 (q, J = 6.5 Hz, 1H), 4.45 (s, 2H), 4.39 (d, J = 12.0 Hz, 1H), 3.69 (s, 3H), 1.72 (d, J = 6.5 Hz, 3H). |
| 5 | ¹H NMR (500 MHz, Chloroform-d) δ 4.60-4.48 (m, 2H), 4.45 (s, 2H), 4.11- 3.83 (m, 2H), 3.57-3.43 (m, 1H), 2.65 (s, 3H), 2.59 (s, 6H), 1.67 (d, J = 6.5 Hz, 3H). |
| 6 | ¹H NMR (500 MHz, Chloroform-d) δ 5.43 (d, J = 12.0 Hz, 1H), 4.72 (q, J = 6.5 Hz, 1H), 4.51 (s, 2H), 4.24 (d, J = 12.0 Hz, 1H), 3.66 (s, 3H), 1.63 (d, J = 6.0 Hz, 3H). |
| 7 | ¹H NMR (500 MHz, Chloroform-d) δ 4.74-4.58 (m, 2H), 4.00-3.89 (m, 1H), 3.50 (s, 2H), 3.06-2.95 (m, 2H), 2.71-2.62 (m, 1H), 2.17 (d, J = 7.5 Hz, 6H), 2.01-1.87 (m, 2H), 1.90-1.82 (m, 2H), 1.64 (d, J = 6.8 Hz, 3H), 1.54-1.40 (m, 2H), 1.03 (t, J = 8.0 Hz, 3H), 0.92 (t, J = 8.0 Hz, 3H). |
| 8 | ¹H NMR (500 MHz, Chloroform-d) δ 4.69-4.55 (m, 3H), 4.04-3.81 (m, 2H), 3.50 (s, 2H), 2.88-2.46 (m, 2H), 2.41-2.22 (m, 4H), 1.59 (d, J = 6.8 Hz, 3H), 1.20-1.12 (m, 9H). |
| 9 | ¹H NMR (500 MHz, Chloroform-d) δ 7.43 (s, 1H), 4.77-4.64 (m, 2H), 4.61 (q, J = 6.5 Hz, 1H), 4.41-4.30 (m, 1H), 3.93-3.82 (m, 1H), 3.50 (s, 2H), 3.02-2.90 (m, 1H), 2.58-2.40 (m, 1H), 2.31-2.21 (m, 1H), 1.61 (d, J = 6.5 Hz, 3H), 1.30-1.17 (m, 9H). |
| 10 | ¹H NMR (500 MHz, Chloroform-d) δ 5.28 (d, J = 12.0 Hz, 1H), 4.64 (q, J = 6.8 Hz, 1H), 4.21 (d, J = 12.3 Hz, 1H), 3.69 (s, 3H), 3.50 (s, 2H), 1.63 (dd, J = 6.9, 5.3 Hz, 4H), 0.97-0.72 (m, 4H). |
| 11 | ¹H NMR (500 MHz, Chloroform-d) δ 4.13-4.02 (m, 1H), 3.74-3.59 (m, 1H), 3.50 (s, 1H), 3.39-3.25 (m, 2H), 1.66 (d, J = 6.8 Hz, 2H), 1.26 (dd, J = 24.9, 6.8 Hz, 3H). |
| 12 | ¹H NMR (500 MHz, Chloroform-d) δ 4.75-4.68 (m, 2H), 4.01-3.89 (m, 1H), 3.50 (s, 2H), 3.44-3.35 (m, 2H), 2.59 (s, 6H), 1.64 (d, J = 6.5 Hz, 3H). |
| 13 | ¹H NMR (500 MHz, Chloroform-d) δ 8.11 (s, 1H), 5.31-5.24 (m, 1H), 4.75-4.59 (m, 2H), 3.85-3.77 (m, 1H), 3.50 (s, 2H), 3.35-3.23 (m, 1H), 2.61-2.55 (m, 1H), 1.74-1.67 (m, 1H), 1.63 (d, J = 6.5 Hz, 3H), 1.17 (t, J = 8.0 Hz, 3H). |
| 14 | ¹H NMR (500 MHz, Chloroform-d) δ 5.23 (d, J = 12.5 Hz, 1H), 4.64 (q, J = 6.5 Hz, 1H), 4.38 (d, J = 12.0 Hz, 1H), 3.70 (s, 3H), 3.50 (s, 2H), 2.60 (t, J = 7.5 Hz, 2H), 1.83-1.70 (m, 2H), 1.66 (d, J = 6.5 Hz, 3H), 1.60 (q, J = 7.0 Hz, 1H), 1.02-0.93 (m, 5H), 0.77-0.68 (m, 2H). |
| 15 | ¹H NMR (500 MHz, Chloroform-d) δ 5.00-4.89 (m, 1H), 4.72 (q, J = 6.5 Hz, 1H), 3.95-8.89(m, 1H), 3.50 (s, 2H), 3.37- 3.14 (m, 3H), 2.24-2.17 (m, 1H), 1.79-1.62 (m, 5H), 1.09 (t, J = 8.0 Hz, 6H). |
| 16 | ¹H NMR(500 MHz, Chloroform-d) δ 7.69 (s, 1H), 5.32 (d, J = 12.2 Hz, 1H), 4.58 (q, J = 6.8 Hz, 1H), 4.38 (d, J = 12.5 Hz, 1H), 3.68 (s, 3H), 3.50 (s, 2H), 1.69 (d, J = 6.8 Hz, 3H). |
| 17 | ¹H NMR (500 MHz, Chloroform-d) δ 4.64 (q, J = 6.5 Hz, 1H), 4.44 (s, 2H), 4.20-4.11 (m, 2H), 3.58-3.44 (m, 1H), 3.39-3.28 (m, 4H), 1.61 (d, J = 6.5 Hz, 3H). |
| 18 | ¹H NMR (500 MHz, Chloroform-d) δ 5.12-5.03 (m, 1H), 4.65 (q, J = 6.5 Hz, 1H), 4.56-4.39 (m, 2H), 3.92-3.81 (m, 1H), 3.50 (s, 2H), 2.53-2.40 (m, 1H), 2.37-2.26 (m, 2H), 2.22-2.11 (m, 1H), 1.75-1.50 (m, 5H), 1.17 (t, J = 8.0 Hz, 3H). |
| 19 | ¹H NMR (500 MHz, Chloroform-d) δ 4.53 (s, 2H), 4.36 (q, J = 8.0 Hz, 2H), 2.64 (s, 3H), 2.52 (s, 3H), 2.19-2.09 (m, 6H), 1.63 (d, J = 6.5 Hz, 3H), 1.17 (t, J = 8.0 Hz, 3H). |
| 20 | ¹H NMR (500 MHz, Chloroform-d) δ 4.57 (s, 2H), 3.74-3.50 (m, 4H), 2.58 (s, 6H), 2.19 (s, 3H), 1.66 (d, J = 6.5 Hz, 3H). |

TABLE 2-continued

¹HNMR data of compounds

| No. | ¹HNMR |
|---|---|
| 21 | ¹H NMR (500 MHz, Chloroform-d) δ 7.54 (s, 1H), 5.29 (d, J = 12.5 Hz, 1H), 4.69 (q, J = 6.5 Hz, 1H), 4.30 (d, J = 12.0 Hz, 1H), 3.66 (s, 3H), 3.50 (s, 2H), 2.21 (s, 3H), 1.61 (d, J = 6.5 Hz, 3H). |
| 22 | ¹H NMR (500 MHz, Chloroform-d) δ 4.55 (s, 2H), 3.66-3.55 (m, 2H), 3.57-3.47 (m, 1H), 3.50 (s, 2H), 3.37 (s, 3H), 1.67 (d, J = 6.8 Hz, 3H), 1.58-1.03 (m, 3 H), 0.79-0.70 (m, 2H). |
| 23 | ¹H NMR (500 MHz, Chloroform-d) δ 7.53 (s, 1H), 5.94-5.82 (m, 1H), 5.21-5.11 (m, 2H), 4.75-4.59 (m, 2H), 4.44 (s, 2H), 1.66 (s, 6H). |
| 24 | ¹H NMR (500 MHz, Chloroform-d) δ 4.99-4.67 (m, 2H), 4.50 (s, 2H), 4.32-4.20 (m, 2H), 4.07-3.89 (m, 1H), 2.47-2.34 (m, 1H), 2.06-1.99 (m, 1H), 1.67 (d, J = 6.8 Hz, 3H), 1.17 (t, J = 8.0 Hz, 3H). |
| 25 | ¹H NMR (500 MHz, Chloroform-d) δ 5.03-4.93 (m, 2H), 4.43 (s, 2H), 4.32-4.20 (m, 2H), 4.05-3.98 (m, 1H), 2.68-2.41 (m, 2H), 2.06 -1.84 (m, 2H), 1.17 (t, J = 8.0 Hz, 3H), 0.97 (t, J = 8.0 Hz, 3H). |
| 26 | ¹H NMR (500 MHz, Chloroform-d) δ 4.44 (s, 2H), 4.32-4.09 (m, 3H), 3.75-3.60 (m, 2H), 3.37 (s, 3H), 2.00-1.62 (m, 3H), 1.53-1.39 (m, 1H), 1.02 (t, J = 7.9 Hz, 3H). |
| 27 | ¹H NMR (500 MHz, Chloroform-d) δ 5.20 (d, J = 12.0 Hz, 1H), 4.47-4.37 (m, 4H), 3.64 (s, 3H), 2.45 (hept., J = 6.5 Hz, 1H), 0.96 (d, J = 6.5 Hz, 6H). |
| 28 | ¹H NMR (500 MHz, Chloroform-d) δ 4.58-4.48 (m, 1H), 4.41 (s, 2H), 3.75-3.63 (m, 2H), 3.63-3.49 (m, 2H), 3.37 (s, 3H), 0.91 (hept., J = 7.0 Hz, 1H), 0.57-0.45 (m, 4H). |
| 29 | ¹H NMR (500 MHz, Chloroform-d) δ 4.44 (s, 2H), 4.29-4.18 (m, 2H), 4.15-4.06 (m, 2H), 3.94-3.83 (m, 1H), 3.63-3.44 (m, 2H), 3.35 (s, 3H), 2.60 (s, 6H), 2.30-1.99 (m, 2H). |
| 30 | ¹H NMR (500 MHz, Chloroform-d) δ 5.29 (d, J = 12.5 Hz, 1H), 4.57 (t, J = 7.0 Hz, 1H), 4.44 (s, 2H), 4.39 (d, J = 12.5 Hz, 1H), 4.18 (dd, J = 12.5, 7.0 Hz, 1H), 3.93 (dd, J = 12.0, 7.0 Hz, 1H), 3.69 (s, 3H), 3.36 (s, 3H). |
| 31 | ¹H NMR (500 MHz, Chloroform-d) δ 5.24 (q, J = 6.5 Hz, 1H), 4.48-4.41 (m, 4H), 3.85 (s, 3H), 3.49 (s, 3H), 1.51 (d, J = 6.5 Hz, 3H), 1.11 (d, J = 6.5 Hz, 3H). |
| 32 | ¹H NMR (500 MHz, Chloroform-d) δ 6.10-6.01 (m, 1H), 5.46 (d, J = 6.0 Hz, 1H), 5.39-5.29 (m, 3H), 4.46-4.37 (m, 3H), 3.69 (s, 3H). |
| 33 | ¹H NMR (500 MHz, Chloroform-d) δ 5.75-5.69 (m, 2H), 4.44 (s, 2H), 4.38 (d, J = 8.0 Hz, 1H), 2.98-2.69 (m, 7H). |
| 34 | ¹H NMR (500 MHz, Chloroform-d) δ 6.93 (s, 1H), 6.84 (s, 1H), 6.16-6.02 (m, 2H), 4.45 (s, 4H), 3.26 (s, 6H), 1.59-1.43 (m, 3H), 0.88 (t, J = 8.0 Hz, 6H). |
| 35 | ¹H NMR (500 MHz, Chloroform-d) δ 6.69 (s, 1H), 5.37 (d, J = 7.5 Hz, 2H), 4.47 (s, 2H), 4.38 (d, J = 7.5 Hz, 1H), 3.69 (s, 3H). |
| 36 | ¹H NMR (500 MHz, Chloroform-d) δ 6.74 (s, 1H), 4.52-4.47 (m, 3H), 3.84-3.58 (m, 3H), 3.37 (s, 3H). |
| 37 | ¹H NMR (500 MHz, Chloroform-d) δ 6.05 (dd, J = 9.0, 1.5 Hz, 1H), 4.87 (t, J = 7.0 Hz, 1H), 4.45 (s, 2H), 4.34-4.01 (m, 2H), 3.25 (s, 3H), 1.30-1.13 (m, 2H), 0.85 (t, J = 8.0 Hz, 3H). |
| 38 | ¹H NMR (500 MHz, Chloroform-d) δ 5.34-5.20 (m, 3H), 5.15-4.95 (m, 2H), 4.86-4.66 (m, 3H), 4.54-4.37 (m, 4H), 4.44 (s, 4H), 4.21-4.13 (m, 2H), 2.33-2.20 (m, 4H), 1.17 (t, J = 8.0 Hz, 6H). |
| 39 | ¹H NMR (500 MHz, Chloroform-d) δ 6.34 (d, J = 7.1 Hz, 1H), 5.23 (d, J = 12.5 Hz, 2H), 4.99-4.91 (m, 2H), 4.94-4.85 (m, 1H), 4.46 (s, 4H), 4.39 (d, J = 12.4 Hz, 2H), 3.64 (s, 6H). |
| 40 | ¹H NMR (500 MHz, Chloroform-d) δ 5.93-5.77 (m, 1H), 5.26-5.10 (m, 2H), 4.78-4.68 (m, 2H), 4.57 (t, J = 2.5 Hz, 1H), 4.46 (s, 2H), 3.81-3.58 (m, 2H), 2.88-2.77 (m, 2H), 1.67 (s, 3H), 1.62 (s, 3H). |
| 41 | ¹H NMR (500 MHz, Chloroform-d) δ 5.27-5.14 (m, 1H), 4.43 -4.30 (m, 3H), 3.66 (s, 3H). |
| 42 | ¹H NMR (500 MHz, Chloroform-d) δ 5.28-5.04 (m, 1H), 4.55-4.48 (m, 1H), 4.44 (s, 2H), 3.00 (s, 6H), 2.89-2.72 (m, 2H). |
| 43 | ¹H NMR (500 MHz, Chloroform-d) δ 5.83 (s, 1H), 5.14 (q, J = 6.5 Hz, 1H), 4.46 (s, 2H), 3.85 (s, 3H), 1.62 (d, J = 6.5 Hz, 3H). |
| 44 | ¹H NMR (500 MHz, Chloroform-d) δ 5.41 (d, J = 8.5 Hz, 1H), 4.93 (t, J = 7.0 Hz, 1H), 4.45-4.30 (m, 3H), 3.69 (s, 3H), 3.54-3.32 (m, 2H). |
| 46 | ¹H NMR (500 MHz, Chloroform-d) δ 4.88-4.68 (m, 2H), 4.45 (s, 2H), 3.57-3.27 (m, 2H), 2.75 (s, 6H), 2.79-2.71 (m, 1H), 2.65-2.52 (m, 1H), 2.32 (s, 6H), 2.24-2.11 (m, 2H). |
| 47 | ¹H NMR (500 MHz, Chloroform-d) δ 5.80 (s, 1H), 4.54-4.44 (m, 1H), 4.44 (s, 2H), 3.74-3.64 (m, 1H), 3.63-3.50 (m, 2H), 3.37 (s, 3H), 2.23 (s, 3H). |
| 48 | ¹H NMR (500 MHz, Chloroform-d) δ 4.67 (t, J = 8.0 Hz, 1H), 4.40 (s, 2H), 3.69 (s, 3H), 3.50 (s, 2H), 3.22 (d, J = 8.0 Hz, 2H). |
| 49 | ¹H NMR (500 MHz, Chloroform-d) δ 7.26 (s, 1H), 4.53-4.48 (m, 1H), 4.45 (s, 2H), 3.58-3.47 (m, 3H), 3.37 (s, 3H). |
| 50 | ¹H NMR (500 MHz, Chloroform-d) δ 6.23 (s, 1H), 5.83-5.50 (m, 2H), 5.18-5.08 (m, 1H), 4.73-4.56 (m, 2H), 4.45 (s, 2H), 3.44 (s, 3H), 1.60 (s, 3H), 1.55 (s, 3H). |
| 51 | ¹H NMR (500 MHz, Chloroform-d) δ 5.57-5.43 (m, 2H), 4.74-4.55 (m, 1H), 4.44 (s, 2H), 4.30-4.16 (m, 1H), 3.57-3.44 (m, 1H), 2.58-2.12 (m, 2H), 1.17 (t, J = 8.0 Hz, 3H). |
| 52 | ¹H NMR (500 MHz, Chloroform-d) δ 5.72 (s, 1H), 4.61-4.46 (m, 3H), 4.18-4.02 (m, 1H), 3.69 (s, 3H), 2.86-2.77 (m, 1H), 2.75 (s, 6H), 2.03-1.98 (m, 2H). |
| 53 | ¹H NMR (500 MHz, Chloroform-d) δ 7.57-7.51 (m, 2H), 7.27-7.20 (m, 3H), 5.29-5.12 (m, 1H), 4.85 (t, J = 7.0 Hz, 1H), 4.43-4.25 (m, 3H), 3.72 (s, 3H), 3.51-3.13 (m, 2H). |
| 54 | ¹H NMR (500 MHz, Chloroform-d) δ 7.82 (q, J = 6.5 Hz, 1H), 7.28-7.01 (m, 3H), 6.25 (s, 1H), 4.45 (s, 2H), 4.02 (s, 3H), 1.74 (d, J = 6.5 Hz, 3H). |
| 55 | ¹H NMR (500 MHz, Chloroform-d) δ 7.48-7.40 (m, 2H), 6.39 (dd, J = 7.5, 1.5 Hz, 1H), 6.09 (s, 1H), 5.01-4.89 (m, 2H), 4.60-4.51 (m, 1H), 4.46 (s, 2H), 3.97-3.81 (m, 1H), 2.63-2.33 (m, 2H), 1.17 (t, J = 8.0 Hz, 3H). |
| 56 | ¹H NMR (500 MHz, Chloroform-d) δ 8.35 (s, 1H), 7.56 (s, 1H), 4.57 (s, 1H), 4.40 (s, 2H), 3.69 (s, 3H), 3.50 (s, 2H). |
| 57 | ¹H NMR (500 MHz, Chloroform-d) δ 7.42 (d, J = 7.5 Hz, 1H), 6.32 (s, 1H), 6.23 (d, J = 7.5 Hz, 1H), 4.71-4.46 (m, 3H), 4.39-4.25 (m, 3H), 3.75-3.62 (m, 2H), 3.37 (s, 3H), 1.40 (t, J = 8.0 Hz, 3H). |
| 58 | ¹H NMR (500 MHz, Chloroform-d) δ 6.83 (s, 1H), 6.22 (s, 1H), 5.06-4.95 (m, 2H), 4.46 (s, 2H), 4.32-4.14 (m, 2H), 3.82 (s, 3H), 2.67-2.44 (m, 2H), 2.38 (s, 3H), 1.17 (t, J = 8.0 Hz, 3H). |
| 59 | ¹H NMR (500 MHz, Chloroform-d) δ 7.79 (s, 1H), 7.51 (q, J = 6.8 Hz, 2H), 7.14 (d, J = 7.5 Hz, 2H), 6.40-6.32 (m, 4H), 4.45 (s, 4H), 3.98 (s, 6H), 1.76 (d, J = 6.8 Hz, 6H). |

TABLE 2-continued

¹HNMR data of compounds

| No. | ¹HNMR |
|---|---|
| 60 | ¹H NMR (500 MHz, Chloroform-d) δ 7.63-7.37 (m, 5H), 5.90 (s, 1H), 4.99-4.84 (m, 2H), 4.42 (s, 2H), 3.70 (s, 3H). |
| 61 | ¹H NMR (500 MHz, Chloroform-d) δ 7.65 (d, J = 7.0 Hz, 2H), 7.58-7.52 (m, 2H), 5.89 (s, 1H), 4.43 (s, 2H), 4.28-3.91 (m, 2H), 3.60-3.50 (m, 2H), 3.37 (s, 3H). |
| 62 | ¹H NMR (500 MHz, Chloroform-d) δ 7.65 (q, J = 1.6 Hz, 1H), 7.51-7.41 (m, 3H), 6.00-5.87 (m, 2H), 5.25-5.16 (m, 1H), 5.18-5.08 (m, 2H), 4.46 (s, 2H), 4.27-4.13 (m, 1H), 1.62 (s, 3H), 1.57 (s, 3H). |
| 63 | ¹H NMR (500 MHz, Chloroform-d) δ 7.36 (d, J = 7.5 Hz, 1H), 6.82 (d, J = 2.5 Hz, 1H), 6.76 (dd, J = 7.5, 2.0 Hz, 1H), 6.13 (d, J = 1.0 Hz, 1H), 5.19 (d, J = 12.3 Hz, 1H), 4.42-4.35 (m, 3H), 3.69-3.55 (m, 6H), 2.33 (d, J = 8.0 Hz, 3H). |
| 64 | ¹H NMR (500 MHz, Chloroform-d) δ 8.64 (d, J = 1.5 Hz, 1H), 8.45 (dd, J = 5.0, 1.5 Hz, 1H), 7.76-7.36 (m, 2H), 5.80 (s, 1H), 4.42 (s, 2H), 4.17-4.07 (m, 2H), 3.69-3.57 (m, 1H), 3.60-3.48 (m, 1H), 3.37 (s, 3H). |
| 65 | ¹H NMR (500 MHz, Chloroform-d) δ 9.04 (s, 1H), 8.77 (s, 2H), 5.81 (s, 1H), 5.26 (d, J = 8.0 Hz, 1H), 4.41 (s, 2H), 4.34 (d, J = 8.0 Hz, 1H), 3.67 (s, 3H). |
| 66 | ¹H NMR (500 MHz, Chloroform-d) δ 7.76-7.19 (m, 7H), 5.61 (s, 1H), 4.43 (s, 2H), 4.34 (q, J = 8.0 Hz, 1H), 3.67 (s, 3H), 1.27 (d, J = 8.0 Hz, 3H). |
| 67 | ¹H NMR (500 MHz, Chloroform-d) δ 6.00 (dd, J = 10.0, 1.5 Hz, 1H), 4.59 (q, J = 6.5 Hz, 1H), 4.45 (s, 2H), 3.27 (s, 3H), 1.77-1.68 (m, 4H), 1.23-0.87 (m, 4H). |
| 68 | ¹H NMR (500 MHz, Chloroform-d) δ 4.49-4.58 (m, 2H), 4.45 (s, 2H), 3.72-3.62 (m, 1H), 3.60-3.50 (m, 2H), 3.37 (s, 3H), 1.68 (d, J = 7.0 Hz, 3H). |
| 69 | ¹H NMR (500 MHz, Chloroform-d) δ 4.67 (q, J = 6.5 Hz, 1H), 4.45 (s, 2H), 4.20-4.09 (m, 2H), 3.38-3.12 (m, 3H), 3.04-2.95 (m, 1H), 1.61 (d, J = 6.5 Hz, 3H), 1.59-1.42 (m, 2H), 1.41-1.27 (m, 1H), 1.29-1.15 (m, 1H), 1.03 (t, J = 7.5 Hz, 3H). |
| 70 | ¹H NMR (500 MHz, Chloroform-d) δ 4.83-4.67 (m, 1H), 4.46 (s, 2H), 3.62-3.52 (m, 1H), 3.08-2.90 (m, 3H), 2.12-1.87 (m, 3H), 1.61 (d, J = 6.5 Hz, 3H), 1.09 (t, J = 8.0 Hz, 6H). |
| 71 | ¹H NMR (500 MHz, Chloroform-d) δ 5.04 (d, J = 12.5 Hz, 1H), 4.89 (d, J = 12.5 Hz, 1H), 4.60 (q, J = 7.0 Hz, 1H), 4.45 (s, 2H), 4.23-4.30 (m, 2H), 1.69 (d, J = 7.0Hz, 3H), 1.22 (t, J = 8.0 Hz, 3H). |
| 72 | ¹H NMR (500 MHz, Chloroform-d) δ 5.32 (q, J = 7.0 Hz, 1H), 4.62 (q, J = 7.0 Hz, 1H), 4.45 (s, 2H), 3.85 (s, 3H), 1.73 (d, J = 7.0 Hz, 3H), 1.59 (d, J = 7.0 Hz, 3H). |
| 73 | ¹H NMR (500 MHz, Chloroform-d) δ 4.88-4.72 (m, 2H), 4.54-4.48 (m, 1H), 4.47 (s, 2H), 4.17-4.02 (m, 2H), 2.53-2.12 (m, 2H), 1.61 (d, J = 7.5 Hz, 3H), 1.17 (t, J = 8.0 Hz, 3H). |
| 74 | ¹H NMR (500 MHz, Chloroform-d) δ 5.90-5.98 (m, 1H), 5.13-5.26 (m, 1H), 5.22-5.11 (m, 1H), 4.94-4.86 (m, 1H), 4.68-4.59 (m, 2H), 4.45 (s, 2H), 1.69 (d, J = 7.0 Hz, 3H), 1.62 (s, 3H), 1.57 (s, 3H). |
| 75 | ¹H NMR (500 MHz, Chloroform-d) δ 5.32 (d, J = 12.5 Hz, 1H), 5.03 (d, J = 12.5 Hz, 1H), 4.70 (q, J = 6.5 Hz, 1H), 4.47 (s, 2H), 2.84 (s, 6H), 1.61 (d, J = 6.5 Hz, 3H). |
| 76 | ¹H NMR (500 MHz, Chloroform-d) δ 7.82 (q, J = 6.5 Hz, 1H), 4.57 (q, J = 6.5 Hz, 1H), 4.45 (s, 2H), 4.01 (s, 3H), 1.69-1.52 (m, 6H). |
| 77 | ¹H NMR (500 MHz, Chloroform-d) δ 6.76 (s, 1H), 4.61 (q, J = 6.5 Hz, 1H), 4.44 (s, 2H), 1.73 (d, J = 6.5 Hz, 3H), 1.66 (s, 2H). |
| 78 | ¹H NMR (500 MHz, Chloroform-d) δ 8.09 (s, 1H), 4.93 (s, 1H), 4.71 (q, J = 6.5 Hz, 1H), 4.47 (s, 2H), 3.63 (s, 3H), 1.71 (d, J = 6.5 Hz, 3H), 1.44 (s, 9H). |
| 79 | ¹H NMR (500 MHz, Chloroform-d) δ 4.58 (q, J = 7.0 Hz, 1H), 4.45 (s, 2H), 4.38-4.29 (m, 1H), 3.96-3.86 (m, 1H), 3.88-3.79 (m, 1H), 3.77-3.68 (m, 1H), 2.58 (s, 6H), 1.68 (d, J = 7.0 Hz, 3H). |
| 80 | ¹H NMR (500 MHz, Chloroform-d) δ 5.93 (d, J = 12.0 Hz, 1H), 5.01 (d, J = 12.0 Hz, 1H), 4.59 (q, J = 6.5 Hz, 1H), 4.45 (s, 2H), 2.87 (s, 3H), 1.69 (d, J = 6.5 Hz, 3H). |
| 82 | ¹H NMR (500 MHz, Chloroform-d) δ 6.20-6.02 (m, 1H), 4.67 (q, J = 6.5 Hz, 1H), 4.47-4.38 (m, 3H), 4.26-4.14 (m, 3H), 4.13-3.99 (m, 2H), 1.62 (d, J = 6.5 Hz, 3H). |
| 83 | ¹H NMR (500 MHz, Chloroform-d) δ 5.14-5.05 (m, 2H), 4.64 (q, J = 6.5 Hz, 1H), 4.46 (s, 2H), 3.61-3.14 (m, 2H), 2.92 (t, J = 3.0 Hz, 1H), 1.60 (d, J = 6.5 Hz, 3H). |
| 84 | ¹H NMR (500 MHz, Chloroform-d) δ 7.34-7.26 (m, 2H), 6.95-6.85 (m, 3H), 6.05 (d, J = 12.0 Hz, 1H), 5.97 (d, J = 12.5 Hz, 1H), 4.67 (q, J = 6.5 Hz, 1H), 4.43 (s, 2H), 1.62 (d, J = 6.5 Hz, 3H). |
| 85 | ¹H NMR (500 MHz, Chloroform-d) δ 7.67-7.56 (m, 3H), 7.38-7.13 (m, 3H), 7.03 (t, J = 1.5 Hz, 1H), 6.17 (d, J = 12.5 Hz, 1H), 6.09 (d, J = 12.5 Hz, 1H), 4.62 (q, J = 6.5 Hz, 1H), 3.76 (s, 2H), 1.71 (d, J = 6.5 Hz, 3H). |
| 86 | ¹H NMR (500 MHz, Chloroform-d) δ 7.29-7.22 (m, 2H), 7.19-7.10 (m, 2H), 5.28 (d, J = 12.0 Hz, 1H), 5.20 (d, J = 12.0 Hz, 1H), 4.81-4.56 (m, 2H), 4.43-4.34 (m, 3H), 2.36 (s, 2H), 2.36 (d, J = 2.0 Hz, 1H), 1.69 (d, J = 6.5 Hz, 3H). |
| 87 | ¹H NMR (500 MHz, Chloroform-d) δ 8.26 (dd, J = 5.0, 1.5 Hz, 1H), 7.32-7.22 (m, 1H), 6.73 (dd, J = 8.0, 1.0 Hz, 1H), 6.59-6.43 (m, 1H), 6.16 (d, J = 12.0 Hz, 1H), 6.00 (d, J = 12.5 Hz, 1H), 4.57 (q, J = 6.5 Hz, 1H), 4.42 (s, 2H), 1.69 (d, J = 6.5 Hz, 3H). |
| 88 | ¹H NMR (500 MHz, Chloroform-d) δ 5.52-5.04 (m, 2H), 4.58 (q, J = 6.5 Hz, 1H), 4.45 (s, 2H), 4.04-3.79 (m, 3H), 3.38-3.23 (m, 2H), 2.11-1.94 (m, 2H), 1.73-1.61 (m, 4H), 1.53-1.42 (m, 1H). |
| 89 | ¹H NMR (500 MHz, Chloroform-d) δ 7.35 (d, J = 7.5 Hz, 1H), 6.13-5.87 (m, 2H), 5.46 (d, J = 7.0 Hz, 1H), 4.68 (q, J = 7.0 Hz, 1H), 4.46 (s, 2H), 3.90 (s, 3H), 1.63 (d, J = 6.5 Hz, 3H). |
| 90 | ¹H NMR (500 MHz, Chloroform-d) δ 4.72-4.61 (m, 2H), 4.46 (s, 2H), 4.25-4.11 (m, 1H), 3.66 (s, 3H), 3.49-3.37 (m, 1H), 2.47 (s, 3H), 1.96-1.86 (m, 1H), 1.62 (d, J = 6.5 Hz, 3H). |
| 91 | ¹H NMR (500 MHz, Chloroform-d) δ 4.89-4.66 (m, 3H), 4.47 (s, 2H), 4.33-4.21 (m, 3H), 3.14 (s, 3H), 2.74-2.66 (m, 1H), 1.59 (d, J = 7.5 Hz, 3H), 1.17 (t, J = 8.0 Hz, 3H). |
| 92 | ¹H NMR (500 MHz, Chloroform-d) δ 6.11-6.00 (m, 1H), 4.89-4.70 (m, 2H), 4.46 (s, 2H), 3.97-3.62 (m, 2H), 3.41-3.31 (m, 2H), 2.74 (s, 3H), 2.07-1.99 (m, 1H), 1.61 (d, J = 6.5 Hz, 3H). |
| 93 | ¹H NMR (500 MHz, Chloroform-d) δ 7.29-7.21 (m, 2H), 6.77-6.70 (m, 3H), 6.59 (d, J = 8.5 Hz, 1H), 5.39 (d, J = 8.5 Hz, 1H), 4.56 (q, J = 6.5 Hz, 1H), 4.42 (s, 2H), 2.98 (s, 3H), 1.68 (d, J = 6.5 Hz, 3H). |
| 94 | ¹H NMR (500 MHz, Chloroform-d) δ 4.63 (q, J = 6.5 Hz, 1H), 4.34-4.22 (m, 2H), 3.85 (s, 2H), 3.70 (s, 1H), 2.93-2.81 (m, 2H), 1.90 (s, 1H), 1.77 (d, J = 6.5 Hz, 3H). |
| 95 | ¹H NMR (500 MHz, Chloroform-d) δ 5.91 (q, J = 6.5 Hz, 1H), 4.57 (q, J = 6.5 Hz, 1H), 4.40 (s, 2H), 2.46-1.91 (m, 4H), 1.64 (d, J = 6.5 Hz, 3H), 0.90-0.81 (m, 2H), 0.64-0.59 (m, 2H). |

TABLE 2-continued

¹HNMR data of compounds

| No. | ¹HNMR |
|---|---|
| 96 | ¹H NMR (500 MHz, Chloroform-d) δ 7.96 (s, 1H), 7.87 (s, 1H), 4.67 (q, J = 6.5 Hz, 2H), 4.47 (s, 4H), 2.87 (s, 6H), 1.61 (d, J = 6.5 Hz, 6H). |
| 97 | ¹H NMR (500 MHz, Chloroform-d) δ 6.87 (q, J = 6.5 Hz, 1H), 4.58 (q, J = 6.5 Hz, 1H), 4.44 (s, 2H), 3.54 (s, 3H), 2.19 (s, 3H), 1.68 (d, J = 6.5 Hz, 3H), 1.52 (d, J = 6.5 Hz, 3H). |
| 98 | ¹H NMR (500 MHz, Chloroform-d) δ 5.64-5.32 (m, 2H), 4.68-4.60 (m, 2H), 4.48 (s, 2H), 4.01-3.89 (m, 1H), 2.60 (s, 3H), 1.61 (d, J = 6.5 Hz, 3H). |
| 99 | ¹H NMR (500 MHz, Chloroform-d) δ 7.53-7.44 (m, 5H), 5.64 (d, J = 12.5 Hz, 1H), 5.52 (d, J = 12.5 Hz, 1H), 4.56 (q, J = 6.5 Hz, 1H), 4.41 (s, 2H), 3.08 (s, 3H), 1.68 (d, J = 6.5 Hz, 3H). |
| 100 | ¹H NMR (500 MHz, Chloroform-d) δ 6.49 (s, 1H), 5.56 (s, 2H), 5.25 (d, J = 13.5 Hz, 1H), 5.00 (d, J = 13.5 Hz, 1H), 4.57 (q, J = 6.5 Hz, 1H), 4.44 (s, 2H), 3.43-3.24 (m, 2H), 1.68 (d, J = 6.5 Hz, 3H). |
| 101 | ¹H NMR (500 MHz, Chloroform-d) δ 8.08 (s, 1H), 4.68 (q, J = 6.5 Hz, 1H), 4.46 (s, 2H), 4.13-4.00 (m, 1H), 3.79-3.67 (m, 7H), 1.69 (d, J = 6.5 Hz, 3H), 1.23 (t, J = 8.0 Hz, 3H). |
| 102 | ¹H NMR (500 MHz, Chloroform-d) δ 6.86-6.72 (m, 1H), 6.22 (s, 1H), 6.14-6.15 (m, 1H), 5.20-5.13 (m, 2H), 4.61 (q, J = 6.5 Hz, 1H), 4.43 (s, 2H), 2.31 (s, 3H), 1.68-1.62 (m, 4H). |
| 103 | ¹H NMR (500 MHz, Chloroform-d) δ 6.69 (s, 1H), 4.91-4.60 (m, 2H), 4.41 (s, 2H), 1.74-1.66 (m, 5H), 1.16-1.08 (m, 6H). |
| 104 | ¹H NMR (500 MHz, Chloroform-d) δ 7.63-7.53 (m, 2H), 7.51-7.45 (m, 2H), 6.54 (s, 1H), 5.56-5.40 (m, 1H), 4.87-4.61 (m, 2H), 4.38 (s, 2H), 1.89 (s, 2H), 1.54 (d, J = 6.5 Hz, 3H). |
| 105 | ¹H NMR (500 MHz, Chloroform-d) δ 5.25-5.18 (m, 1H), 4.60 (q, J = 6.5 Hz, 1H), 4.43-4.35 (m, 3H), 1.69 (d, J = 6.5 Hz, 3H). |
| 106 | ¹H NMR (500 MHz, Chloroform-d) δ 5.30 (q, J = 6.5 Hz, 1H), 4.60 (q, J = 6.5 Hz, 1H), 4.45 (s, 2H), 1.70 (d, J = 6.5 Hz, 3H), 1.50 (d, J = 6.5 Hz, 3H). |
| 107 | ¹H NMR (500 MHz, Chloroform-d) δ 5.29-5.16 (m, 1H), 4.59-4.48 (m, 2H), 4.37 (s, 2H), 4.00 (d, J = 7.0 Hz, 2H), 1.73 (d, J = 7.0 Hz, 3H), 1.27-1.10 (m, 1H), 0.54-0.45 (m, 2H), 0.30-0.21 (m, 2H). |
| 108 | ¹H NMR (500 MHz, Chloroform-d) δ 7.13-7.07 (m, 2H), 6.90-6.83 (m, 2H), 5.46-5.37 (m, 1H), 4.60-4.52 (m, 2H), 4.42 (s, 2H), 2.31-2.21 (m, 3H), 1.72 (d, J = 6.5 Hz, 3H). |
| 109 | ¹H NMR (500 MHz, Chloroform-d) δ 8.52 (d, J = 5.0 Hz, 2H), 7.42 (dd, J = 5.0, 2.5 Hz, 2H), 5.38 (d, J = 12.5 Hz, 1H), 5.25 (d, J = 12.5 Hz, 1H), 4.66-4.55 (m, 2H), 4.46 (d, J = 12.5 Hz, 1H), 4.38 (s, 2H), 1.65 (d, J = 6.5 Hz, 3H). |
| 110 | ¹H NMR (500 MHz, Chloroform-d) δ 6.97 (d, J = 7.5 Hz, 1H), 6.32 (dd, J = 7.5, 2.0 Hz, 1H), 5.50 (dd, J = 12.5, 2.5 Hz, 1H), 5.34 (d, J = 12.5 Hz, 1H), 4.95-4.79 (m, 2H), 4.59 (q, J = 6.5 Hz, 1H), 4.45 (s, 2H), 3.92 (s, 3H), 2.38-2.24 (m, 2H), 1.69 (d, J = 6.5 Hz, 3H). |
| 111 | ¹H NMR (500 MHz, Chloroform-d) δ 6.80 (dd, J = 7.5, 1.5 Hz, 1H), 6.59 (d, J = 7.5 Hz, 1H), 5.37 (dd, J = 7.0, 5.5 Hz, 1H), 4.66-4.55 (m, 2H), 4.41 (s, 2H), 3.57 (s, 3H), 1.70 (d, J = 6.5 Hz, 3H). |
| 112 | ¹H NMR (500 MHz, Chloroform-d) δ 5.23 (d, J = 12.5 Hz, 1H), 4.57 (q, J = 6.5 Hz, 1H), 4.44-4.34 (m, 3H), 4.31 (dd, J = 12.0, 7.0 Hz, 1H), 4.24 (p, J = 6.5 Hz, 1H), 3.86-3.78 (m, 2H), 3.79-3.71 (m, 1H), 2.08-1.95 (m, 1H), 1.98-1.86 (m, 1H), 1.69-1.53 (m, 5H). |
| 113 | ¹H NMR (500 MHz, Chloroform-d) δ 5.74 (s, 2H), 5.14 (d, J = 12.5 Hz, 1H), 4.90 (d, J = 12.0 Hz, 1H), 4.74 (q, J = 6.5 Hz, 1H), 4.46 (s, 2H), 1.65 (d, J = 6.5 Hz, 3H). |
| 114 | ¹H NMR (500 MHz, Chloroform-d) δ 7.41-7.35 (m, 2H), 7.01-6.95 (m, 2H), 4.95-4.63 (m, 2H), 4.55 (s, 2H), 4.45-4.32 (m, 1H), 3.44 (s, 3H), 2.06-1.89 (m, 1H), 1.62 (d, J = 6.5 Hz, 3H). |
| 115 | ¹H NMR (500 MHz, Chloroform-d) δ 8.04 (s, 1H), 7.33-7.21 (m, 2H), 4.72-4.61 (m, 4H), 4.53-4.45 (m, 5H), 3.42 (s, 6H), 1.69 (d, J = 6.5 Hz, 6H). |
| 116 | ¹H NMR (500 MHz, Chloroform-d) δ 7.40-7.29 (m, 10H), 5.48 (d, J = 12.0 Hz, 1H), 5.03 (d, J = 12.5 Hz, 1H), 4.57 (q, J = 6.5 Hz, 1H), 4.44 (s, 2H), 1.64 (d, J = 6.5 Hz, 3H). |
| 117 | ¹H NMR (500 MHz, Chloroform-d) δ 7.20 (d, J = 15.0 Hz, 1H), 6.65 (d, J = 15.0 Hz, 1H), 6.47 (d, J = 12.0 Hz, 1H), 6.39 (d, J = 12.5 Hz, 1H), 4.55 (q, J = 6.5 Hz, 1H), 4.40 (s, 2H), 1.70 (d, J = 6.5 Hz, 3H). |
| 118 | ¹H NMR (500 MHz, Chloroform-d) δ 5.48-5.28 (m, 1H), 4.72-4.59 (m, 2H), 4.40 (s, 2H), 4.26-4.13 (m, 2H), 1.63 (d, J = 6.5 Hz, 3H). |
| 119 | ¹H NMR (500 MHz, Chloroform-d) δ 7.01 (d, J = 12.5 Hz, 1H), 5.52 (d, J = 12.5 Hz, 1H), 4.46 (q, J = 6.5 Hz, 1H), 4.37 (s, 2H), 3.57-3.33 (m, 1H), 1.69 (d, J = 6.5 Hz, 3H), 0.57-0.41 (m, 4H). |
| 120 | ¹H NMR (500 MHz, Chloroform-d) δ 8.37 (dd, J = 5.0, 1.0 Hz, 1H), 7.38 (dd, J = 8.0, 1.0 Hz, 1H), 6.98 (d, J = 12.5 Hz, 1H), 6.83-6.72 (m, 2H), 5.81 (d, J = 12.5 Hz, 1H), 4.58 (q, J = 6.5 Hz, 1H), 4.42 (s, 2H), 1.68 (d, J = 6.5 Hz, 3H). |
| 121 | ¹H NMR (500 MHz, Chloroform-d) δ 7.30-7.16 (m, 2H), 6.81-6.72 (m, 3H), 5.86 (d, J = 12.5 Hz, 1H), 5.35 (dd, J = 12.5, 1.0 Hz, 1H), 5.17 (d, J = 12.5 Hz, 1H), 4.54 (q, J = 6.5 Hz, 1H), 4.41 (s, 2H), 3.71 (s, 3H), 1.60 (d, J = 6.5 Hz, 3H). |
| 122 | ¹H NMR (500 MHz, Chloroform-d) δ 7.26 (d, J = 12.5 Hz, 1H), 7.20-7.11 (m, 2H), 7.14-7.07 (m, 2H), 7.01 (d, J = 12.5 Hz, 1H), 6.89 (d, J = 12.0 Hz, 2H), 6.44 (dd, J = 7.65, 2.5 Hz, 2H), 5.89 (d, J = 12.5, 2.5 Hz, 2H), 5.80 (d, J = 12.5 Hz, 2H), 5.51-5.45 (m, 2H), 4.60 (q, J = 6.5 Hz, 2H), 4.48 (s, 4H), 1.69 (d, J = 6.5 Hz, 6H). |
| 123 | ¹H NMR (500 MHz, Chloroform-d) δ 4.58 (q, J = 6.9 Hz, 1H), 4.22-4.08 (m, 1H), 3.52-3.39 (m, 1H), 3.19-3.09 (m, 1H), 3.13 (s, 1H), 2.79 (s, 2H), 1.68 (d, J = 6.5 Hz, 2H), 1.55-1.45 (m, 1H), 1.30-1.21 (m, 1H), 1.03 (t, J = 7.5 Hz, 2H). |
| 124 | ¹H NMR (500 MHz, Chloroform-d) δ 4.94-4.56 (m, 2H), 3.83-3.66 (m, 2H), 3.45-3.04 (m, 2H), 2.75 (s, 6H), 2.75-2.68 (m, 1H), 2.09-1.99 (m, 1H), 1.67 (d, J = 6.5 Hz, 3H), 1.23 (t, J = 8.0 Hz, 3H). |
| 125 | ¹H NMR (500 MHz, Chloroform-d) δ 9.90 (s, 1H), 5.30 (d, J = 12.5 Hz, 1H), 4.65-4.53 (m, 2H), 4.40 (d, J = 12.3 Hz, 1H), 3.69-3.45 (m, 1H), 2.20 (s, 3H), 1.71 (d, J = 7.0 Hz, 3H), 1.22 (t, J = 8.0 Hz, 3H). |
| 126 | ¹H NMR (500 MHz, Chloroform-d) δ 7.64 (dd, J = 7.5, 1.5 Hz, 1H), 6.43 (t, J = 7.5 Hz, 1H), 6.37 (dd, J = 7.5, 1.5 Hz, 1H), 5.26 (d, J = 12.5 Hz, 1H), 5.17 (d, J = 12.5 Hz, 1H), 4.71-4.62 (m, 2H), 4.38 (d, J = 12.5 Hz, 1H), 3.98 (s, 1H), 3.67 (s, 3H), 1.68 (d, J = 6.5 Hz, 3H). |
| 127 | ¹H NMR (500 MHz, Chloroform-d) δ 8.01-7.93 (m, 3H), 7.58-7.30 (m, 3H), 5.33 (d, J = 12.5 Hz, 1H), 4.97 (d, J = 12.5 Hz, 1H), 4.61 (q, J = 6.5 Hz, 1H), 2.99 (s, 6H), 1.71 (d, J = 6.5 Hz, 3H). |
| 128 | ¹H NMR (500 MHz, Chloroform-d) δ 7.42-7.36 (m, 2H), 7.39-7.29 (m, 3H), 5.93-5.78 (m, 1H), 5.25-5.16 (m, 1H), 5.20-5.10 (m, 1H), 5.06 (dd, J = 12.0, 1.0 Hz, 1H), 4.80-4.72 (m, 1H), 4.76-4.62 (m, 2H), 4.44 (d, J = 12.5 Hz, 1H), 3.22 (s, 1H), 1.66 (d, J = 6.5 Hz, 3H), 1.60 (s, 3H), 1.55 (s, 3H). |

TABLE 2-continued

¹HNMR data of compounds

| No. | ¹HNMR |
|---|---|
| 129 | ¹H NMR (500 MHz, DMSO-$d_6$) δ 6.80 (s, 2H), 4.66 (q, J = 7.0 Hz, 1H), 4.45-4.50 (m, 1H), 3.46-3.51 (m, 1H), 2.80 (s, 2H), 2.60-2.74 (m, 2H), 1.52 (d, J = 7.0 Hz, 3H). |
| 130 | ¹H NMR (500 MHz, DMSO-$d_6$) δ 6.81 (s, 2H), 4.67 (q, J = 7.0 Hz, 1H), 4.37-4.42 (m, 1H), 4.02-4.08 (m, 1H), 2.75 (s, 6H), 2.59-2.62 (m, 1H), 1.79-1.89 (m, 1H), 1.52 (d, J = 7.0 Hz, 3H). |
| 131 | ¹H NMR (500 MHz, Chloroform-d) δ 4.90-4.57 (m, 2H), 4.44 (s, 2H), 3.43 (dd, J = 12.5, 7.0 Hz, 1H), 3.40-3.28 (m, 2H), 3.23-3.13 (m, 1H), 1.68 (d, J = 6.8 Hz, 3H), 1.58-1.43 (m, 2H), 1.30 (s, 2H), 1.31-1.18 (m, 2H), 1.03 (t, J = 7.5 Hz, 3H). |
| 132 | ¹H NMR (500 MHz, DMSO-d6) 6.43-6.34 (m, 2H), 6.22 (s, 1H), 4.99 (q, J = 7.0 Hz, 1H), 4.17-3.99 (m, 2H), 3.40-3.03 (m, 2H), 2.39 (s, 6H), 1.52 (d, J = 7.0 Hz, 3H) |

Several methods for preparing the compounds of the present invention are detailedly illustrated in the following schemes and examples. The starting materials can be purchased commercially or can be prepared by methods known in the literature or according to the detailed illustrations. Those skilled in the art will appreciate that other synthetic routes can also be utilized to synthesize the compounds of the present invention. Although specific starting materials and conditions in the synthetic route have been described below, they can be easily replaced with other similar starting materials and conditions, and various isomers of compounds and the like produced by variations or variants of the preparation methods of the present invention are included in the scope of the present invention. Additionally, the preparation methods described below can be further modified in accordance with the present disclosure, using conventional chemical methods well known to those skilled in the art. For example, appropriate groups are protected during the reaction, and the like.

The method examples are provided below to facilitate a further understanding of the preparation method of the present invention, and the specific materials, types and conditions used are determined to be further description of the present invention and are not intended to limit its rational scope. The reagents used for synthesizing the following compounds indicated in the table below are either commercially available or can be readily prepared by those skilled in the art.

The examples of representative compounds are as follows:

1. Synthesis of Compound 2

(1) Compound 2-1 (300 mg, 3.33 mmol) and TEA (404 mg, 4.00 mmol) were dissolved in dehydrated dichloromethane (20 ml), cooled to 0° C. and compound a (791 mg, 3.66 mmol) was slowly added dropwise. Heated slowly to room temperature and continued to react for 12 hours. The reaction was quenched by pouring the reaction solution into ice water, extracted and the organic phase was washed one time with 50 ml of saturated sodium bicarbonate. The organic phase was dried and then concentrated to obtain compound 2-2 (800 mg, crude product). Without further purification, the compound was directly used in the next step.

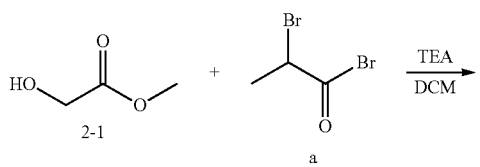

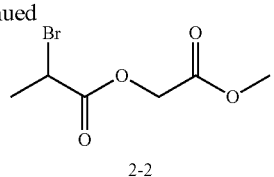

2-2

(2) Compound b (400 mg, 1.59 mmol), compound 2-2 (800 mg, crude product) obtained from step (1), a catalytic amount of TBAB (10 mg) and DMF (10 mL) were added to a 50 ml round-bottom flask, heated to 85° C. and reacted for 12 hours. After completed reaction of the starting materials according to LC-MS detection, the reaction solution was cooled to room temperature, and extracted with water (50 ml) and MTBE (50 ml). The organic phase was dried, concentrated, and separated by column chromatography to obtain compound 2 (300 mg, yield 49%), as a white solid.

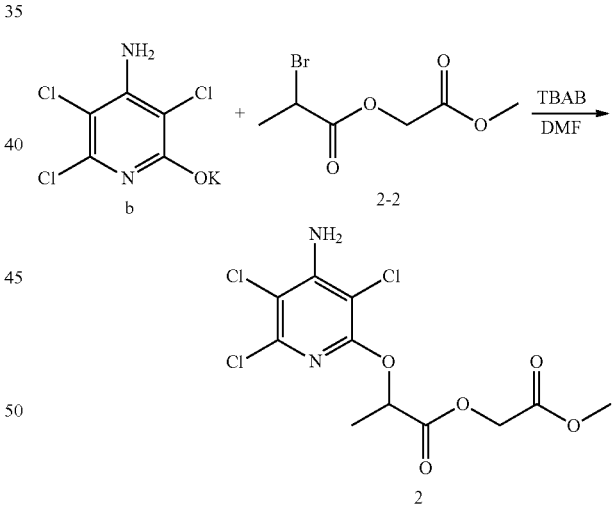

2. Synthesis of Compound 54

(1) Compound 54-1 (1 mg, 7.03 mmol) and compound 54-2 (845 mg, 7.03 mmol) were dissolved in 20 ml methanol. Cooled to 0° C., and thionyl chloride (920 mg, 7.74 mmol) was slowly added dropwise. Heated slowly to room temperature and continued to react for 12 hours at room temperature. After basically completed reaction of the starting materials according to HPLC detection, concentrated, washed with ethyl acetate (100 mL×2) and saturated sodium bicarbonate (50 mL). The organic phase was dried and then concentrated to obtain compound (1.5 g, crude product). Without further purification, the compound was directly used in the next step.

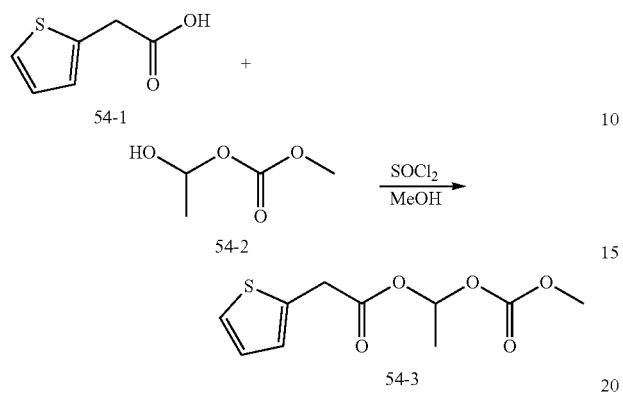

(2) Compound 54-3 (1.5 g, crude product) obtained from the above operations, NBS (1.09 g, 6.14 mmol), a catalytic amount of AIBN (10 mg) and carbon tetrachloride (100 ml) were added to a 100 ml single mouth flask and agitated for 12 hours at 60° C. After completed reaction of the starting materials according to HPLC detection, the reaction solution was cooled to room temperature. The solid was filtered and the carbon tetrachloride phase was concentrated, to obtain compound 54-4 (1 g, crude product), Without further purification, the compound was directly used in the next step.

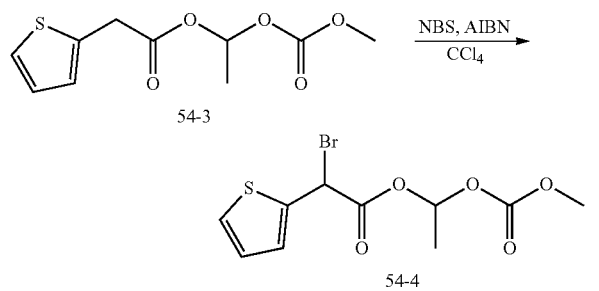

(3) Compound b (400 mg, 1.70 mmol), compound 54-4 (826 mg, 1.91), a catalytic amount of TBAB (10 mg) and DMF (10 mL) were added to a 50 ml round-bottom flask, heated to 85° C. and reacted for 12 hours. After completed reaction of the starting materials according to LC-MS detection, the reaction solution was cooled to room temperature, and extracted with water (50 ml) and MTBE (50 ml). The organic phase was dried, concentrated, and separated by column chromatography to obtain compound 54 (400 mg, yield 57%).

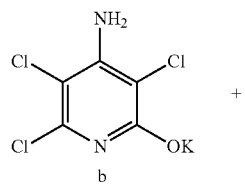

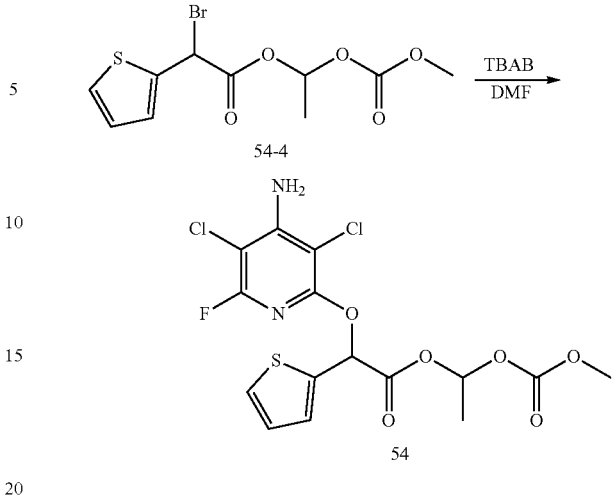

3. Synthesis of Compound 78

(1) Compound 78-1 (300 mg, 1.46 mmol) and TEA (178 mg, 175 mmol) were dissolved in dehydrated dichloromethane (20 ml), cooled to 0° C. and compound a (347 mg, 1.61 mmol) was slowly added dropwise. Heated slowly to room temperature and continued to react for 12 hours. The reaction was quenched by pouring the reaction solution into ice water, extracted and the organic phase was washed one time with 50 ml of saturated sodium bicarbonate. The organic phase was dried and then concentrated to obtain compound 78-2 (460 mg, crude product). Without further purification, the compound was directly used in the next step.

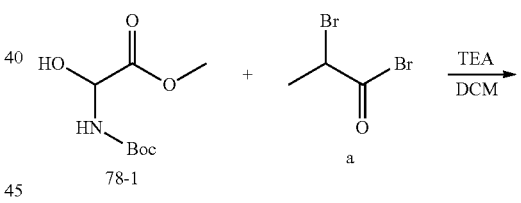

(2) Compound b (400 mg, 1.70 mmol), compound 78-2 (826 mg, 2.56 mmol) obtained from step (1), a catalytic amount of TBAB (10 mg) and DMF (10 mL) were added to a 50 ml round-bottom flask, heated to 85° C. and reacted for 12 hours. After completed reaction of the starting materials according to LC-MS detection, the reaction solution was cooled to room temperature, and extracted with water (50 ml) and MTBE (50 ml). The organic phase was dried, concentrated, and separated by column-chromatography to obtain compound 78 (300 mg, yield 38%).

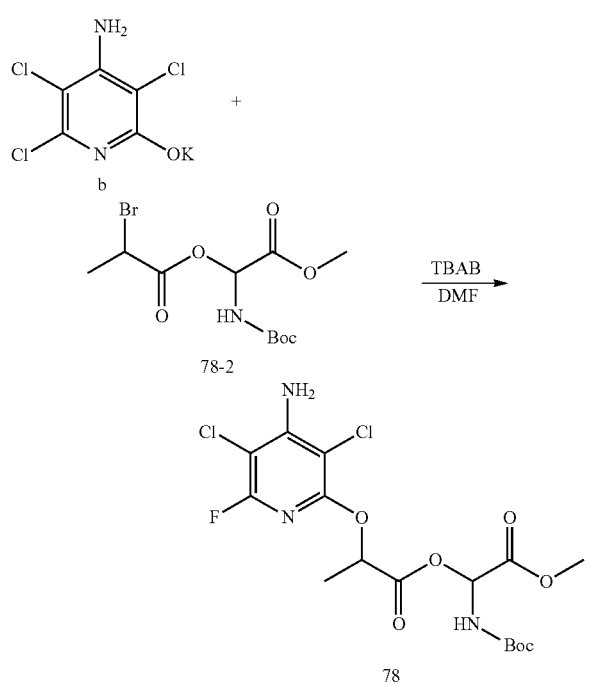

4. Synthesis of Compound 79

(1) Compound 79-1 (300 mg, 4.1 mmol) was dissolved in dehydrated methanol (20 ml), cooled to 0° C. and solid sodium methoxide was added in batches (244 mg, 4.51 mmol). Agitated for 10 min at 0° C. and compound 79-2 (199 mg, 4.51 mmol) was slowly added dropwise at this temperature. Heated slowly to room temperature and continued to react for 12 hours. After basically completed reaction of the starting materials according to HPLC detection, a few drops of acetate solution was added to neutral. The reaction solution was concentrated to remove methanol, extracted with water (100 ml) and ethyl acetate (100 ml×2). The organic phase was dried, concentrated to obtain compound 79-3 (500 mg, crude product). Without further purification, the compound was directly used in the next step.

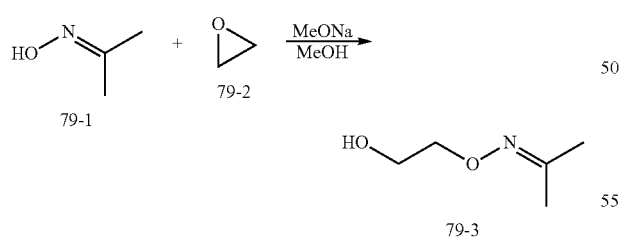

(2) Compound 79-3 (500 mg, crude product) and TEA (518 mg, 5.12 mmol) were dissolved in dehydrated dichloromethane (20 ml), cooled to 0° C. and compound a (1.01 g, 4.69 mmol) was slowly added dropwise. Heated slowly to room temperature and continued to react for 12 hours. The reaction was quenched by pouring the reaction solution into ice water, extracted and the organic phase was washed one time with 50 ml of saturated sodium bicarbonate. The organic phase was dried and then concentrated to obtain compound 79-4(1 g, crude product). Without further purification, the compound was directly used in the next step.

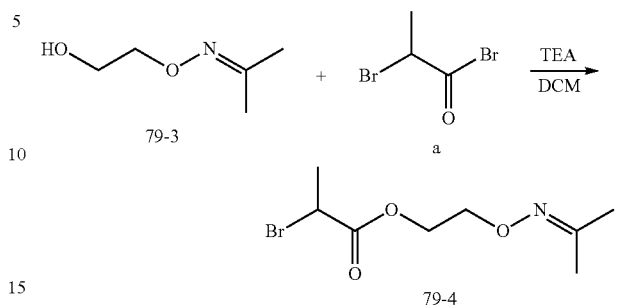

(3) Compound b (400 mg, 2.13 mmol), compound 79-4 (1 g, crude product) obtained from step (2), a catalytic amount of TBAB (10 mg) and DMF (10 mL) were added to a 50 ml round-bottom flask, heated to 85° C. and reacted for 12 hours. After completed reaction of the starting materials according to LC-MS detection, the reaction solution was cooled to room temperature, and extracted with water (100 ml) and MTBE (50 ml×2). The organic phase was dried, concentrated, and separated by column chromatography to obtain compound 79 (240 mg, yield 38%), as a white solid.

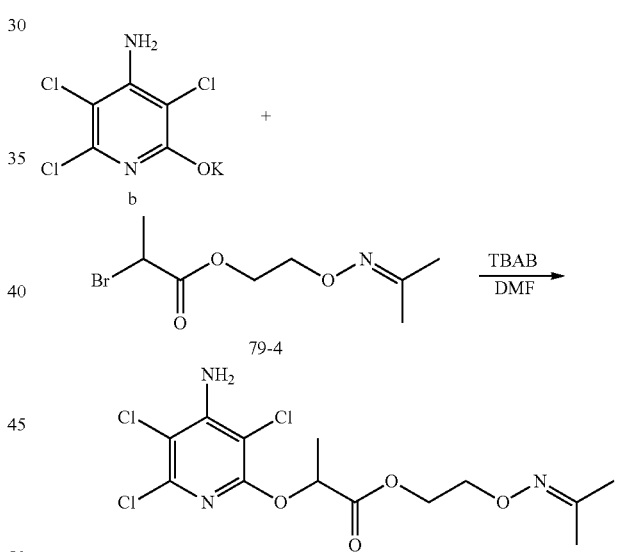

5. Synthesis of Compounds 74 and 128

(1) Compound 74-1 (300 mg, 2.08 mmol) and TEA (253 mg, 2.50 mmol) were dissolved in dehydrated dichloromethane (20 ml), cooled to 0° C. and compound a (494 mg, 2.29 mmol) was slowly added dropwise. Heated slowly to room temperature and continued to react for 12 hours. The reaction was quenched by pouring the reaction solution into ice water, extracted and the organic phase was washed one time with 50 ml of saturated sodium bicarbonate. The organic phase was dried and then concentrated to obtain compound 74-2 (500 mg, crude product). Without further purification, the compound was directly used in the next step.

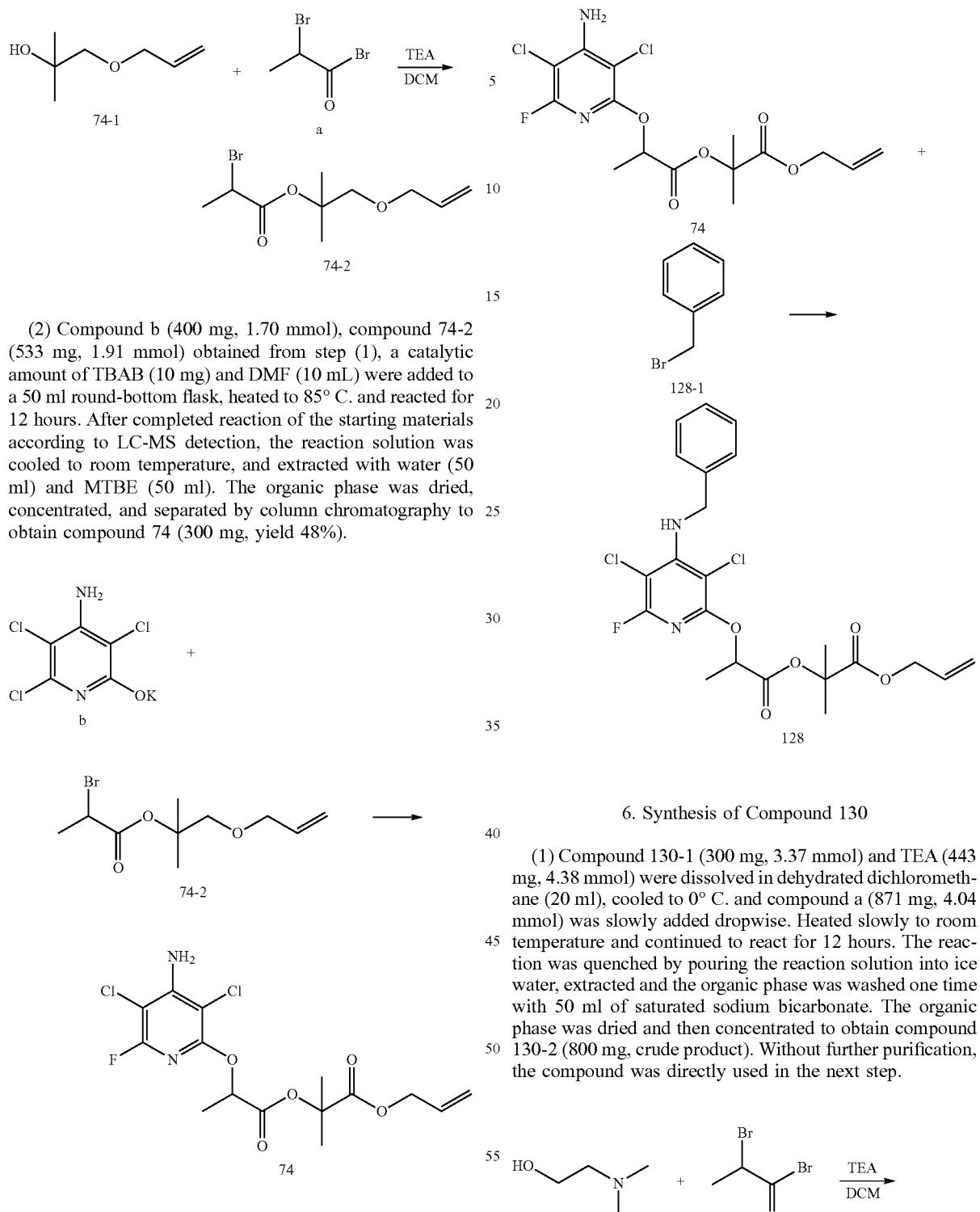

(2) Compound b (400 mg, 1.70 mmol), compound 74-2 (533 mg, 1.91 mmol) obtained from step (1), a catalytic amount of TBAB (10 mg) and DMF (10 mL) were added to a 50 ml round-bottom flask, heated to 85° C. and reacted for 12 hours. After completed reaction of the starting materials according to LC-MS detection, the reaction solution was cooled to room temperature, and extracted with water (50 ml) and MTBE (50 ml). The organic phase was dried, concentrated, and separated by column chromatography to obtain compound 74 (300 mg, yield 48%).

(3) Compound 74 (300 mg, 0.76 mmol), compound 128-1 (195 mg, 1.14 mmol), potassium carbonate (210 mg, 1.52 mmol), a catalytic amount of DMAP (10 mg) and acetonitrile (20 ml) were added to a 50 ml round-bottom flask. Heated to 80° C. and reacted for 12 hours. After completed reaction of the starting materials according to LC-MS detection, the reaction solution was cooled to room temperature, concentrated, and separated by column chromatography to obtain compound 128 (150 mg, yield 41%).

6. Synthesis of Compound 130

(1) Compound 130-1 (300 mg, 3.37 mmol) and TEA (443 mg, 4.38 mmol) were dissolved in dehydrated dichloromethane (20 ml), cooled to 0° C. and compound a (871 mg, 4.04 mmol) was slowly added dropwise. Heated slowly to room temperature and continued to react for 12 hours. The reaction was quenched by pouring the reaction solution into ice water, extracted and the organic phase was washed one time with 50 ml of saturated sodium bicarbonate. The organic phase was dried and then concentrated to obtain compound 130-2 (800 mg, crude product). Without further purification, the compound was directly used in the next step.

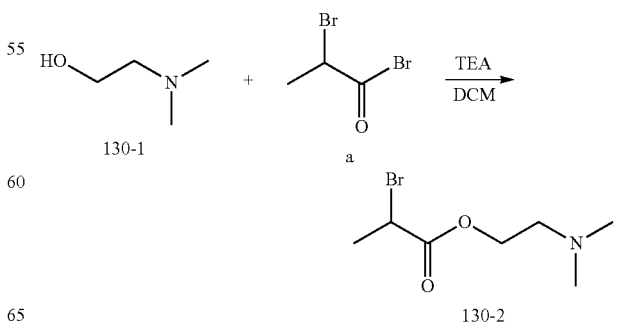

(2) Compound b (400 mg, 1.70 mmol), compound 130-2 (800 mg, crude product) obtained from step (1), a catalytic amount of TBAB (10 mg) and DMF (10 mL) were added to a 50 ml round-bottom flask, heated to 85° C. and reacted for 12 hours. After completed reaction of the starting materials according to LC-MS detection, the reaction solution was cooled to room temperature, and extracted with water (50 ml) and MTBE (50 ml). The organic phase was dried, concentrated, and separated by column chromatography to obtain compound 130 (300 mg, yield 49%).

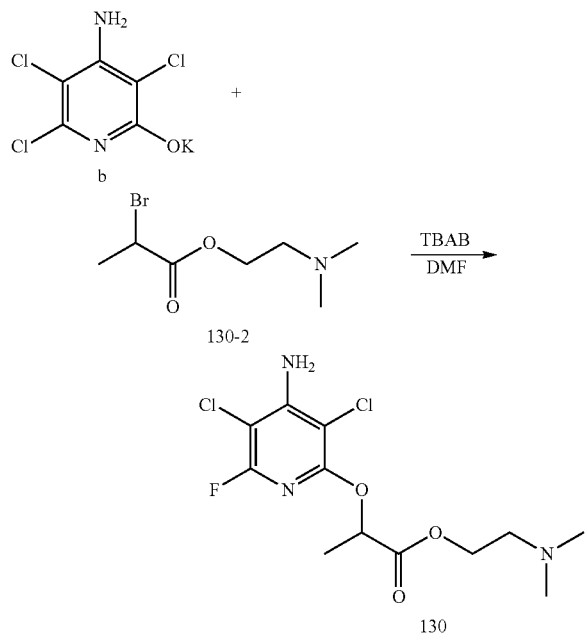

Biological Activity Evaluation:

The activity level standard of harmful plants destruction (i. e. growth inhibition rate) is as follows:

Level 5: the growth inhibition rate is greater than 85%;
Level 4: the growth inhibition rate is equal to or greater than 60% and less than 85%;
Level 3: the growth inhibition rate is equal to or greater than 40% and less than 60%;
Level 2: the growth inhibition rate is equal to or greater than 20% and less than 40%;
Level 1: the growth inhibition rate is equal to or greater than 5% and less than 20%;
Level 0: the growth inhibition rate is less than 5%;
The above described growth inhibition rate is fresh weight inhibition rate.

Post-emergence test experiment: Monocotyledonous and dicotyledonous weed seeds and main crop seeds (i. e. wheat, corn, rice, soybean, cotton, oilseed, millet and sorghum.) were put into a plastic pot loaded with soil. Then covered with 0.5-2 cm soil, the seeds were allowed to grow in good greenhouse environment. The test plants were treated at 2-3 leaf stage 2 weeks after sowing. The test compounds of the invention were dissolved with acetone respectively, then added with tween-80, and using 1.5 liters per hectare of an emulsible concentrate of methyl oleate as a synergist, and diluted by certain amount of water to certain concentration. The solution was sprayed to the plants with a sprayer. Then the plants were cultured for 3 weeks in the greenhouse, and the experiment result of weed controlling effect after 3 weeks was listed in tables 3-4.

TABLE 3

| | Activity test results of compounds (1000 g/ha) | | | | |
|---|---|---|---|---|---|
| No. | Echinochloa crusgalli | Digitaria sanguinalis | Monochoria Vaginalis | Abutilon theophrasti | Galium spurium |
| 1 | 5 | 5 | 5 | 5 | 5 |
| 2 | 5 | 5 | 5 | 5 | 5 |
| 3 | 5 | 5 | 5 | 5 | 5 |
| 4 | 5 | 5 | 5 | 5 | 5 |
| 5 | 5 | 5 | 5 | 5 | 5 |
| 6 | 5 | 5 | 5 | 5 | 5 |
| 7 | 5 | 5 | 5 | 5 | 5 |
| 8 | 5 | 5 | 5 | 5 | 5 |
| 9 | 5 | 5 | 5 | 5 | 5 |
| 10 | 5 | 5 | 5 | 5 | 5 |
| 11 | 5 | 5 | 5 | 5 | 5 |
| 12 | 5 | 5 | 5 | 5 | 5 |
| 13 | 5 | 5 | 5 | 5 | 5 |
| 14 | 5 | 5 | 5 | 5 | 5 |
| 15 | 5 | 5 | 5 | 5 | 5 |
| 16 | 5 | 5 | 5 | 5 | 5 |
| 17 | 5 | 5 | 5 | 5 | 5 |
| 18 | 5 | 5 | 5 | 5 | 5 |
| 19 | 5 | 5 | 5 | 5 | 5 |
| 20 | 5 | 5 | 5 | 5 | 5 |
| 21 | 5 | 5 | 5 | 5 | 5 |
| 22 | 5 | 5 | 5 | 5 | 5 |
| 23 | 5 | 5 | 5 | 5 | 5 |
| 24 | 5 | 5 | 5 | 5 | 5 |
| 25 | | | 5 | 5 | 5 |
| 26 | | | 5 | 5 | 5 |
| 27 | | | 5 | 5 | 5 |
| 28 | | | 5 | 5 | 5 |
| 29 | | | 5 | 5 | 5 |
| 30 | | | 5 | 5 | 5 |
| 31 | | | 5 | 5 | 5 |
| 32 | | | 5 | 5 | 5 |
| 33 | | | 5 | 5 | 5 |
| 34 | | | 5 | 5 | 5 |
| 35 | | | 5 | 5 | 5 |
| 36 | | | 5 | 5 | 5 |
| 37 | | | 5 | 5 | 5 |
| 38 | | | 5 | 5 | 5 |
| 39 | | | 5 | 5 | 5 |
| 40 | | | 5 | 5 | 5 |
| 41 | | | 5 | 5 | 5 |
| 42 | | | 5 | 5 | 5 |
| 43 | | | 5 | 5 | 5 |
| 44 | | | 5 | 5 | 5 |
| 46 | | | 5 | 5 | 5 |
| 47 | | | 5 | 5 | 5 |
| 48 | | | 5 | 5 | 5 |
| 49 | | | 5 | 5 | 5 |
| 50 | | | 5 | 5 | 5 |
| 51 | | | 5 | 5 | 5 |
| 52 | | | 5 | 5 | 5 |
| 53 | | | 5 | 5 | 5 |
| 54 | | | 5 | 5 | 5 |
| 55 | | | 5 | 5 | 5 |
| 56 | | | 5 | 5 | 5 |
| 57 | | | 5 | 5 | 5 |
| 58 | | | 5 | 5 | 5 |
| 59 | | | 5 | 5 | 5 |
| 60 | | | 5 | 5 | 5 |
| 61 | | | 5 | 5 | 5 |
| 62 | | | 5 | 5 | 5 |
| 63 | | | 5 | 5 | 5 |
| 64 | | | 5 | 5 | 5 |
| 65 | | | 5 | 5 | 5 |
| 66 | | | 5 | 5 | 5 |
| 67 | 5 | 5 | 5 | 5 | 5 |
| 68 | 5 | 5 | 5 | 5 | 5 |
| 69 | 5 | 5 | 5 | 5 | 5 |
| 70 | 5 | 5 | 5 | 5 | 5 |
| 71 | 5 | 5 | 5 | 5 | 5 |
| 72 | 5 | 5 | 5 | 5 | 5 |

TABLE 3-continued

Activity test results of compounds (1000 g/ha)

| No. | Echinochloa crusgalli | Digitaria sanguinalis | Monochoria Vaginalis | Abutilon theophrasti | Galium spurium |
|---|---|---|---|---|---|
| 73 | 5 | 5 | 5 | 5 | 5 |
| 74 | 5 | 5 | 5 | 5 | 5 |
| 75 | 5 | 5 | 5 | 5 | 5 |
| 76 | 5 | 5 | 5 | 5 | 5 |
| 77 | 5 | 5 | 5 | 5 | 5 |
| 78 | 5 | 5 | 5 | 5 | 5 |
| 79 | 5 | 5 | 5 | 5 | 5 |
| 80 | 5 | 5 | 5 | 5 | 5 |
| 82 | 5 | 5 | 5 | 5 | 5 |
| 83 | 5 | 5 | 5 | 5 | 5 |
| 84 | 5 | 5 | 5 | 5 | 5 |
| 85 | 5 | 5 | 5 | 5 | 5 |
| 86 | 5 | 5 | 5 | 5 | 5 |
| 87 | 5 | 5 | 5 | 5 | 5 |
| 88 | 5 | 5 | 5 | 5 | 5 |
| 89 | 5 | 5 | 5 | 5 | 5 |
| 90 | 5 | 5 | 5 | 5 | 5 |
| 91 | 5 | 5 | 5 | 5 | 5 |
| 92 | 5 | 5 | 5 | 5 | 5 |
| 93 | 5 | 5 | 5 | 5 | 5 |
| 94 | 5 | 5 | 5 | 5 | 5 |
| 95 | 5 | 5 | 5 | 5 | 5 |
| 96 | 5 | 5 | 5 | 5 | 5 |
| 97 | 5 | 5 | 5 | 5 | 5 |
| 98 | 5 | 5 | 5 | 5 | 5 |
| 99 | 5 | 5 | 5 | 5 | 5 |
| 100 | 5 | 5 | 5 | 5 | 5 |
| 101 | 5 | 5 | 5 | 5 | 5 |
| 102 | 5 | 5 | 5 | 5 | 5 |
| 103 | 5 | 5 | 5 | 5 | 5 |
| 104 | 5 | 5 | 5 | 5 | 5 |
| 105 | 5 | 5 | 5 | 5 | 5 |
| 106 | 5 | 5 | 5 | 5 | 5 |
| 107 | 5 | 5 | 5 | 5 | 5 |
| 108 | 5 | 5 | 5 | 5 | 5 |
| 109 | 5 | 5 | 5 | 5 | 5 |
| 110 | 5 | 5 | 5 | 5 | 5 |
| 111 | 5 | 5 | 5 | 5 | 5 |
| 112 | 5 | 5 | 5 | 5 | 5 |
| 113 | 5 | 5 | 5 | 5 | 5 |
| 114 | 5 | 5 | 5 | 5 | 5 |
| 115 | 5 | 5 | 5 | 5 | 5 |
| 116 | 5 | 5 | 5 | 5 | 5 |
| 117 | 5 | 5 | 5 | 5 | 5 |
| 118 | 5 | 5 | 5 | 5 | 5 |
| 119 | 5 | 5 | 5 | 5 | 5 |
| 120 | 5 | 5 | 5 | 5 | 5 |
| 121 | 5 | 5 | 5 | 5 | 5 |
| 122 | 5 | 5 | 5 | 5 | 5 |
| 123 | 5 | 5 | 5 | 5 | 5 |
| 124 | 5 | 5 | 5 | 5 | 5 |
| 125 | 5 | 5 | 5 | 5 | 5 |
| 126 | 5 | 5 | 5 | 5 | 5 |
| 127 | 5 | 5 | 5 | 5 | 5 |
| 128 | 5 | 5 | 5 | 5 | 5 |
| 129 | 5 | 5 | 5 | 5 | 5 |
| 130 | 5 | 5 | 5 | 5 | 5 |
| 131 | 5 | 5 | 5 | 5 | 5 |
| 132 | 5 | 5 | 5 | 5 | 5 |

TABLE 4

Test results of post-emergence weeds

| No. | Japonica rice | Indica rice | Cyperus iria | Echinochloa crusgalli |
|---|---|---|---|---|
| 2 | 0 | 0 | 5 | 5 |
| 3 | 0 | 0 | 5 | 5 |
| 4 | 0 | 0 | 5 | 5 |
| 12 | 0 | 0 | 5 | 5 |
| 69 | 0 | 0 | 5 | 5 |
| 88 | 0 | 0 | 5 | 5 |
| 100 | 0 | 0 | 5 | 5 |
| 104 | 0 | 0 | 5 | 5 |
| 121 | 0 | 0 | 5 | 5 |
| 125 | 0 | 0 | 5 | 5 |
| 126 | 0 | 0 | 5 | 5 |
| 131 | 0 | 0 | 5 | 5 |
| Control compound A (600 g/ha) | 3 | 3 | 5 | 5 |
| Control compound A (300 g/ha) | 2 | 3 | 4 | 4 |
| Control compound B (600 g/ha) | 2 | 2 | 3 | 2 |
| Bispyribac-sodium (100 g/ha) | 4 | 2 | 2 | 1 |

Note:
the application dose was active ingredient 600 g/ha, plus water 450 kg/ha. *Echinochloa crusgalli* and *Cyperus iria* were collected from Hunan province of China, and were resistant to ALS inhibitor herbicides.

Note: the application dose was active ingredient 600 g/ha, plus water 450 kg/ha. *Echinochloa crusgalli* and *Cyperus iria* were collected from Hunan province of China, and were resistant to ALS inhibitor herbicides.

Control Compound A:

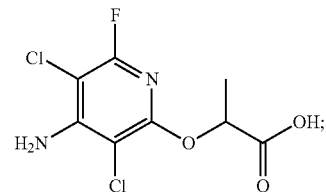 [SMILES: CC(Oc1nc(F)c(Cl)c(N)c1Cl)C(=O)O]

Control Compound B:

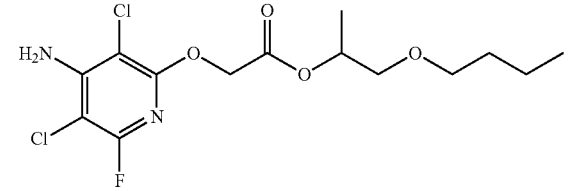 [SMILES: CCCCOCC(C)OC(=O)COc1nc(F)c(Cl)c(N)c1Cl]

The control compound B is a commercial product which has good effect on broadleaf weeds in wheat and can be used to control certain broadleaf weeds even at low rate. However, it is effective only on a few broadleaf weeds in rice at acceptable crop safety (50-100 g/ha) and its efficacy on key grasses such as *Echinochloa crusgalli, Digitaria sanguinalis, Leptochloa chinensis* and *Setaria viridis* in rice is very poor, or even has no effect on these weeds. The control compound A is a known one. Due to poor safety and low selectivity, it is hardly available for commercial application. Unexpectedly, although the structures of the present invention are similar to that of the control compound, the safety of the present invention is greatly improved while retaining the efficacy of the control compound and they have good selectivity to key grasses, broadleaf weeds as well as sedges in rice, thus they have good commercial value, especially for control of ALS resistant weeds considering their outstanding efficacy.

Experiment on Weed Effect in Pre-Emergence Stage

Seeds of monocotyledonous and dicotyledonous weeds and main crops (e. g. wheat, corn, rice, soybean, cotton, oilseed, millet and sorghum) were put into a plastic pot loaded with soil and covered with 0.5-2 cm soil. The test compounds of the present invention was dissolved with acetone, then added with tween-80, diluted by a certain amount of water to reach a certain concentration, and sprayed immediately after sowing. The obtained seeds were incubated for 4 weeks in the greenhouse after spraying and the test results were observed after 3 weeks. It was observed that the herbicide mostly had excellent effect at the application rate of 250 g/ha, especially to weeds such as *Echinochloa crusgalli*, *Digitaria sanguinalis* and *Abutilon theophrasti*, etc. Many compounds had good selectivity for corn, wheat, rice, soybean, oilseed rape, etc.

Through experiments, we found that the compounds of the present invention generally had better weed control effects, especially for major gramineous weeds such as *Echinochloa crusgalli*, *Digitaria sanguinalis*, and *Setaria viridis*, which are widely occurring in corn fields, rice fields and wheat fields, and major broad-leaved weeds such as *Abutilon theophrasti*, *Rorippa indica* and *Bidens pilosa*, and had excellent commercial value. In particular, we noticed that they had extremely high activity against broad-leaved weeds, such as *Rorippa indica*, *Descurainia sophia*, *Capsella bursa-pastoris*, *Lithospermum arvense*, *Galium spurium* and *Stellaria media*, which were resistant to ALS inhibitors.

Transplanted Rice Safety Evaluation and Weed Control Effect Evaluation in Rice Field:

Rice field soil was loaded into a 1/1,000,000 ha pot. The seeds of *Monochoria vaginalis* were sowed and gently covered with soil, then left to stand still in greenhouse in the state of 0.5-1 cm of water storage. It was kept at 3-4 cm of water storage thereafter. The weeds were treated by dripping the WP or SC water diluents prepared according to the common preparation method of the compounds of the present invention with pipette homogeneously to achieve specified effective amount when *Monochoria vaginalis* reached 0.5 leaf stage.

In addition, the rice field soil that loaded into the 1/1,000,000 ha pot was leveled to keep water storage at 3-4 cm depth. The 3-leaf stage rice (japonica rice) was transplanted at 3 cm of transplanting depth the next day. The compound of the present invention was treated by the same way after 5 days of transplantation.

The fertility condition of *Monochoria vaginalis* 14 days and rice 21 days after the treatment of the compound of the invention with the naked eye. Evaluate the weed control effect with the aforementioned activity standard level of 0-5, many compounds exhibited excellent activity and selectivity.

TABLE 5

Test results of activity and safety (1000 g/ha)

| No. | Rice | Monochoria Vaginalis |
|---|---|---|
| 2 | 0 | 5 |
| 3 | 0 | 5 |

TABLE 5-continued

Test results of activity and safety (1000 g/ha)

| No. | Rice | Monochoria Vaginalis |
|---|---|---|
| 4 | 0 | 5 |
| 12 | 0 | 5 |
| 67 | 0 | 5 |
| 75 | 0 | 5 |
| 76 | 0 | 5 |
| 85 | 0 | 5 |
| 120 | 0 | 5 |
| 128 | 0 | 5 |
| Penoxsulam (50 g/ha) | 1 | 1 |

Note:
The seeds of *Monochoria vaginalis* were collected from Heilongjing Province of China.

Note: The seeds of *Monochoria vaginalis* were collected from Heilongjing Province of China. Tests indicated that the weeds were resistant to common rate of pyrazosulfuron-ethyl and penoxsulam.

It can be seen from the experiments that the compounds of the present invention had excellent activity against weeds having an anti-ALS inhibiting activity which cause a serious challenge in production, and can solve the increasingly serious problem of resistance.

Broadleaf crops are very sensitive to hormonal herbicides, therefore crop injuries are more likely to occur in case of spray drifting. Tests were conducted in gentle breeze for the compounds of the present invention. The formulation of the compounds of the present invention was applied by DJI unmanned gyroplane with application height of 1 m and water volume of 20 kg/ha. The use rate was 600 g/ha. The active ingredient was dissolved by acetone and diluted to aqueous solution of Tween 80. There's a soybean field at 10 meters from the application area and the height of soybean plants were about 15 cm at the application time. The control compound C was applied in the same rate and under same conditions.

TABLE 6

Test results of activity

| No. | Soybean |
|---|---|
| 1 | 0 |
| 2 | 0 |
| 3 | 0 |
| 4 | 0 |
| 27 | 0 |
| 41 | 0 |
| 43 | 0 |
| 46 | 0 |
| 50 | 0 |
| 53 | 0 |
| 54 | 0 |
| 82 | 0 |
| 83 | 0 |
| 113 | 0 |
| 131 | 0 |
| Control compound C | 3 |

Note: Compound C is

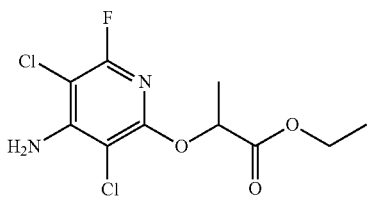

It can be seen that the compounds of the present disclosure are not only safe for soybean, but also safe for surrounding crops, and will not cause damage to sensitive broad-leaved crops due to drift problems under low wind conditions. Although the structure of the control compound is similar to the compounds of the present disclosure, it is not safe for soybean, and at the same time, it is easy to cause phytotoxicity to the surrounding sensitive broad-leaved crops. With the large-scale promotion of unmanned aerial vehicles, there is a need for the herbicides of the present disclosure, which are safer to the environment.

At the same time, it is found after several tests that the compound and the composition of the present invention have good selectivity to many gramineae weeds such as *Zoysia japonica, Cynodon dactylon, Festuca elata, Poa annua, Lolium perenne* and *Paspalum vaginatum* etc, and is able to control many important gramineous weeds and broad-leaved weeds. The compound also shows excellent selectivity and commercial value in the tests on wheat, corn, rice, sugarcane, soybean, cotton, oil sunflower, potato, orchards and vegetables in different herbicide application methods.

The invention claimed is:

1. A pyridyloxy carboxylate derivative represented by formula I,

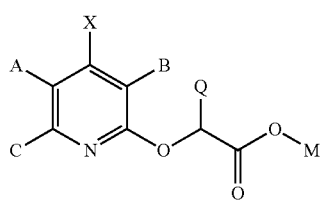

wherein, A and B each independently represent halogen, alkyl optionally substituted by halogen, or cycloalkyl optionally substituted by halogen;

C represents hydrogen, halogen, alkyl or haloalkyl;

Q represents halogen, cyano, cyanoalkyl, hydroxyalkyl, amino, nitro, formyl, alkyl optionally substituted by halogen, alkenyl optionally substituted by halogen, alkynyl optionally substituted by halogen, cycloalkyl optionally substituted by halogen, alkoxy optionally substituted by halogen, alkylthio optionally substituted by halogen, alkylcarbonyl optionally substituted by halogen, alkoxycarbonyl optionally substituted by halogen, alkylaminoalkyl optionally substituted by halogen, alkoxyalkyl optionally substituted by halogen, unsubstituted or substituted aryl, unsubstituted or substituted heteroaryl, unsubstituted or substituted arylalkyl, or unsubstituted or substituted heteroarylalkyl;

M represents -alkyl-R, -haloalkyl-R, or

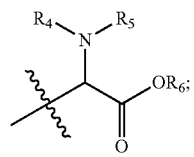

R represents

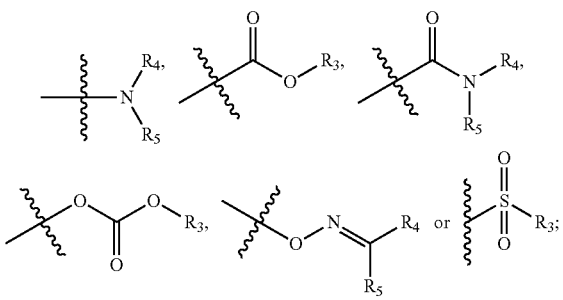

$R_3$ represents hydrogen, alkyl, alkenyl, alkynyl, cycloalkyl, cycloalkylalkyl, unsubstituted or substituted heterocyclyl, unsubstituted or substituted aryl, unsubstituted or substituted heteroaryl, unsubstituted or substituted heterocyclylalkyl, unsubstituted or substituted arylalkyl, or unsubstituted or substituted heteroarylalkyl;

$R_4$, $R_5$, and $R_6$ each independently represent hydrogen, alkyl, alkenyl, alkynyl, cycloalkyl, cycloalkylalkyl, alkoxy, alkoxycarbonyl, unsubstituted or substituted heterocyclyl, unsubstituted or substituted aryl, unsubstituted or substituted heteroaryl, unsubstituted or substituted heterocyclylalkyl, unsubstituted or substituted arylalkyl, or unsubstituted or substituted heteroarylalkyl;

X represents nitro, $N=CR_{21}NR_{22}R_{23}$, $N=CR_{24}OR_{25}$, $NR_1R_2$, or a 5- or 6-membered saturated or unsaturated ring comprising a nitrogen atom and optionally one or more heteroatoms selected from oxygen atom, sulfur atom, and nitrogen atom; wherein the 5- or 6-membered saturated or unsaturated ring is unsubstituted or substituted by 1-2 groups independently selected from halogen, alkyl, alkoxy, haloalkoxy, alkylthio, haloalkylthio, amino, alkylamino, dialkylamino and alkoxycarbonyl; wherein $R_1$ represents H, alkyl optionally substituted by 1-2 $R_{11}$, alkenyl optionally substituted by 1-2 $R_{11}$, alkynyl optionally substituted by 1-2 $R_{11}$, —$COR_{12}$, nitro, $OR_{13}$, $SO_2R_{14}$, $NR_{15}R_{16}$, $N=CR_{17}R_{18}$,

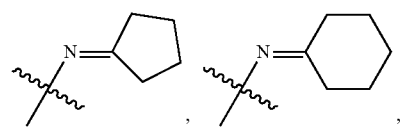 [SMILES: *N=C1CCCC1 ; *N=C1CCCCC1]

alkylcarbamoyl, dialkylcarbamoyl, trialkylsilyl, or dialkylphosphono;

$R_2$ represents H, alkyl optionally substituted by 1-2 $R_{11}$, or —$COR_{12}$;

wherein each $R_{11}$ independently represents halogen, hydroxy, alkoxy, haloalkoxy, alkylthio, haloalkylthio, amino, alkylamino, dialkylamino, alkoxycarbonyl, unsubstituted or substituted aryl, or unsubstituted or substituted heteroaryl;

$R_{12}$ represents H, alkyl, haloalkyl, alkoxy, phenyl, phenoxy, or benzyloxy;

$R_{13}$ represents H, alkyl, haloalkyl, phenyl, benzyl or $CHR_{31}C(O)OR_{32}$; $R_{31}$ represents H, alkyl, or alkoxy; $R_{32}$ represents H, alkyl, or benzyl;

$R_{14}$ represents alkyl or haloalkyl;

$R_{15}$ represents H, alkyl, formyl, alkylacyl, haloalkylacyl, alkoxycarbonyl, phenylcarbonyl, phenoxycarbonyl, or benzyloxycarbonyl; $R_{16}$ represents H or alkyl;

$R_{17}$ represents H, alkyl, or phenyl optionally substituted by 1-3 groups selected from halogen, alkyl, and alkoxy;

$R_{18}$ represents H or alkyl;

$R_{21}$ and $R_{24}$ each independently represent H or alkyl;

$R_{22}$ and $R_{23}$ each independently represent H or alkyl; or $R_{22}$ and $R_{23}$ are optionally connected, together with the nitrogen atom to which they are bonded, to form a 5- or 6-membered saturated or unsaturated ring, wherein the 5- or 6-membered saturated or unsaturated ring optionally comprises an oxygen atom, sulfur atom, or other nitrogen atom;

$R_{25}$ represents alkyl.

2. The pyridyloxy carboxylate derivative according to claim 1, wherein A and B each independently represent halogen, C1-C8 alkyl optionally substituted by halogen, or C3-C8 cycloalkyl optionally substituted by halogen;

C represents hydrogen, halogen, C1-C8 alkyl, or halo C1-C8 alkyl;

Q represents halogen, cyano, cyano C1-C8 alkyl, hydroxy C1-C8 alkyl, amino, nitro, formyl, C1-C8 alkyl optionally substituted by halogen, C2-C8 alkenyl optionally substituted by halogen, C2-C8 alkynyl optionally substituted by halogen, C3-C8 cycloalkyl optionally substituted by halogen, C1-C8 alkoxy optionally substituted by halogen, C1-C8 alkylthio optionally substituted by halogen, C1-C8 alkylcarbonyl optionally substituted by halogen, C1-C8 alkoxycarbonyl optionally substituted by halogen, C1-C8 alkylamino C1-C8 alkyl optionally substituted by halogen, C1-C8 alkoxy C1-C8 alkyl optionally substituted by halogen, unsubstituted or substituted aryl, unsubstituted or substituted heteroaryl, unsubstituted or substituted aryl C1-C8 alkyl, or unsubstituted or substituted heteroaryl C1-C8 alkyl;

M represents —(C1-C8)alkyl-R, -halo(C1-C8)alkyl-R or

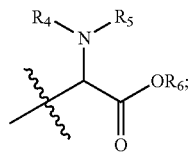

R represents

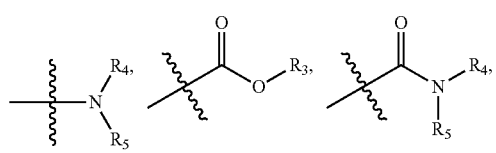

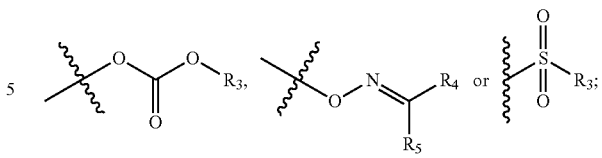

$R_3$ represents hydrogen, C1-C8 alkyl, C2-C8 alkenyl, C2-C8 alkynyl, C3-C8 cycloalkyl, C3-C8 cycloalkyl C1-C8 alkyl, unsubstituted or substituted heterocyclyl, unsubstituted or substituted aryl, unsubstituted or substituted heteroaryl, unsubstituted or substituted heterocyclyl C1-C8 alkyl, unsubstituted or substituted aryl C1-C8 alkyl, or unsubstituted or substituted heteroaryl C1-C8 alkyl;

$R_4$, $R_5$, and $R_6$ each independently represent hydrogen, C1-C8 alkyl, C2-C8 alkenyl, C2-C8 alkynyl, C3-C8 cycloalkyl, C3-C8 cycloalkyl C1-C8 alkyl, C1-C8 alkoxy, C1-C8 alkoxycarbonyl, unsubstituted or substituted heterocyclyl, unsubstituted or substituted aryl, unsubstituted or substituted heteroaryl, unsubstituted or substituted heterocyclyl C1-C8 alkyl, unsubstituted or substituted aryl C1-C8 alkyl, or unsubstituted or substituted heteroaryl C1-C8 alkyl;

X represents nitro, $N=CR_{21}NR_{22}R_{23}$, $N=CR_{24}OR_{25}$, $NR_1R_2$, unsubstituted or substituted

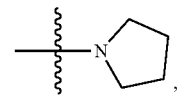

unsubstituted or substituted

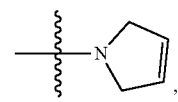

unsubstituted or substituted

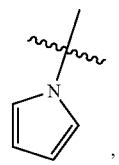

unsubstituted or substituted

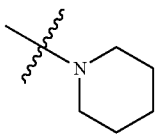 [SMILES: *N1CCCCC1]

or unsubstituted or substituted

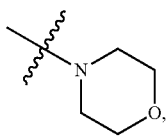 [SMILES: *N1CCOCC1]

wherein the substituent is 1 or 2 groups independently selected from halogen, C1-C8 alkyl, C1-C8 alkoxy, halo C1-C8 alkoxy, C1-C8 alkylthio, halo C1-C8 alkylthio, amino, C1-C8 alkylamino, di-C1-C8 alkylamino and C1-C8 alkoxycarbonyl; wherein $R_1$ represents H, C1-C8 alkyl optionally substituted by 1-2 $R_{11}$, C2-C8 alkenyl optionally substituted by 1-2 $R_{11}$, C2-C8 alkynyl optionally substituted by 1-2 $R_{11}$, —$COR_{12}$, nitro, $OR_{13}$, $SO_2R_{14}$, $NR_{15}R_{16}$, $N=CR_{17}R_{18}$,

C1-C8 alkylcarbamoyl, di-C1-C8 alkylcarbamoyl, tri-C1-C8 alkylsilyl, or di-C1-C8 alkylphosphono;

$R_2$ represents H, C1-C8 alkyl optionally substituted by 1-2 $R_{11}$, or —$COR_{12}$;

wherein each $R_{11}$ independently represents halogen, hydroxy, C1-C8 alkoxy, halo C1-C8 alkoxy, C1-C8 alkylthio, halo C1-C8 alkylthio, amino, C1-C8 alkylamino, di-C1-C8 alkylamino, C1-C8 alkoxycarbonyl, unsubstituted or substituted phenyl, unsubstituted or substituted naphthyl, unsubstituted or substituted

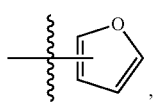

unsubstituted or substituted

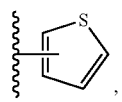

unsubstituted or substituted

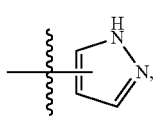

unsubstituted or substituted

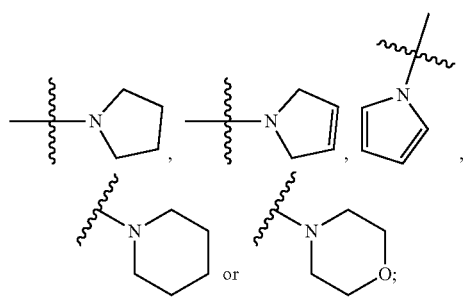

unsubstituted or substituted

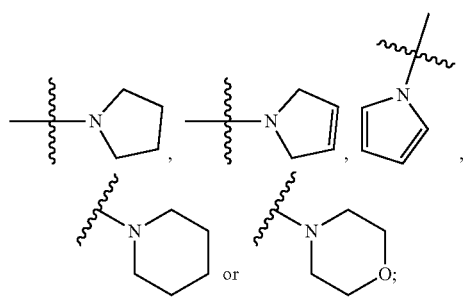

or unsubstituted or substituted

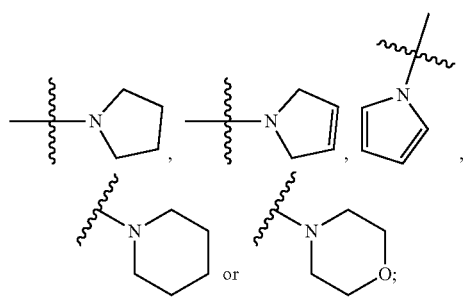

wherein the substituents are 1-3 groups selected from halogen, C1-C8 alkyl, halo C1-8 alkyl, C1-C8 alkoxy, and nitro;

$R_{12}$ represents H, C1-C18 alkyl, halo C1-C8 alkyl, C1-C8 alkoxy, phenyl, phenoxy, or benzyloxy;

$R_{13}$ represents H, C1-C8 alkyl, halo C1-C8 alkyl, phenyl, benzyl, or $CHR_{31}C(O)OR_{32}$;

$R_{31}$ represents H, C1-C8 alkyl, or C1-C8 alkoxy; $R_{32}$ represents H, C1-C8 alkyl, or benzyl;

$R_{14}$ represents C1-C8 alkyl or halo C1-C8 alkyl;

$R_{15}$ represents H, C1-C8 alkyl, formyl, C1-C8 alkylacyl, halo C1-C8 alkylacyl, C1-C8 alkoxycarbonyl, phenylcarbonyl, phenoxycarbonyl, or benzyloxycarbonyl; $R_{16}$ represents H or C1-C8 alkyl;

$R_{17}$ represents H, C1-C8 alkyl, or phenyl optionally substituted by 1-3 groups selected from halogen, C1-C8 alkyl, and C1-C8 alkoxy;

$R_{18}$ represents H or C1-C8 alkyl;

$R_{21}$ and $R_{24}$ each independently represent H or C1-C8 alkyl;

$R_{22}$ and $R_{23}$ each independently represent H or C1-C8 alkyl; or $R_{22}$ and $R_{23}$ are optionally connected, together with the nitrogen atom to which they are bonded, to form

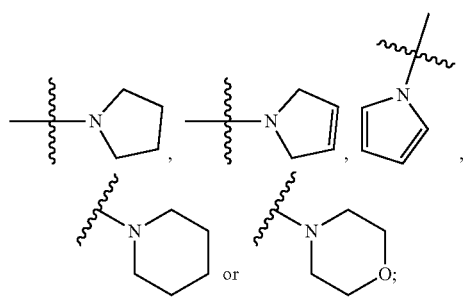

$R_{25}$ represents C1-C8 alkyl;

the term "heterocyclyl" refers to

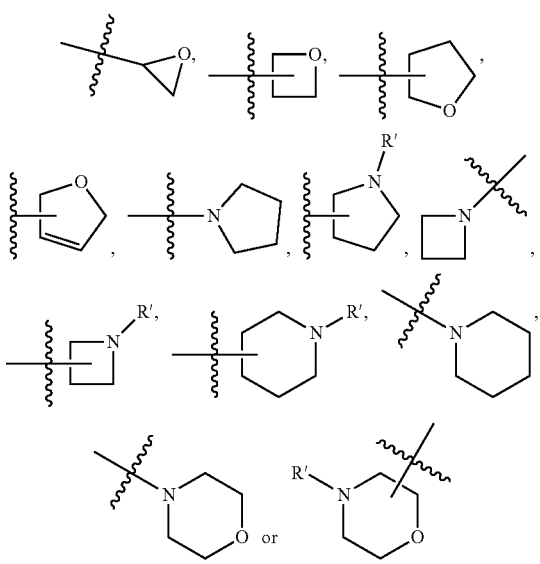

with 0, 1 or 2 substituents that are oxo groups; the term "aryl" refers to phenyl or naphthyl; the term "heteroaryl" refers to

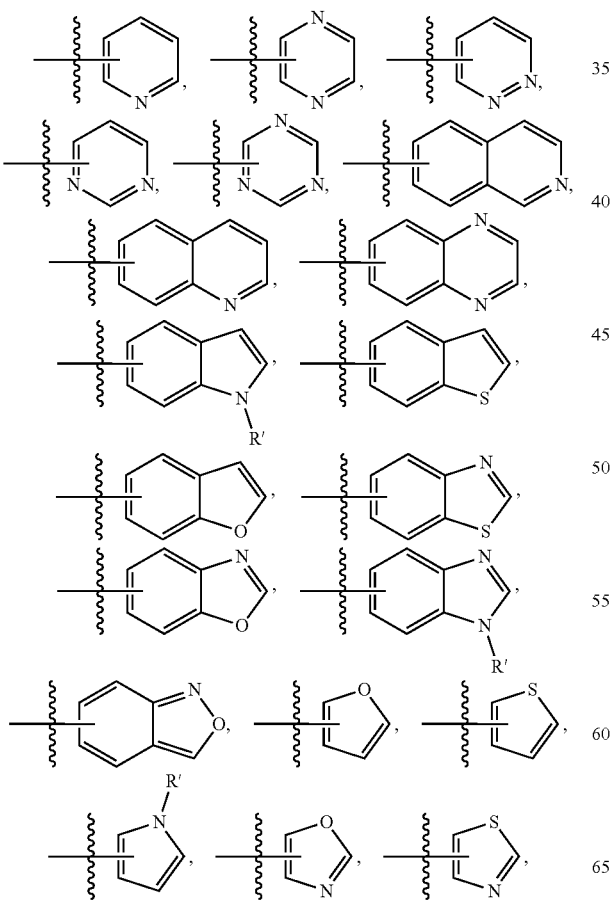

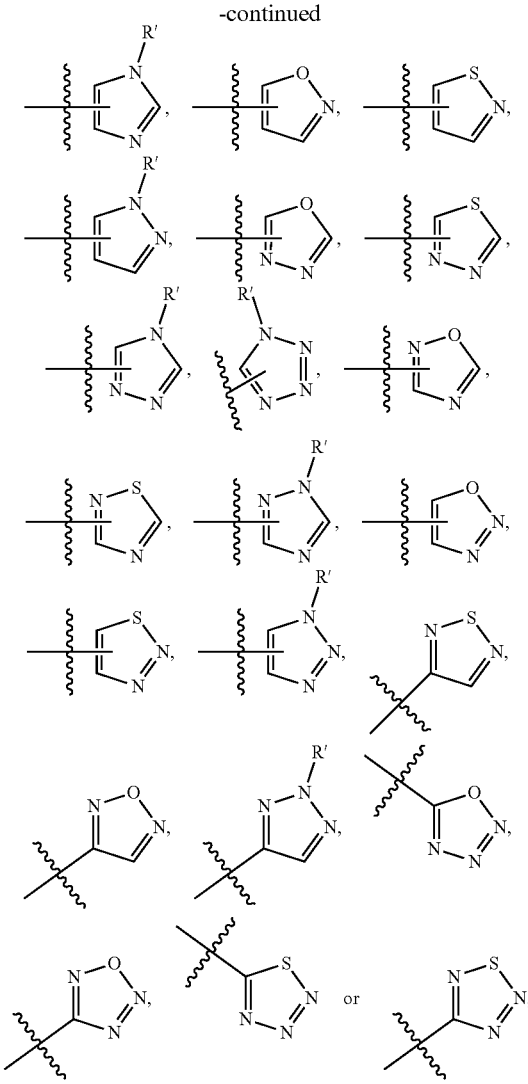

each of which is optionally substituted by at least one group selected from: halogen, nitro, cyano, thiocyano, hydroxy, carboxy, mercapto, formyl, phenyl optionally substituted by at least one group selected from halogen, alkyl and alkoxy, benzyl optionally substituted by at least one group selected from halogen, alkyl and alkoxy, benzyloxy optionally substituted by at least one group selected from halogen, alkyl and alkoxy, phenoxy optionally substituted by at least one group selected from halogen, alkyl and alkoxy, alkyl optionally substituted by halogen, alkenyl optionally substituted by halogen, alkynyl optionally substituted by halogen, cycloalkyl optionally substituted by halogen, cycloalkylalkyl optionally substituted by halogen, OR" optionally substituted by halogen, SR" optionally substituted by halogen, -alkyl-OR" optionally substituted by halogen, -alkyl-SR" optionally substituted by halogen, COR" optionally substituted by halogen, COOR" optionally substituted by halogen, COSR" optionally substituted by halogen, SOR" optionally substituted by halogen, SO₂R" optionally substituted by halogen, OCOR" optionally substituted by halogen, or SCOR" optionally substituted by halogen, amino substituted by one or two groups selected from hydrogen, alkyl, alkenyl, alkynyl, cycloalkyl, cycloalkylalkyl, phenyl, benzyl, benzyloxy, phenoxy, COR'', COOR'', SO2R'' and OR'', and aminocarbonyl substituted by one or two groups selected from hydrogen, alkyl, alkenyl, alkynyl, cycloalkyl, cycloalkylalkyl, phenyl, benzyl, benzyloxy, phenoxy, COR'', COOR'', SO$_2$R'' and OR'';

each R' independently represents hydrogen, nitro, hydroxy, amino, alkyl optionally substituted by halogen, alkenyl optionally substituted by halogen, alkynyl optionally substituted by halogen, cycloalkyl optionally substituted by halogen, cycloalkenyl optionally substituted by halogen, cycloalkylalkyl optionally substituted by halogen, alkoxy optionally substituted by halogen, alkenyloxy optionally substituted by halogen, alkynyloxy optionally substituted by halogen, cycloalkyloxy optionally substituted by halogen, alkoxyalkyl optionally substituted by halogen, alkoxycarbonyl optionally substituted by halogen, alkylthiocarbonyl optionally substituted by halogen, alkylsulfonyl optionally substituted by halogen, alkylsulfonylalkyl optionally substituted by halogen, alkylcarbonyl optionally substituted by halogen, alkylcarbonylalkyl optionally substituted by halogen, alkylacyloxy optionally substituted by halogen, alkylamino optionally substituted by halogen, alkylaminocarbonyl optionally substituted by halogen, alkoxyaminocarbonyl optionally substituted by halogen, alkoxycarbonylalkyl optionally substituted by halogen, alkylaminocarbonylalkyl optionally substituted by halogen, trialkylsilyl optionally substituted by halogen, or dialkylphosphono optionally substituted by halogen;

each R'' independently represents hydrogen, alkyl, alkenyl, alkynyl, cycloalkyl, or cycloalkylalkyl.

3. The pyridyloxy carboxylate derivative according to claim 2, wherein A and B each independently represent halogen, C1-C6 alkyl optionally substituted by halogen, or C3-C6 cycloalkyl optionally substituted by halogen;

C represents hydrogen, halogen, C1-C6 alkyl, or halo C1-C6 alkyl;

Q represents halogen, cyano, cyano C1-C6 alkyl, hydroxy C1-C6 alkyl, amino, nitro, formyl, C1-C6 alkyl optionally substituted by halogen, C2-C6 alkenyl optionally substituted by halogen, C2-C6 alkynyl optionally substituted by halogen, C3-C6 cycloalkyl optionally substituted by halogen, C1-C6 alkoxy optionally substituted by halogen, C1-C6 alkylthio optionally substituted by halogen, C1-C6 alkylcarbonyl optionally substituted by halogen, C1-C6 alkoxycarbonyl optionally substituted by halogen, C1-C6 alkylamino C1-C6 alkyl optionally substituted by halogen, C1-C6 alkoxy C1-C6 alkyl optionally substituted by halogen, unsubstituted or substituted aryl, unsubstituted or substituted heteroaryl, unsubstituted or substituted aryl C1-C6 alkyl, or unsubstituted or substituted heteroaryl C1-C6 alkyl;

M represents —(C1-C6)alkyl-R, -halo(C1-C6)alkyl-R or

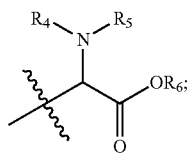

R represents

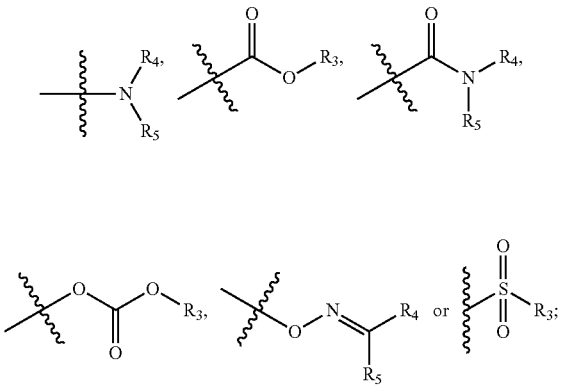

$R_3$ represents hydrogen, C1-C6 alkyl, C2-C6 alkenyl, C2-C6 alkynyl, C3-C6 cycloalkyl, C3-C6 cycloalkyl C1-C6 alkyl, unsubstituted or substituted heterocyclyl, unsubstituted or substituted aryl, unsubstituted or substituted heteroaryl, unsubstituted or substituted heterocyclyl C1-C6 alkyl, unsubstituted or substituted aryl C1-C6 alkyl, or unsubstituted or substituted heteroaryl C1-C6 alkyl;

$R_4$, $R_5$, and $R_6$ each independently represent hydrogen, C1-C6 alkyl, C2-C6 alkenyl, C2-C6 alkynyl, C3-C6 cycloalkyl, C3-C6 cycloalkyl C1-C6 alkyl, C1-C6 alkoxy, C1-C6 alkoxycarbonyl, unsubstituted or substituted heterocyclyl, unsubstituted or substituted aryl, unsubstituted or substituted heteroaryl, unsubstituted or substituted heterocyclyl C1-C6 alkyl, unsubstituted or substituted aryl C1-C6 alkyl, or unsubstituted or substituted heteroaryl C1-C6 alkyl;

X represents nitro, N=CR$_{21}$NR$_{22}$R$_{23}$, N=CR$_{24}$OR$_{25}$, NR$_1$R$_2$, unsubstituted or substituted

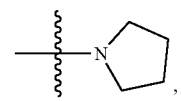

unsubstituted or substituted

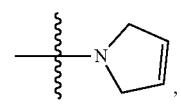

unsubstituted or substituted

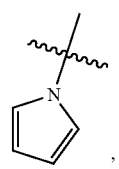

unsubstituted or substituted

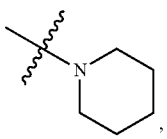

or unsubstituted or substituted

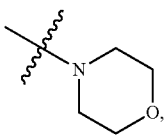

wherein the substituents are 1 or 2 groups independently selected from halogen, C1-C6 alkyl, C1-C6 alkoxy, halo C1-C6 alkoxy, C1-C6 alkylthio, halo C1-C6 alkylthio, amino, C1-C6 alkylamino, di-C1-C6 alkylamino and C1-C6 alkoxycarbonyl; wherein $R_1$ represents H, C1-C6 alkyl optionally substituted by 1-2 $R_{11}$, C2-C6 alkenyl optionally substituted by 1-2 $R_{11}$, C2-C6 alkynyl optionally substituted by 1-2 $R_{11}$, —$COR_{12}$, nitro, $OR_{13}$, $SO_2R_{14}$, $NR_{15}R_{16}$, $N=CR_{17}R_{18}$,

C6 alkylcarbamoyl, di-C1-C6 alkylcarbamoyl, tri-C1-C6 alkylsilyl, or di-C1-C6 alkylphosphono; $R_2$ represents H, C1-C6 alkyl optionally substituted by 1-2 $R_11$, or —$COR_{12}$;

wherein each $R_{11}$ independently represents halogen, hydroxy, C1-C6 alkoxy, halo C1-C6 alkoxy, C1-C6 alkylthio, halo C1-C6 alkylthio, amino, C1-C6 alkylamino, di-C1-C6 alkylamino, C1-C6 alkoxycarbonyl, unsubstituted or substituted phenyl, unsubstituted or substituted naphthyl, unsubstituted or substituted

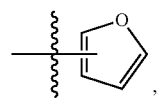

unsubstituted or substituted

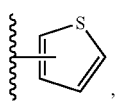

unsubstituted or substituted

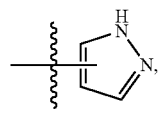

unsubstituted or substituted

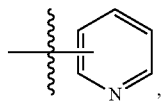

unsubstituted or substituted

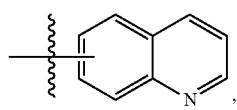

unsubstituted or substituted

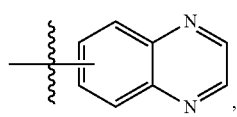

wherein the substituents are 1-3 groups selected from halogen, C1-C6 alkyl, halo C1-C6 alkyl, C1-C6 alkoxy, and nitro;

$R_{12}$ represents H, C1-C14 alkyl, halo C1-C6 alkyl, C1-C6 alkoxy, phenyl, phenoxy, or benzyloxy;

$R_{13}$ represents H, C1-C6 alkyl, halo C1-C6 alkyl, phenyl, benzyl, or $CHR_{31}C(O)OR_{32}$;

$R_{31}$ represents H, C1-C6 alkyl, or C1-C6 alkoxy; $R_{32}$ represents H, C1-C6 alkyl, or benzyl;

$R_{14}$ represents C1-C6 alkyl or halo C1-C6 alkyl;

$R_{15}$ represents H, C1-C6 alkyl, formyl, C1-C6 alkylacyl, halo C1-C6 alkylacyl, C1-C6 alkoxycarbonyl, phenylcarbonyl, phenoxycarbonyl, or benzyloxycarbonyl; $R_{16}$ represents H or C1-C6 alkyl;

$R_{17}$ represents H, C1-C6 alkyl, or phenyl optionally substituted by 1-3 groups selected from halogen, C1-C6 alkyl, and C1-C6 alkoxy;

$R_{18}$ represents H or C1-C6 alkyl;

$R_{21}$ and $R_{24}$ each independently represent H or C1-C6 alkyl;

$R_{22}$ and $R_{23}$ each independently represent H or C1-C6 alkyl; or $R_{22}$ and $R_{23}$ are optionally connected, together with the nitrogen atom to which they are bonded, to form

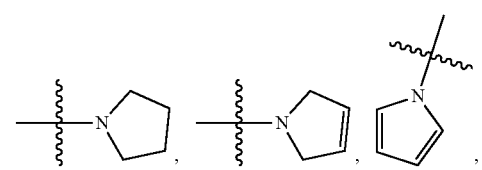

-continued

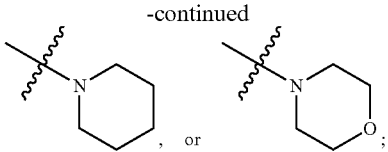

$R_{25}$ represents C1-C6 alkyl;
the term "heterocyclyl" refers to

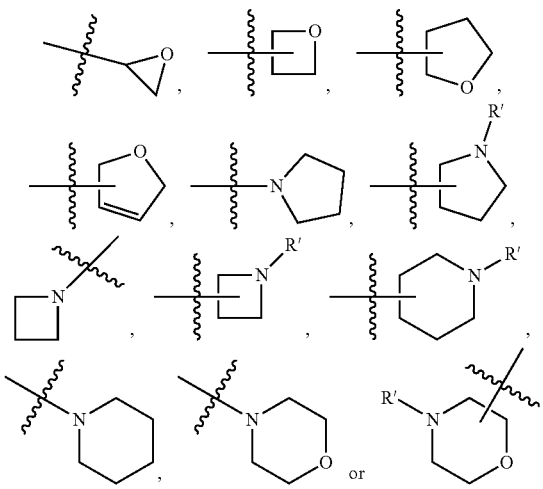

with 0, 1 or 2 substituents that are oxo groups; the term "aryl" refers to phenyl or naphthyl; the term "heteroaryl" refers to

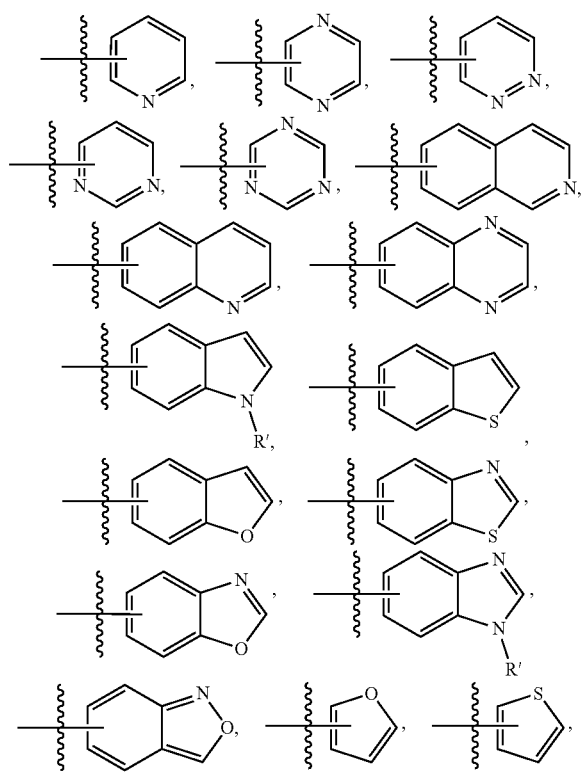

-continued

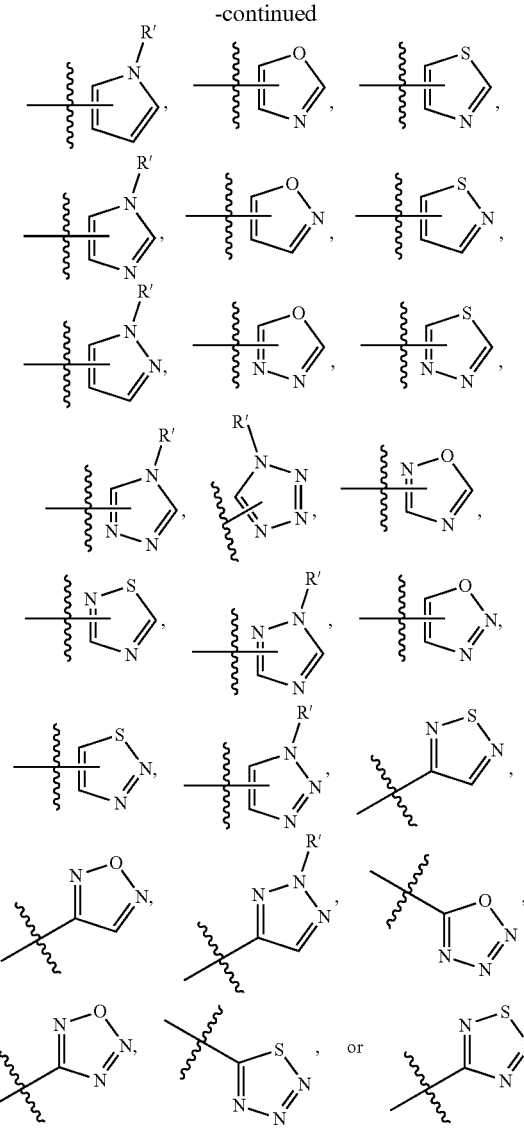

each of which is substituted by 0, 1, 2 or 3 groups selected from: halogen, nitro, cyano, thiocyano, hydroxy, carboxy, mercapto, formyl, phenyl optionally substituted by at least one group selected from halogen, C1-C6 alkyl and C1-C6 alkoxy, benzyl optionally substituted by at least one group selected from halogen, C1-C6 alkyl and C1-C6 alkoxy, benzyloxy optionally substituted by at least one group selected from halogen, C1-C6 alkyl and C1-C6 alkoxy, phenoxy optionally substituted by at least one group selected from halogen, C1-C6 alkyl and C1-C6 alkoxy, C1-C6 alkyl optionally substituted by halogen, C2-C6 alkenyl optionally substituted by halogen, C2-C6 alkynyl optionally substituted by halogen, C3-C6 cycloalkyl optionally substituted by halogen, C3-C6 cycloalkyl C1-C6 alkyl optionally substituted by halogen, OR" optionally substituted by halogen, SR" optionally substituted by halogen, —(C1-C6)alkyl-OR" optionally substituted by halogen, —(C1-C6)alkyl-SR" optionally substituted by halogen, COR" optionally substituted by halogen, COOR" optionally substituted by halogen, COSR" optionally substituted by halogen, SOR" optionally substituted by halogen, SO₂R" optionally substituted by halogen, OCOR" optionally substituted by halogen, SCOR" optionally substituted by halogen, amino substituted by one or two groups selected from the group consisting of hydrogen, C1-C6 alkyl, C2-C6 alkenyl, C2-C6 alkynyl, C3-C6 cycloalkyl, C3-C6 cycloalkyl C1-C6 alkyl, phenyl, benzyl, benzyloxy, phenoxy, COR", COOR", SO₂R" and OR", and aminocarbonyl substituted by one or two groups selected from hydrogen, C1-C6 alkyl, C2-C6 alkenyl, C2-C6 alkynyl, C3-C6 cycloalkyl, C3-C6 cycloalkyl C1-C6 alkyl, phenyl, benzyl, benzyloxy, phenoxy, COR", COOR", SO₂R", and OR", each R' independently represents hydrogen, nitro, hydroxy, amino, C1-C6 alkyl optionally substituted by fluoro, chloro or bromo, C2-C6 alkenyl optionally substituted by fluoro, chloro or bromo, C2-C6 alkynyl optionally substituted by fluoro, chloro or bromo, C3-C6 cycloalkyl optionally substituted by fluoro, chloro or bromo, C3-C6 cyclo alkenyl optionally substituted by fluoro, chloro or bromo, C3-C6 cycloalkyl C1-C6 alkyl optionally substituted by fluoro, chloro or bromo, C1-C6 alkoxy optionally substituted by fluoro, chloro or bromo, C2-C6 alkenyloxy optionally substituted by fluoro, chloro or bromo, C2-C6 alkynyloxy optionally substituted by fluoro, chloro or bromo, C3-C6 cycloalkyloxy optionally substituted by fluoro, chloro or bromo, C1-C6 alkoxy C1-C6 alkyl optionally substituted by fluoro, chloro or bromo, C1-C6 alkoxycarbonyl optionally substituted by fluoro, chloro or bromo, C1-C6 alkylthiocarbonyl optionally substituted by fluoro, chloro or bromo, C1-C6 alkylsulfonyl optionally substituted by fluoro, chloro or bromo, C1-C6 alkylsulfonyl C1-C6 alkyl optionally substituted by fluoro, chloro or bromo, C1-C6 alkylcarbonyl optionally substituted by fluoro, chloro or bromo, C1-C6 alkylcarbonyl C1-C6 alkyl optionally substituted by fluoro, chloro or bromo, C1-C6 alkylacyloxy optionally substituted by fluoro, chloro or bromo, C1-C6 alkylamino optionally substituted by fluoro, chloro or bromo, C1-C6 alkylaminocarbonyl optionally substituted by fluoro, chloro or bromo, C1-C6 alkoxyaminocarbonyl optionally substituted by fluoro, chloro or bromo, C1-C6 alkoxycarbonyl C1-C6 alkyl optionally substituted by fluoro, chloro or bromo, C1-C6 alkylaminocarbonyl C1-C6 alkyl optionally substituted by fluoro, chloro or bromo, tri-C1-C6 alkylsilyl optionally substituted by fluoro, chloro or bromo, or di-C1-C6 alkylphosphono optionally substituted by fluoro, chloro or bromo;

each R" independently represents hydrogen, C1-C6 alkyl, C2-C6 alkenyl, C2-C6 alkynyl, C3-C6 cycloalkyl, or C3-C6 cycloalkyl C1-C6 alkyl.

4. The pyridyloxy carboxylate derivative according to claim 3, wherein A and B each independently represent halogen, C1-C6 alkyl, halo C1-C6 alkyl, or C3-C6 cycloalkyl;

C represents hydrogen, halogen, C1-C6 alkyl, or halo C1-C6 alkyl;

Q represents C1-C6 alkyl, halo C1-C6 alkyl, C3-C6 cycloalkyl, C2-C6 alkenyl, C2-C6 alkynyl, halogen, cyano, amino, nitro, formyl, C1-C6 alkoxy, C1-C6 alkylthio, C1-C6 alkoxycarbonyl, hydroxy C1-C6 alkyl, C1-C6 alkoxy C1-C2 alkyl, cyano C1-C2 alkyl, C1-C6 alkylamino C1-C2 alkyl, benzyl, naphthyl, furyl, thienyl, thiazolyl, pyridyl, pyrimidinyl,

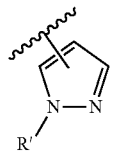

optionally substituted by C1-C6 alkyl, or phenyl optionally substituted by at least one group selected from C1-C6 alkyl, halo C1-C6 alkyl, halogen, and C1-C6 alkoxy;

M represents —(C1-C6)alkyl-R, -halo(C1-C6)alkyl-R, or

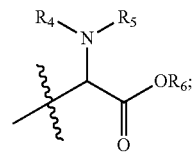

R represents

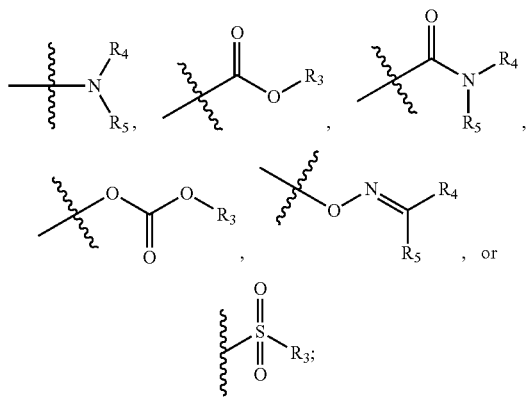

R₃ represents hydrogen, C1-C6 alkyl, C2-C6 alkenyl, C2-C6 alkynyl, C3-C6 cycloalkyl, C3-C6 cycloalkyl C1-C6 alkyl, unsubstituted or substituted phenyl, unsubstituted or substituted naphthyl, unsubstituted or substituted benzyl, unsubstituted or substituted

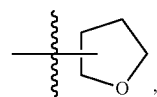

unsubstituted or substituted

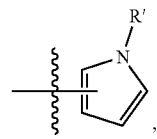

unsubstituted or substituted

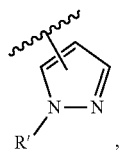, unsubstituted or substituted

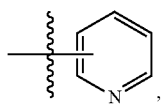, unsubstituted or substituted

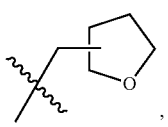, unsubstituted or substituted

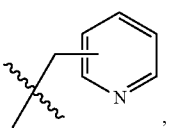, or unsubstituted or substituted

,

Wherein the substituent is at least one group selected from C1-C6 alkyl, C1-C6 alkoxy, halogen, and halo C1-C6 alkyl;

$R_4$, $R_5$, and $R_6$ each independently represent hydrogen, C1-C6 alkyl, C2-C6 alkenyl, C2-C6 alkynyl, C3-C6 cycloalkyl, C3-C6 cycloalkyl C1-C6 alkyl, C1-C6 alkoxy, C1-C6 alkoxycarbonyl, unsubstituted or substituted phenyl, unsubstituted or substituted naphthyl, unsubstituted or substituted benzyl, unsubstituted or substituted

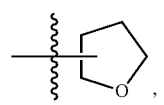, unsubstituted or substituted

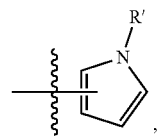, unsubstituted or substituted

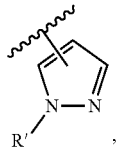, unsubstituted or substituted

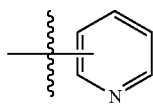, unsubstituted or substituted

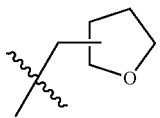, unsubstituted or substituted

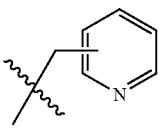, or unsubstituted or substituted

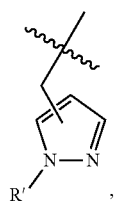, wherein the substituent is at least one group selected from C1-C6 alkyl, C1-C6 alkoxy, halogen, and halo C1-C6 alkyl;

R' represents C1-C6 alkyl or halo C1-C6 alkyl;

X represents amino, C1-C6 alkylamino, C1-C6 alkylcarbonylamino, phenylcarbonylamino, benzylamino, or furylmethyleneamino optionally substituted by halo C1-C6 alkyl.

5. The pyridyloxy carboxylate derivative according to claim 4, wherein A and B each independently represent fluoro, chloro, bromo, iodo, methyl, ethyl, propyl, isopropyl, trifluoromethyl, or cyclopropyl;

C represents hydrogen, fluoro, chloro, bromo, iodo, methyl, or trifluoromethyl;

Q represents methyl, ethyl, propyl, isopropyl, cyclopropyl, vinyl, ethynyl, fluoro, chloro, bromo, cyano, amino, nitro, formyl, methoxy, methylthio, methoxycarbonyl, monochloromethyl, monofluoromethyl, difluoromethyl, trifluoromethyl, 2-chloroethyl, 2,2,2-trifluoroethyl, hydroxymethyl, benzyl, naphthyl, furyl, thienyl, thiazolyl, pyridyl, pyrimidinyl,

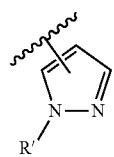

optionally substituted by methyl, or phenyl optionally substituted by at least one group selected from methyl, trifluoromethyl, chloro, and methoxy;

R' represents methyl, ethyl, or difluoromethyl;

M represents

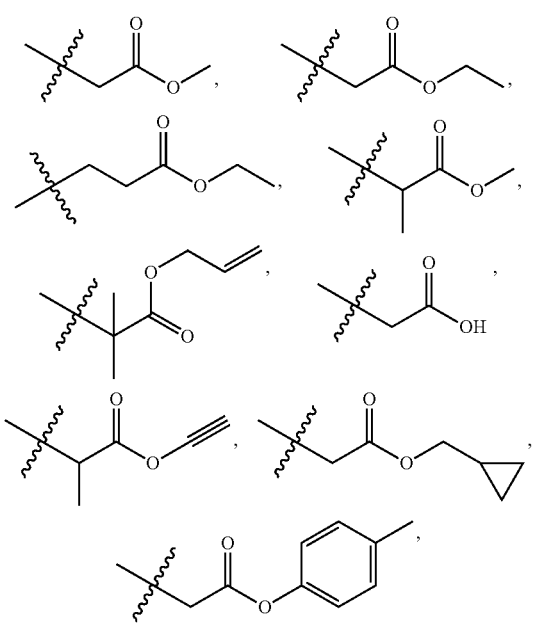

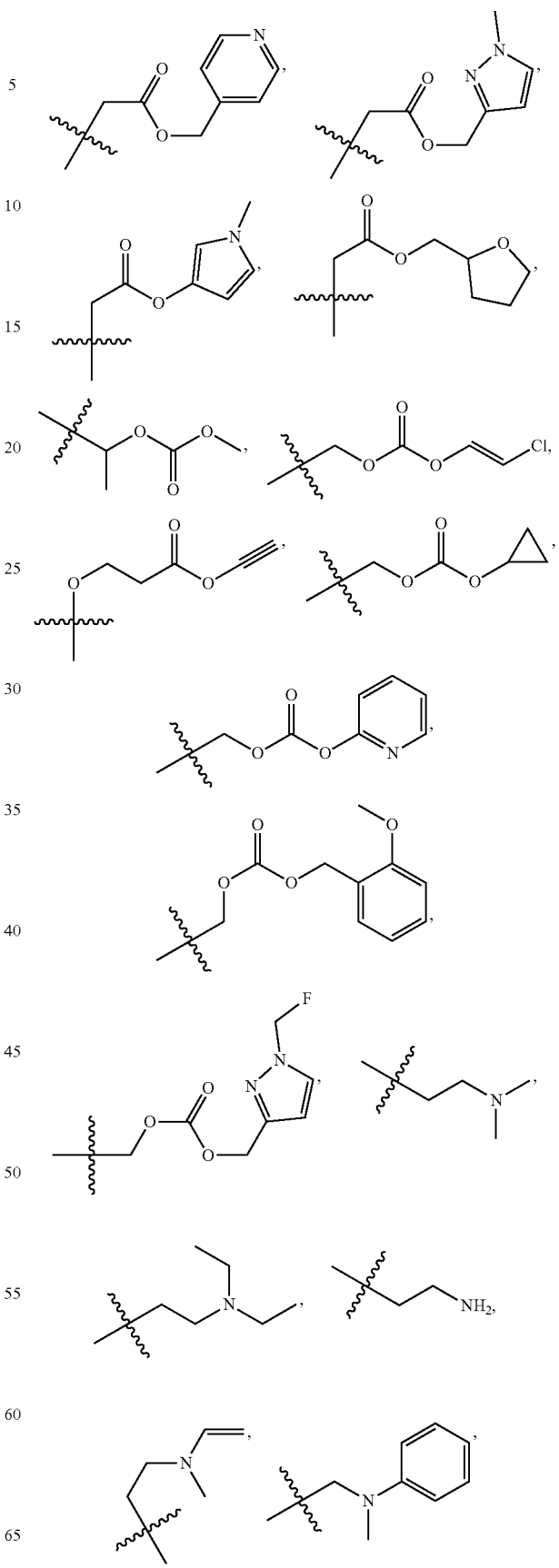

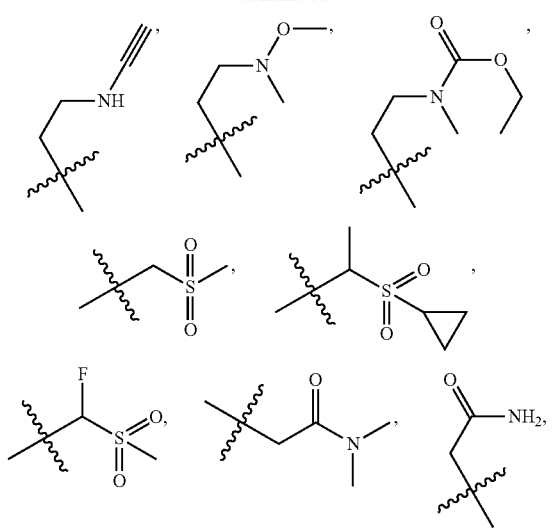
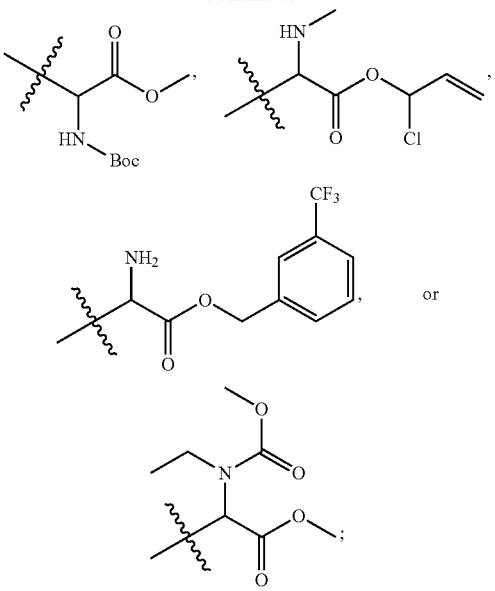
X represents NH₂,
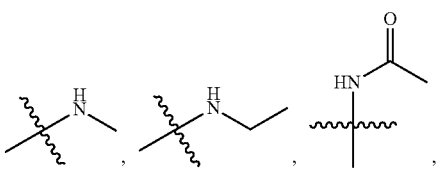
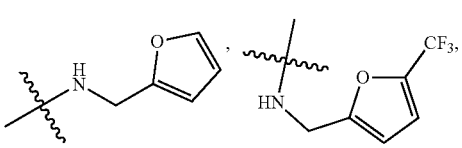
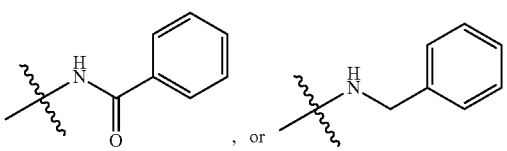
6. The pyridyloxy carboxylate derivative according to claim 5, which is selected from the compounds of formula I as follows:
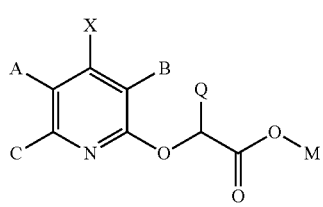

| No. | A | B | C | Q | M | X |
|---|---|---|---|---|---|---|
| 1 | F | F | F | CH$_3$ | 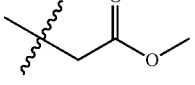 | NH$_2$ |
| 2 | Cl | Cl | Cl | CH$_3$ | 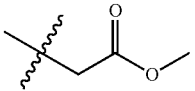 [SMILES: *CC(=O)OC] | NH$_2$ |
| 4 | Cl | Cl | F | CH$_3$ | 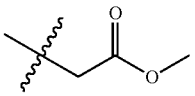 [SMILES: *CC(=O)OC] | NH$_2$ |
| 5 | Cl | Cl | CH$_3$ | CH$_3$ | 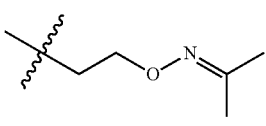 | NH$_2$ |
| 6 | Cl | Cl | CF$_3$ | CH$_3$ | 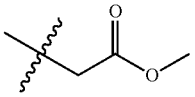 [SMILES: *CC(=O)OC] | NH$_2$ |
| 7 | CH$_3$ | CH$_3$ | F | CH$_3$ | 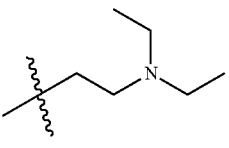 [SMILES: *CCN(CC)CC] | NH$_2$ |
| 8 | Et | Et | CF$_3$ | CH$_3$ | 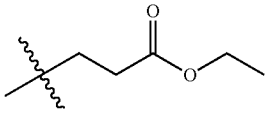 [SMILES: *CCC(=O)OCC] | NH$_2$ |
| 9 |  | Cl | H | CH$_3$ | 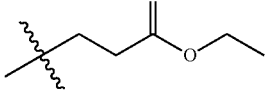 | NH$_2$ |
| 10 |  | Cl | Cl | CH$_3$ | 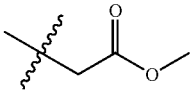 [SMILES: *CC(=O)OC] | NH$_2$ |
| 12 | Br | Br | F | CH$_3$ | 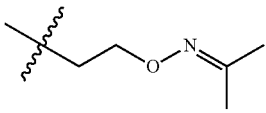 [SMILES: *CCON=C(C)C] | NH$_2$ |
| 13 | I | I | H | CH$_3$ | 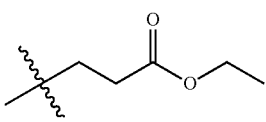 [SMILES: *CCC(=O)OCC] | NH$_2$ |
| 14 | 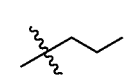 |  | F | CH$_3$ | 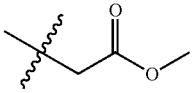 [SMILES: *CC(=O)OC] | NH$_2$ |
| 15 | CF$_3$ | Cl | F | CH$_3$ | 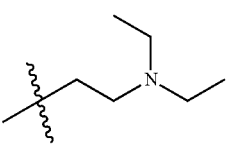 [SMILES: *CCN(CC)CC] | NH$_2$ |

-continued
| No. | A | B | C | Q | M | X |
|---|---|---|---|---|---|---|
| 16 | Cl | CF₃ | H | CH₃ | 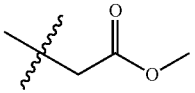 [SMILES: *CC(=O)OC] | NH₂ |
| 18 | Cl | 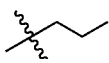 | Br | CH₃ | 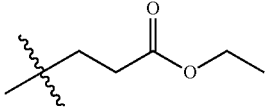 [SMILES: *CCC(=O)OCC] | NH₂ |
| 19 | CH₃ | CH₃ | CH₃ | CH₃ | 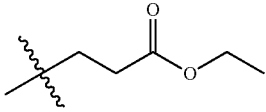 [SMILES: *CCC(=O)OCC] | NH₂ |
| 20 | Cl | CH₃ | F | CH₃ | 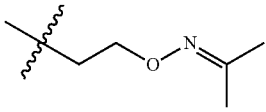 [SMILES: *CCON=C(C)C] | NH₂ |
| 21 | Cl | CH₃ | H | CH₃ | 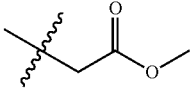 [SMILES: *CC(=O)OC] | NH₂ |
| 23 | Cl | Cl | H | CH₃ | 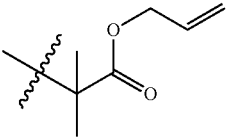 [SMILES: *C(C)(C)C(=O)OCC=C] | NH₂ |
| 24 | Cl | Cl | Cl | CH₃ | 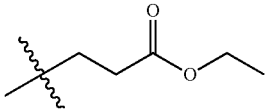 [SMILES: *CCC(=O)OCC] | NH₂ |
| 25 | Cl | Cl | F | Et | 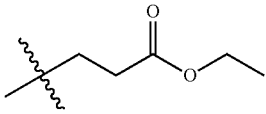 [SMILES: *CCC(=O)OCC] | NH₂ |
| 27 | Cl | Cl | F | 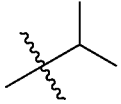 [SMILES: *C(C)C] | 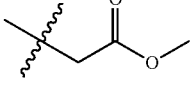 | NH₂ |
| 29 | Cl | Cl | F | 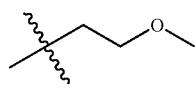 [SMILES: *CCOC] | 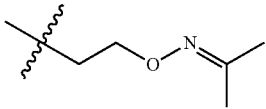 [SMILES: *CCON=C(C)C] | NH₂ |
| 30 | Cl | Cl | F | 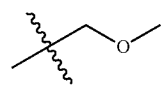 [SMILES: *COC] | 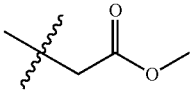 [SMILES: *CC(=O)OC] | NH₂ |
| 31 | Cl | Cl | F | 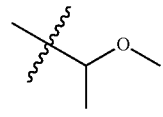 [SMILES: *C(C)OC] | 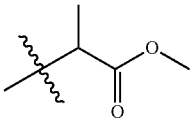 [SMILES: *C(C)C(=O)OC] | NH₂ |

-continued

| No. | A | B | C | Q | M | X |
|---|---|---|---|---|---|---|
| 32 | Cl | Cl | F | CH₂=CH-C(CH₃)- | -CH₂C(CH₃)₂C(O)OCH₃ | NH₂ |
| 33 | Cl | Cl | F | HC≡C-C(CH₃)- | -CH₂C(CH₃)₂C(O)N(CH₃)₂ | NH₂ |
| 35 | Cl | Cl | F | Cl | -CH₂C(CH₃)₂C(O)OCH₃ | NH₂ |
| 38 | Cl | Cl | F | -C(CH₃)(CH₂F)- | -CH₂C(CH₃)₂CH₂C(O)OCH₂CH₃ | NH₂ |
| 39 | Cl | Cl | F | -CHF₂ | -CH₂C(CH₃)₂C(O)OCH₃ | NH₂ |
| 40 | Cl | Cl | F | -C(CH₃)(CH₂CH₂Cl)- | -C(CH₃)₂C(O)OCH₂CH=CH₂ | NH₂ |
| 41 | Cl | Cl | F | CF₃ | -CH₂C(CH₃)₂C(O)OCH₃ | NH₂ |
| 42 | Cl | Cl | F | -C(CH₃)(CH₂CF₃)- | -CH₂C(CH₃)₂C(O)N(CH₃)₂ | NH₂ |
| 43 | Cl | Cl | F | CN | -CH(CH₃)C(O)OCH₃ | NH₂ |
| 44 | Cl | Cl | F | -C(CH₃)(CH₂CN)- | -CH₂C(CH₃)₂C(O)OCH₃ | NH₂ |
| 45 | Cl | Cl | F | NH₂ | -CH₂C(CH₃)₂C(O)OCH₃ | NH₂ |
| 46 | Cl | Cl | F | -C(CH₃)₂CH₂N(CH₃)₂ | -C(CH₃)₂CH₂N(CH₃)₂ | NH₂ |

-continued

| No. | A | B | C | Q | M | X |
|---|---|---|---|---|---|---|
| 48 | Cl | Cl | F | -C(CH3)2CH2OH | -C(CH3)2CH2C(O)OCH3 | NH2 |
| 50 | Cl | Cl | F | -C(CH3)2OCH3 | -C(CH3)2C(O)OCH2CH=CH2 | NH2 |
| 51 | Cl | Cl | F | -C(CH3)2CHO | -C(CH3)2CH2CH2C(O)OCH2CH3 | NH2 |
| 52 | Cl | Cl | F | -C(CH3)2C(O)OCH3 | -C(CH3)2CH2CH2N(CH3)2 | NH2 |
| 53 | Cl | Cl | F | -C(CH3)2CH2Ph | -C(CH3)2CH2C(O)OCH3 | NH2 |
| 54 | Cl | Cl | F | -C(CH3)2-(2-thienyl) | -CH(CH3)OC(O)OCH3 | NH2 |
| 55 | Cl | Cl | F | -C(CH3)2-(3-furyl) | -C(CH3)2CH2CH2C(O)OCH2CH3 | NH2 |
| 56 | Cl | Cl | F | -C(CH3)2-(thiazol-4-yl) | -C(CH3)2CH2C(O)OCH3 | NH2 |
| 58 | Cl | Cl | F | 1,3-dimethyl-1H-pyrazol-4-yl | -C(CH3)2CH2CH2C(O)OCH2CH3 | NH2 |
| 59 | Cl | Cl | F | 1-(difluoromethyl)-1H-pyrazol-3-yl | -CH(CH3)OC(O)OCH3 | NH2 |

-continued
| No. | A | B | C | Q | M | X |
|---|---|---|---|---|---|---|
| 60 | Cl | Cl | F | 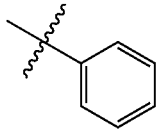 [SMILES: *c1ccccc1] | 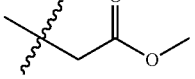 | NH$_2$ |
| 62 | Cl | Cl | F | 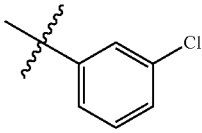 [SMILES: *c1cccc(Cl)c1] | 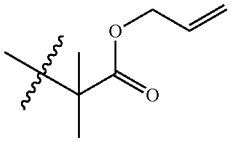 | NH$_2$ |
| 63 | Cl | Cl | F | 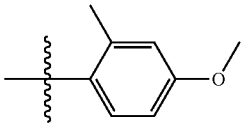 [SMILES: *c1ccc(OC)cc1C] | 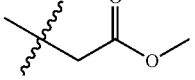 | NH$_2$ |
| 65 | Cl | Cl | F | 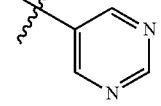 | 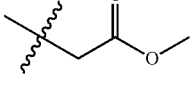 | NH$_2$ |
| 66 | Cl | Cl | F | 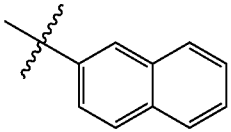 [SMILES: *c1ccc2ccccc2c1] | 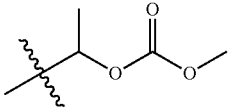 | NH$_2$ |
| 70 | Cl | Cl | F | CH$_3$ | 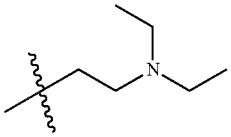 [SMILES: *CCN(CC)CC] | NH$_2$ |
| 71 | Cl | Cl | F | CH$_3$ | 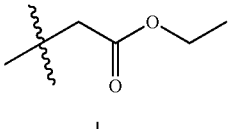 | NH$_2$ |
| 72 | Cl | Cl | F | CH$_3$ |  | NH$_2$ |
| 73 | Cl | Cl | F | CH$_3$ | 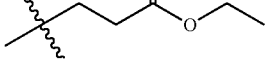 | NH$_2$ |
| 74 | Cl | Cl | F | CH$_3$ | 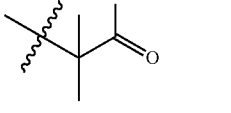 | NH$_2$ |
| 75 | Cl | Cl | F | CH$_3$ | 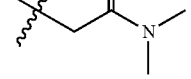 | NH$_2$ |

-continued
| No. | A | B | C | Q | M | X |
|---|---|---|---|---|---|---|
| 76 | Cl | Cl | F | CH₃ | 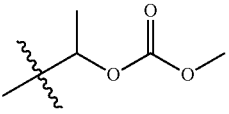 [SMILES: *C(C)OC(=O)OC] | NH₂ |
| 77 | Cl | Cl | F | CH₃ | 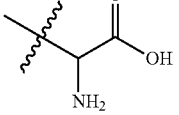 | NH₂ |
| 78 | Cl | Cl | F | CH₃ | 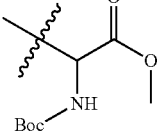 | NH₂ |
| 79 | Cl | Cl | F | CH₃ | 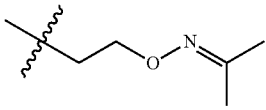 [SMILES: *CCON=C(C)C] | NH₂ |
| 80 | Cl | Cl | F | CH₃ | 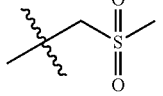 | NH₂ |
| 90 | Cl | Cl | F | CH₃ | 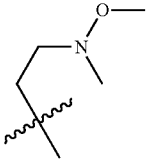 | NH₂ |
| 91 | Cl | Cl | F | CH₃ | 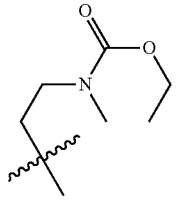 [SMILES: *CCN(C)C(=O)OCC] | NH₂ |
| 92 | Cl | Cl | F | CH₃ | 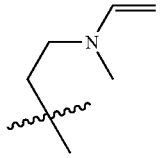 [SMILES: *CCN(C)C=C] | NH₂ |
| 93 | Cl | Cl | F | CH₃ | 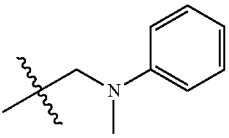 [SMILES: *CN(C)c1ccccc1] | NH₂ |
| 94 | Cl | Cl | F | CH₃ | 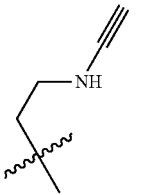 [SMILES: *CCNC#C] | NH₂ |

-continued
| No. | A | B | C | Q | M | X |
|-----|---|---|---|---|---|---|
| 95 | Cl | Cl | F | CH₃ | 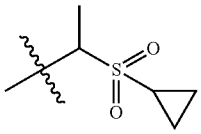 [SMILES: *C(C)S(=O)(=O)C1CC1] | NH₂ |
| 96 | Cl | Cl | F | CH₃ | 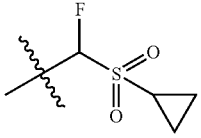 [SMILES: *C(F)S(=O)(=O)C1CC1] | NH₂ |
| 97 | Cl | Cl | F | CH₃ | 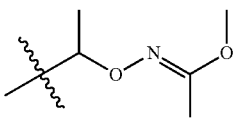 [SMILES: *C(C)O/N=C(\C)OC] | NH₂ |
| 98 | Cl | Cl | F | CH₃ | 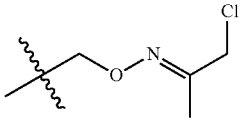 [SMILES: *CO/N=C(\C)CCl] | NH₂ |
| 99 | Cl | Cl | F | CH₃ | 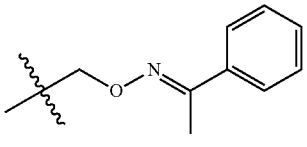 [SMILES: *CO/N=C(\C)c1ccccc1] | NH₂ |
| 100 | Cl | Cl | F | CH₃ | 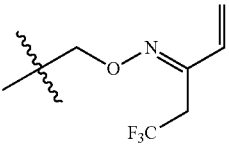 [SMILES: *CO/N=C(/C=C)CC(F)(F)F] | NH₂ |
| 101 | Cl | Cl | F | CH₃ | 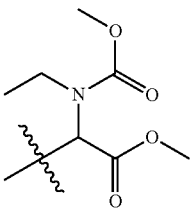 [SMILES: *C(C(=O)OC)N(CC)C(=O)OC] | NH₂ |
| 102 | Cl | Cl | F | CH₃ | 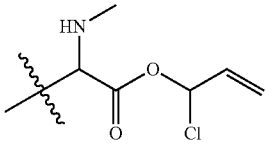 [SMILES: *C(NC)C(=O)OC(Cl)C=C] | NH₂ |
| 103 | Cl | Cl | F | CH₃ | 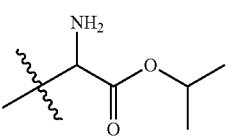 [SMILES: *C(N)C(=O)OC(C)C] | NH₂ |

-continued
| No. | A | B | C | Q | M | X |
|-----|---|---|---|-----|---|-----|
| 104 | Cl | Cl | F | CH₃ | 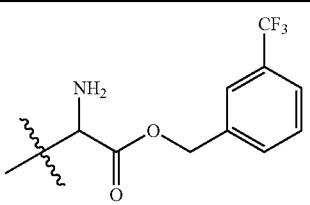 | NH₂ |
| 105 | Cl | Cl | F | CH₃ | 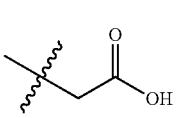 [SMILES: *CC(=O)O] | NH₂ |
| 106 | Cl | Cl | F | CH₃ | 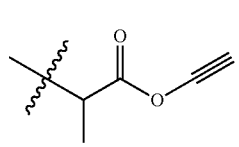 [SMILES: *C(C)C(=O)OC#C] | NH₂ |
| 107 | Cl | Cl | F | CH₃ | 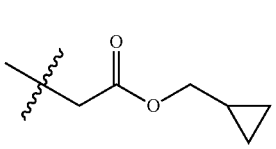 [SMILES: *CC(=O)OCC1CC1] | NH₂ |
| 108 | Cl | Cl | F | CH₃ | 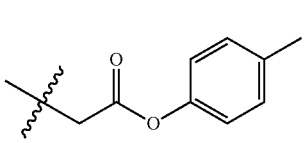 [SMILES: *CC(=O)Oc1ccc(C)cc1] | NH₂ |
| 109 | Cl | Cl | F | CH₃ | 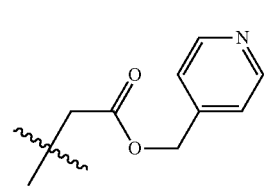 [SMILES: *CC(=O)OCc1ccncc1] | NH₂ |
| 110 | Cl | Cl | F | CH₃ | 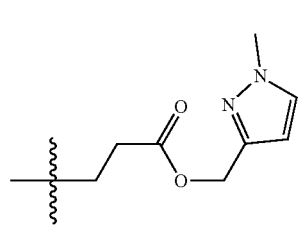 [SMILES: *CCC(=O)OCc1ccn(C)n1] | NH₂ |
| 111 | Cl | Cl | F | CH₃ | 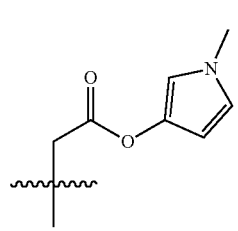 [SMILES: *CC(=O)Oc1ccn(C)c1] | NH₂ |
| 112 | Cl | Cl | F | CH₃ | 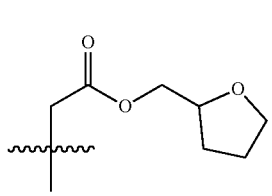 [SMILES: *CC(=O)OCC1CCCO1] | NH₂ |

-continued
| No. | A | B | C | Q | M | X |
|---|---|---|---|---|---|---|
| 113 | Cl | Cl | F | CH₃ | 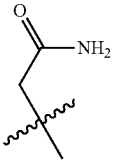 | NH₂ |
| 114 | Cl | Cl | F | CH₃ | 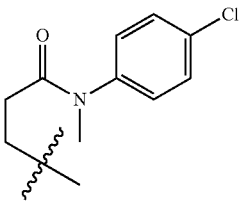 [SMILES: *CCC(=O)N(C)c1ccc(Cl)cc1] | NH₂ |
| 115 | Cl | Cl | F | CH₃ | 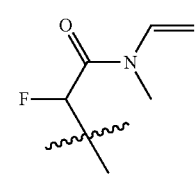 [SMILES: *C(F)C(=O)N(C)C=C] | NH₂ |
| 116 | Cl | Cl | F | CH₃ | 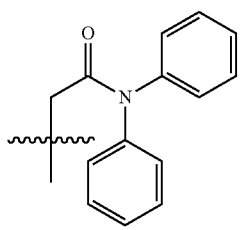 [SMILES: *CC(=O)N(c1ccccc1)c1ccccc1] | NH₂ |
| 117 | Cl | Cl | F | CH₃ | 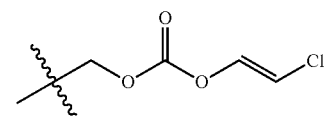 [SMILES: *COC(=O)O/C=C/Cl] | NH₂ |
| 118 | Cl | Cl | F | CH₃ | 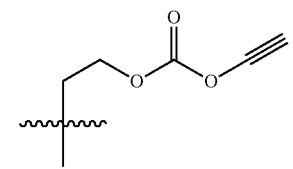 [SMILES: *CCOC(=O)OC#C] | NH₂ |
| 119 | Cl | Cl | F | CH₃ | 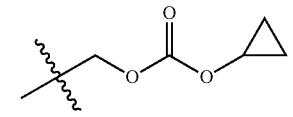 [SMILES: *COC(=O)OC1CC1] | NH₂ |
| 120 | Cl | Cl | F | CH₃ | 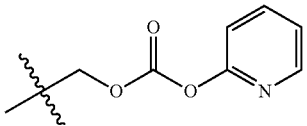 [SMILES: *COC(=O)Oc1ccccn1] | NH₂ |
| 121 | Cl | Cl | F | CH₃ | 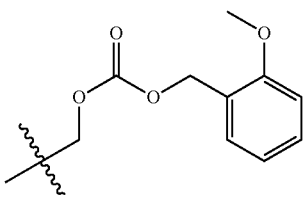 [SMILES: *COC(=O)OCc1ccccc1OC] | NH₂ |

-continued
| No. | A | B | C | Q | M | X |
|---|---|---|---|---|---|---|
| 122 | Cl | Cl | F | CH₃ | 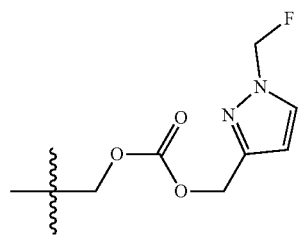 [SMILES: *COC(=O)OCc1ccn(CF)n1] | NH₂ |
| 124 | Cl | Cl | F | CH₃ | 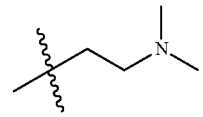 | 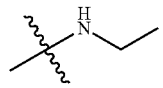 [SMILES: *NCC] |
| 125 | Cl | Cl | F | CH₃ | 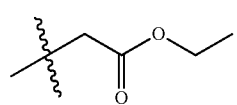 [SMILES: *CC(=O)OCC] | 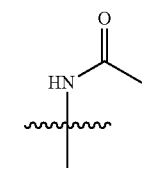 [SMILES: *NC(C)=O] |
| 126 | Cl | Cl | F | CH₃ | 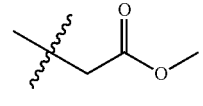 | 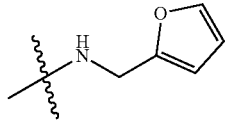 [SMILES: *NCc1ccco1] |
| 127 | Cl | Cl | F | CH₃ | 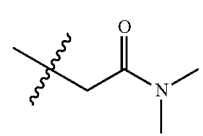 [SMILES: *CC(=O)N(C)C] | 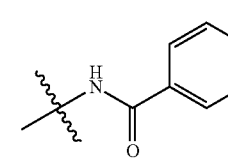 |
| 128 | Cl | Cl | F | CH₃ | 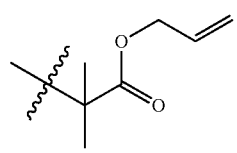 [SMILES: *C(C)(C)C(=O)OCC=C] | 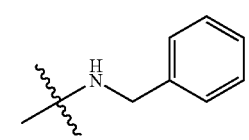 [SMILES: *NCc1ccccc1] |
| 129 | Cl | Cl | F | CH₃ | 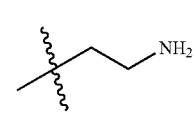 [SMILES: *CCN] | NH₂ |
| 130 | Cl | Cl | F | CH₃ | 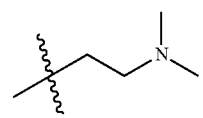 [SMILES: *CCN(C)C] | NH₂ |
| 132 | Cl | Cl | F | CH₃ | 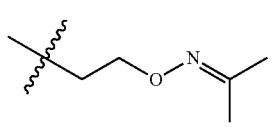 [SMILES: *CCON=C(C)C] | 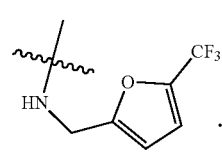 [SMILES: *NCc1ccc(C(F)(F)F)o1 ; "."] |

7. A method of preparing the pyridyloxy carboxylate derivative of claim 1, comprising:
(1) reacting a compound of formula III with a compound of formula II to obtain a compound of formula I as follows:

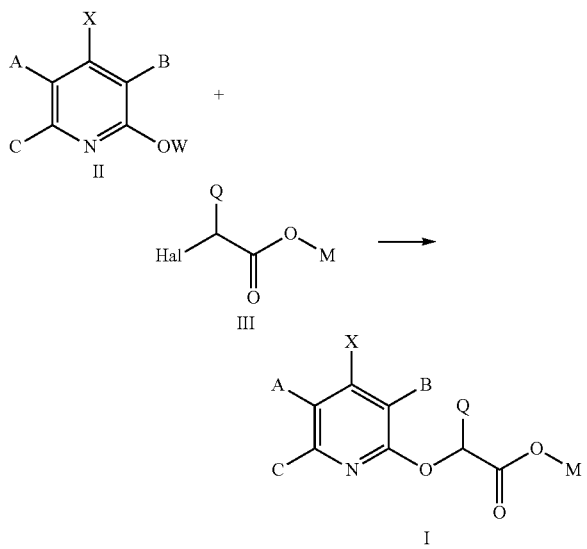

wherein, W represents an alkali metal, and Hal represents halogen; or
(2) when X represents $NR_1R_2$, wherein $R_1$ and $R_2$ are not hydrogen at the same time, reacting a compound of formula I-1

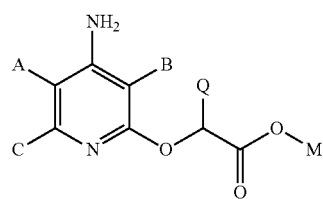

with a corresponding halide to obtain a compound of formula I, when $R_1$ is hydrogen and $R_2$ is not hydrogen, the corresponding halide represents $R_2$-Hal; when $R_2$ is hydrogen and $R_1$ is not hydrogen, the corresponding halide represents $R_1$-Hal; when $R_1$ is not hydrogen and $R_2$ is not hydrogen, the corresponding halide represents $R_1$-Hal and $R_2$-Hal.

8. The method of claim 7, wherein in step (1), the reaction is carried out in the presence of a catalyst and a solvent.

9. The method of claim 8, wherein the catalyst is TBAB, and the solvent is one or more selected from DCM, DCE, ACN, THF, and DMF.

10. The method of claim 7, wherein in step (2), the reaction is carried out in the presence of a base and a solvent, and a catalyst is optionally added during the reaction.

11. The method of claim 10, wherein the base is one or more selected from sodium hydroxide, potassium hydroxide, sodium carbonate, potassium carbonate, sodium bicarbonate, and cesium carbonate; the solvent is one or more selected from THF, 1,4-dioxane, toluene, 1,2-dichloroethane, ethyl acetate, acetonitrile, DMF, acetone, dichloromethane, and chloroform; and the catalyst is DMAP.

12. A herbicidal composition comprising (i) at least one pyridyloxy carboxylate derivative of claim 1; optionally further comprising (ii) at least one additional herbicide and/or safener, and/or (iii) at least one agrochemically acceptable formulation auxiliary.

13. A method for controlling a weed, comprising applying a herbicidally effective amount of at least one pyridyloxy carboxylate derivative of claim 1 on a plant or in a weed area.

14. The method of claim 13, wherein the plant is rice or soybean; or the weed is a gramineous weed, a broad-leaved weed, or a cyperaceae weed.

15. The method of claim 13, wherein the plant is japonica rice, indica rice, or soybean; or the weed is *Echinochloa crusgalli, Digitaria sanguinalis, Monochoria Vaginalis, Abutilon theophrasti, Galium spurium,* or *Cyperus iria.*

16. A method for controlling a weed in a useful crop, comprising applying at least one pyridyloxy carboxylate derivative of claim 1 to the useful crop.

17. The method of claim 16, wherein the useful crop is a genetically modified crop, or a crop treated by gene editing technology.

18. The method of claim 16, wherein the useful crop is rice or soybean; or the weed is a gramineous weed, a broad-leaved weed, or a cyperaceae weed.

19. The method of claim 16, wherein the useful crop is japonica rice, indica rice, or soybean; or the weed is *Echinochloa crusgalli, Digitaria sanguinalis, Monochoria Vaginalis, Abutilon theophrasti, Galium spurium,* or *Cyperus iria.*

* * * * *

UNITED STATES PATENT AND TRADEMARK OFFICE
CERTIFICATE OF CORRECTION

| | | |
|---|---|---|
| PATENT NO. | : 12,408,666 B2 | Page 1 of 1 |
| APPLICATION NO. | : 17/414478 | |
| DATED | : September 9, 2025 | |
| INVENTOR(S) | : Lei Lian et al. | |

It is certified that error appears in the above-identified patent and that said Letters Patent is hereby corrected as shown below:

In the Claims

Claim 3, Column 85, Lines 36-37, "representhalogen" should read as --represent halogen--.

Claim 3, Column 87, Line 42, "$R_11$," should read as --$R_{11}$--.

Claim 3, Column 91, Line 21, "cyclo alkenyl" should read as --cycloalkenyl--.

Claim 3, Column 93, Line 50, "Wherein" should read as --wherein--.

Claim 14, Column 120, Line 30, "cyperaceae" should read as --Cyperaceae--.

Claim 18, Column 120, Line 43, "cyperaceae" should read as --Cyperaceae--.

Signed and Sealed this
Twenty-third Day of December, 2025

John A. Squires
*Director of the United States Patent and Trademark Office*